United States Patent
Finberg et al.

(12)

(10) Patent No.: US 6,210,921 B1
(45) Date of Patent: *Apr. 3, 2001

(54) CAR: A NOVEL COXSACKIEVIRUS AND ADENOVIRUS RECEPTOR

(76) Inventors: Robert W. Finberg, 48 Spring Rd., Canton, MA (US) 02021; Jeffrey M. Bergelson, 517 Old Gulph Rd., Narberth, PA (US) 19072; Marshall S. Horwitz, 127 E. Garden Rd., Larchmont, NY (US) 10538

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/928,383

(22) Filed: Sep. 12, 1997

Related U.S. Application Data

(60) Provisional application No. 60/026,100, filed on Sep. 13, 1996.

(51) Int. Cl.$^7$ ................................................. C12N 15/00
(52) U.S. Cl. ..................... 435/69.1; 435/320.1; 435/325; 435/252.3; 435/254.11; 536/23.5; 536/23.1; 530/350
(58) Field of Search ................................ 435/69.1, 320.1, 435/325, 252.3, 254.11, 7.2, 7.21; 536/73.5, 73.1; 530/350

(56) References Cited

U.S. PATENT DOCUMENTS 5,942,606 * 8/1999 Lal ........................................ 536/23.1

FOREIGN PATENT DOCUMENTS

WO 93/17041  9/1993  (WO).

OTHER PUBLICATIONS

Hillier et al, The WashU–Merck EST project, Genbank Accession No. W39780, May 15, 1996, and N31467, Jan. 10, 1996.*

Fujiwara et al., Otsuka cDNA project, Genbank Accession No. C16023, Sep. 1996.*

Genexpress, The Genexpress cDNA program, Genbank Accession No. Z44690, Sep. 1995.*

Bergelson et al., Science 275:1320–3, Feb. 1997.*

Tomko et al., PNAS 94:3352–6, 1997.*

Bergelson, J.M. et al., The Murine CAR Homolog is a Receptor for Coxsackie B Viruses and Adenoviruses, *Journal of Virology* 72(1):1–5 (1998).

Bergelson, J.M. et al., Isolation of a Common Receptor for Coxsackie B Viruses and Adenoviruses 2 and 5, *Science* 275:1320–1323(Feb. 28, 1997).

Hsu, K.L. et al., A Monoclonal Antibody Specific for the Cellular Receptor for the Group B Coxsackieviruses, *Journal of Virology* 62(5):1647–1652 (1988).

Grist, N.R. and Reid D., Epidemiology of Viral Infections of the Heart, In: *Viral Infections of the Heart*, J. Banatvala, ed. (London: Edward Arnold), pp. 23–31 (1993).

Yoon, J. et al., Virus–Induced Diabetes Mellitus, *New England Journal of Medicine* 300(21):1173–1179 (1979).

Woodruff, J.F., Viral Myocarditis, *American Journal of Pathology*, 101:427–479 (1980).

Lerner, A.M. and Wilson, F.M., Virus Myocardiopathy,*Prog. med. Virol.* 15:63–91 (1973).

Xu, R. et al., "Receptor Proteins on Newborn Balb/c Mouse Brain Cells for Coxsackievirus B3 are Immunologically Distinct from Those on HeLa Cells", *Virus Research,* vol. 35, 323–40 (1995).

* cited by examiner

*Primary Examiner*—Lorraine Spector
*Assistant Examiner*—Eliane Lazar-Wesley

(57) ABSTRACT

The invention provides isolated nucleic acid molecules which encode a coxsackievirus and adenovirus receptor protein, CAR. The invention also provides antisense nucleic acid molecules, recombinant expression vectors containing CAR nucleic acid molecules, host cells into which the expression vectors have been introduced, and nonhuman transgenic animals in which a CAR gene has been introduced or disrupted. The invention still further provides isolated CAR proteins, fusion proteins, antigenic peptides and anti-CAR antibodies. Diagnostic, screening, and therapeutic methods utilizing compositions of the invention are also provided.

8 Claims, 20 Drawing Sheets

A. Sequences of tryptic peptides

|  | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Peptide 1 | T | Q [K] | Y | N | Q [K] | V | P | S | E | D | F | E | R | |
| Peptide 2 | T | P | Q [K] | S | P | T | L [I] | P | P | A | K | | | |
| Peptide 3 | V | A | A | P | N | L [I] | S | R | | | | | | |
| Peptide 4 | M | G | A | I [I] | P | V | M | I [I] | P | A | Q [K] | S | K [Q] | |

Fig. 1A

CAR amino acid sequence

1 MALLLCFVLLCGVVDFARSLSITTPEEMIEKAKGETAYLPCKFTLSPEDQ

51 GPLDIEWLISPADNQKVDQVIILYSGDKIYDDYYPDLKGRVHFTSNDLKS
                    *
101 GDASINVTNLQLSDIGTYQCKVKKAPGVANKKIHLVVLVKPSGARCYVDG

151 SEEIGSDFKIKCEPKEGSLPLQYEWQKLSDSQKMPTSWLAEMTSSVISVK
    *
201 NASSEYSGTYSCTVRNRVGSDQCLLRLNVVPPSNKAGLIAGAIIGTLLAL
                                                      *
251 ALIGLIIFCCRKKRREEKYEKEVHHDIREDVPPPKSRTSTARSYIGSNHS
                                                *
300 SLGSMSPSNMEGYSK<u>TQYNQVPSEDFERTPQSPTLPPAKVAAPNLSRMGA</u>

351 <u>IPVMIPAQSKDGSIV</u>

| | | |
|---|---|---|
| 1 | h<br>m1.2 | MALLLCFVLLCGVVDFARSLSITTPEEMIEKAKGETAYLPCKFTLSPEDQ<br>--R---------IA--TSG------QR---------------------- |
| 51 | h<br>m1.2 | GPLDIEWLISPADNQKVDQVIILYSGDKIYDDYYPDLKGRVHFTSNDLKS<br>-----------S---I----------------N--------------V--<br>           * |
| 101 | h<br>m1.2 | GDASINVTNLQLSDIGTYQCKVKKAPGVANKKIHLVVLVKPSGARCYVDG<br>------------------------------FL-T-------T--F--- |
| 151 | h<br>m1.2 | SEEIGSDFKIKCEPKEGSLPLQYEWQKLSDSQKMPTSWLAEMTSSVISVK<br>-----N---L------------F---------T-----------P-----<br> * |
| 201 | h<br>m1.2 | NASSEYSGTYSCTVRNRVGSDQCLLRLNVVPPSNKAGLIAGAIIGTLLAL<br>--------------Q--------M---D------R--T----V------- |
| 251 | h<br>M1.2 | ALIGLIIFCCRKKRREEKYEKEVHHDIREDVPPPKSRTSTARSYIGSNHS<br>V---A-L---HR-------------------------------------- |
| 300 | h<br>m1<br>m2 | SLGSMSPSNMEGYSKTQYNQVPSEDFERTPOSPTLPPAKVAAPNLSRMGA<br>-----------------------------A------A--------------<br>-----------------------------A------A---FKYAYKTDGIT |
| 351 | h<br>m1<br>m2 | IPVMIPAQSKDGSIV<br>V--------------<br>VV |

Fig. 7

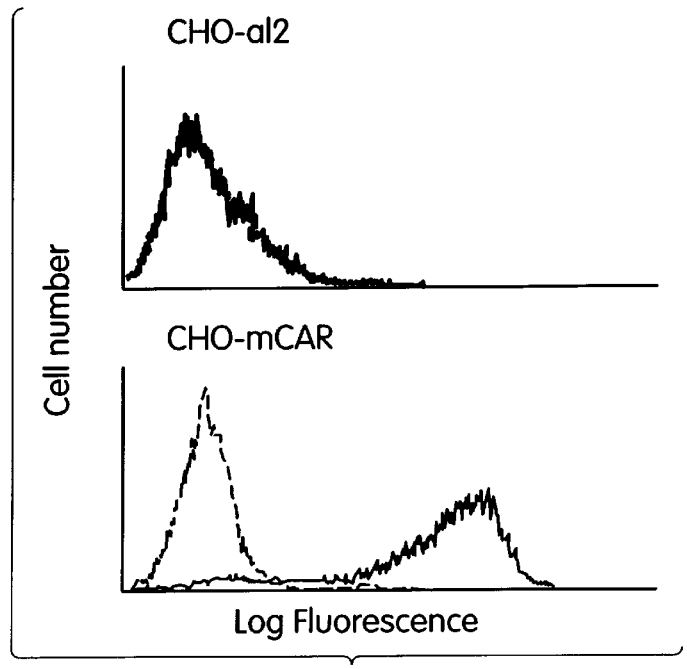

Fig. 8

1
GAATTCCCAGGAGCGAGAGCCGCCTACCTGCAGCCGCCGCCCACGGCACGGCAGCCACCATGGCGC
TCCTGCTGTGCTTCGTGCTCCTGTGCGGAGTAGTGGATTTCGCCAGAAGTTTGAGTATCACTACTC
CTGAAGAGATGATTGAAAAAGCCAAAGGGGAAACTGCCTATCTGACGTGCAAATTTACGCTTAGTC
CCGAAGACCAGGGACCGCTGGACATCGAGTGGCTGATATCACCAGCTGATAATCAGAAGGTGGATC
AAGTGATTATTTTATATTCTGGAGACAAAATTTATGATGACTACTATCCAGATCTGAAAGGCCGAG
TACATTTTACGAGTAATGATCTCAAATCTGGTGATGCATCAATAAATGTAACGAATTTACAACTGT
CAGATATTGGCACATATCAGTGCAAAGTGAAAAAAGCTCCTGGTGTTGCAAATAAGAAGATTCATC
TGGTAGTTCTTGTTAAGCCTTCAGGTGCGAGATGTTACGTTGATGGATCTGAAGAAATTGGAAGTG
ACTTTAAGATAAAATGTGAACCAAAAGAAGGTTCACTTCCATTACAGTATGAGTGGCAAAAATTGT
CTGACTCACAGAAAATGCCCACTTCATCGTTAGCAGAAATGACTTCATCTGTTATATCTGTAAAAA
ATGCCTCTTCTGAGTACTCTGGGACATACAGCTGTACAGTCAGAAACAGAGTGGGCTCTGATCAGT
GCCTGTTGCGTCTAAACGTTGTCCCTCCTTCAAATAAAGCTGGACTAATTGCAGGAGCCATTATAG
GAACTTTGCTTGCTCTAGCGCTCATTGGTCTTATCATCTTTTGCTGTCGTAAAAAGCGCAGAGAAG
AAAAATATGAAAAGGAAGTTCATCACGATATCAGGGAAGATGTGCCACCTCCAAAGAGCCGTACGT
CCACTGCCAGAAGCTACATCGGCAGTAATCATTCATCCCTGGGGTCCATGTCTCCTTCCAACATGG
AAGGATATTCCAAGACTCAGTATAACCAAGTACCAAGTGAAGACTTTGAACGCACTCCTCAGAGTC
CGACTCTCCCACCTGCTAAGGTAGCTGCCCCTAATCTAAGTCGAATGGGTGCGATTCCTGTGATGA
TTCCAGCACAGAGCAAGGATGGGTCTATAGTATAGAGCCTCCATATGTCTCATCTGTGCTCTCCGT
GTTCCTTTCCTTTTTTTGATATATGAAAACCTATTCTGGTCTAAATTGTGTTACTAGCCTCAAAAT
ACATCAAAAAATAAGTTAATCAGGAACTGTACGGAATATATTTTTAAAAATTTTTGTTTGGTTATA
TCGAAATAGTTACAGGCACTAAAGTTAGTAAAGAAAAGTTTACCATCTGAAAAAGCTGGATTTTCT
TTAAGAGGTTGATTATAAAGTTTTCTAAATTTATCAGTACCTAAGTAAGATGTAGCGCTTTGAATA
TGAAATCATAGGTGAAGACATGGGTGAACTTACTTGCATACCAAGTTGATACTTGAATAACCATCT
GAAAGTGGTACTTGATCATTTTTACCATTATTTTTAGGATGTGTATTTCATTTATTTATGGCCCAC

CAR: A NOVEL COXSACKIEVIRUS AND ADENOVIRUS RECEPTOR

RELATED APPLICATION

This application claims priority to the U.S. Provisional Application Serial No. 60/026,100 entitled "CAR, A Novel Coxsackievirus and Adenovirus Receptor," filed Sep. 13, 1996, the teachings of which are incorporated herein by reference.

GOVERNMENT FUNDING

Work described herein was supported under grants AI35667, AI31628 and CA69703 awarded by the National Institutes of Health. The U.S. government therefore may have certain rights in this invention.

BACKGROUND OF THE INVENTION

Adenoviruses and coxsackieviruses are common human pathogens. Adenoviruses, non-enveloped DNA viruses, are a major cause of respiratory and gastrointestinal infections (Horwitz, In Virology, 3rd edition: 2149–2171 1996), as well as infections of the heart (Martin et al., Circulation, 90: 330–339 1994). In addition to their importance as disease agents, adenoviruses have been adapted for use as vectors for vaccination and gene therapy (Kremer and Perricaudet, British Medical Bulletin, 51: 31–44, 1995). Coxsackie B viruses, non-enveloped RNA viruses belonging to the picornavirus family, cause non-specific febrile illnesses and meningoencephalitis (Melnick, In Virology, 3rd edition: 655–712, 1996), and are the viruses most frequently identified in acute infections of the heart (Grist and Reid, In Viral Infection of the Heart, 23–31, 1993; Savoia and Oxman, In Principles and Practice of Infectious Diseases, 4th edition, 799–813, 1995). Coxsackie B viruses are also implicated in acute pancreatitis (Imrie et al., Gut, 18: 53–56, 1977) and as triggering-agents in childhood-onset diabetes (Yoon et al., New England Journal of Medicine, 300: 1173–1179, 1979; Clements et al., Lancet, 346: 221–223, 1995).

Viruses initiate infection by attaching to cell surface receptors, and tissue-specific expression of receptor molecules is an important determinant of virus tropism. Adenovirus attachment to cells is mediated by elongated fibers projecting from each of the 12 vertices of the icosahedral viral capsid. Isolated soluble fibers bind cells with high affinity, and block virus attachment and infection, demonstrating that fiber attachment to a cell surface receptor is a critical event in infection (Philipson et al., J. Virology, 49: 635–640, 1968; Defer et al., J. Virology, 64: 3661–3673, 1990; Wickham et al., Cell, 73: 309–319, 1993). Human adenoviruses are grouped on the basis of their ability to agglutinate erythrocytes. Competition experiments suggest that adenoviruses 2 and 5 (members of agglutination group C) share a common cellular receptor (Philipson et al., J. Virology, 49: 635–640, 1968; Defer et al., J. Virology, 64: 3661–3673, 1990), distinct from the receptor used by group B viruses such as adenovirus 3 (Defer et al., J. Virology, 64: 3661–3673, 1990; Stevenson et al., J. Virology, 69: 2850–2857, 1995) or 35. Although a number of cellular proteins associate with adenovirus on affinity columns (Hennache and Boulanger, Biochemical Journal, 166: 237–247, 1977; Svensson et al., J. Virology, 38: 70–81, 1981) or in virus overlay blot assays (Defer et al., J. Virology, 64: 3661–3673, 1990), the cellular molecules responsible for fiber-mediated adenovirus attachment have not been identified.

Twenty years ago, it was demonstrated that adenovirus 2 or its fibers compete with coxsackievirus B3 for a cell surface attachment site, suggesting that these unrelated viruses share a receptor protein (Lonberg-Holm et al., Nature, 259: 679–681, 1976). More recently, coxsackie B viruses have been shown to interact with at least two cell-surface proteins (Reagan et al., J. Virology, 49: 635–640, 1984), Decay accelerating factor (DAF, CD55) serves as an attachment receptor for some coxsackie B virus strains (Bergelson et al., J. Virology, 69: 1903–1906, 1995; Shafren et al., J. Virology, 69: 3873–3877, 1995). Expression of human DAF on rodent cells permits these strains to bind, but not to replicate, suggesting that additional factors may be required for infection.

A second 45–50 kD putative receptor molecule forms a detergent-stable complex with coxsackieviruses B3 and B4 (Mapoles et al., J. Virology, 55: 560–566, 1985; Hsu et al., In New Aspects of Positive-Strand RNA Viruses, 271–277, 1990). A monoclonal antibody raised against this complex is reported to protect cells from infection by all six coxsackie B serotypes (Hsu et al., J. Virology, 62: 1647–1652, 1988), consistent with the observation that all six serotypes compete for a single cell surface receptor (Crowell and Tomko, In Cellular Receptors for Animal Viruses, 75–99, 1994).

SUMMARY OF THE INVENTION

This invention pertains to isolated nucleic acid molecules (e.g., cDNAs) comprising a nucleotide sequence encoding a coxsackievirus and adenovirus receptor protein, CAR, as well as nucleic acid fragments suitable as hybridization probes for the detection of CAR encoding nucleic acid (e.g, mRNA). Another aspect of the invention pertains to isolated or purified CAR protein and biologically active fragments thereof. Still yet another aspect of the invention pertains to recombinant expression vectors containing the nucleic acid molecules of the invention and host cells into which such recombinant expression vectors have been introduced. In one embodiment, such a host cell is used to produce CAR protein by culturing the host cell in a suitable medium. If desired, CAR protein can be then isolated from the medium or the host cell. Another aspect of the invention pertains to modulation of the activity of CAR in the treatment of infection. In one embodiment, an antisense nucleic acid molecule is used to down-regulate CAR expression. In another embodiment, an antibody raised against the CAR protein is used to block CAR expression. Yet another aspect of the invention pertains to enhancing transduction, in particular adenovirus, transduction by initiating or increasing CAR expression in a host cell.

BRIEF DESCRIPTION OF THE DRAWING

FIG. 1. CAR amino acid sequence.

Figure 2A:
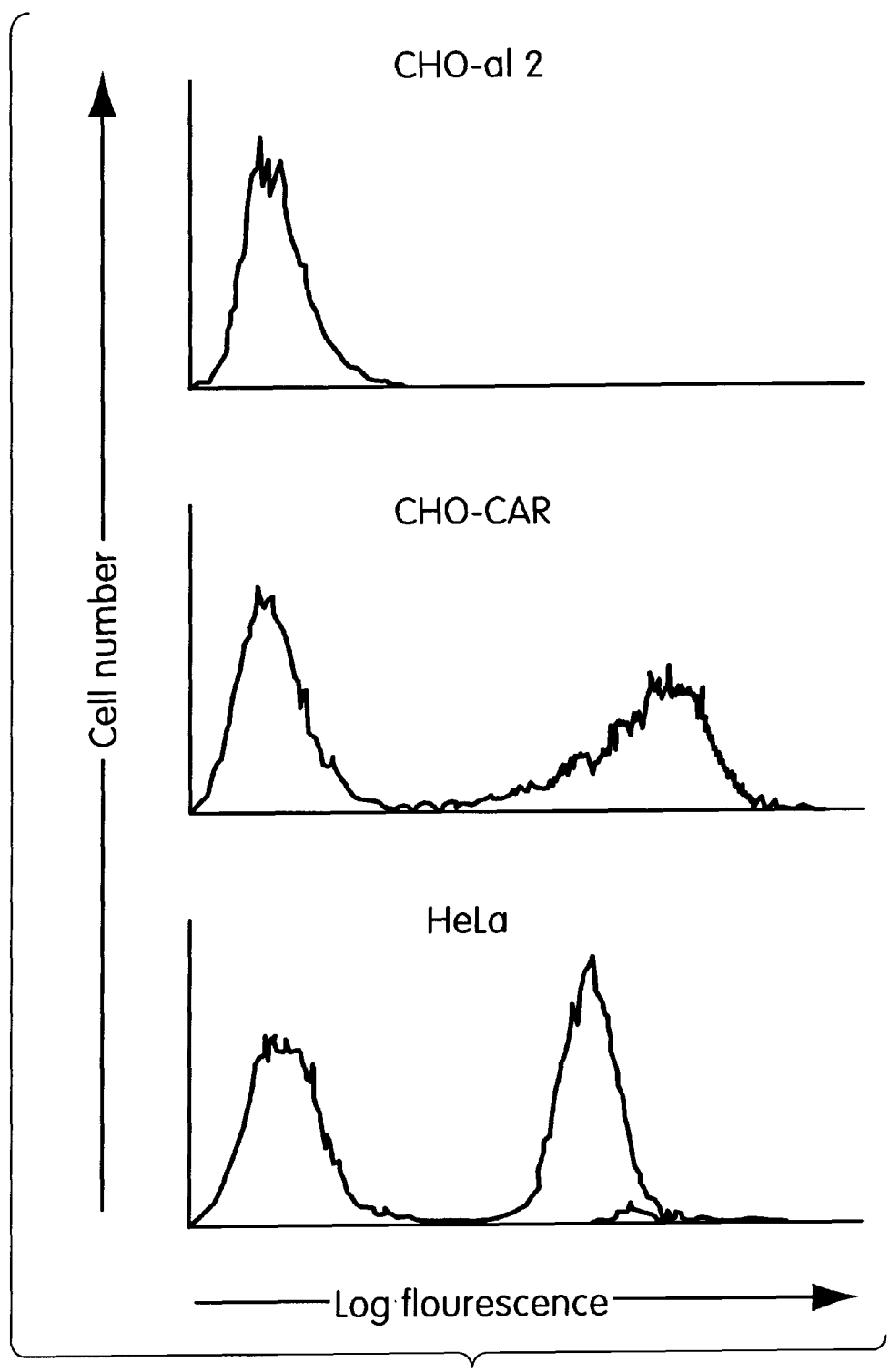

A. Sequences of tryptic peptides (Peptide 1, SEQ ID NO.: 4, Peptide 2, SEQ ID NO.: 5, Peptide 3, SEQ ID NO.: 6, Peptide 4, SEQ ID NO.: 7). CAR protein purified by affinity chromatography using MAb RmcB was digested with trypsin, and the sequences of individual peptides were determined by CAD mass spectroscopy. Q/K and I/L have identical masses and cannot be distinguished.

B. Predicted CAR amino acid sequence (SEQ ID NO.: 2). The predicted hydrophobic leader and transmembrane domains are in bold print. Amino acids experimentally determined by peptide sequencing are underlined. Potential sites for N-linked glycosylation are marked with an asterisk. Tyrosine 255 (KRREEKY) is a potential site for phosphorylation.

C. Alignment of the CAR amino acid sequence with sequences of immunoglobulin gene family members. Residues identical to CAR are shaded. Where at least half of the aligned sequences share a residue with CAR (SEQ ID NO.: 8), residues are boxed. Domain 1: CTX (SEQ ID No.: 9) (xenopus thymocyte protein, gi 1335866); B7-2 (SEQ ID NO.: 10) (murine CD86, sp P42082); VCAM-1 (SEQ ID NO.: 11) (murine, sp P29533); C-FMS (SEQ ID NO.: 12) CONTAC (SEQ ID NO.: 13) (human contactin, gb U07820); TCRg (SEQ ID NO.: 14) (bovine T cell receptor gamma subunit, gi 2175290; TCRa (SEQ ID) NO.: 15) (murine T-cell receptor alpha chain V region, pir 24402); IgV (SEQ ID NO.: 16) (African clawed frog Ig heavy chain V region, pir S22558). Domain 2: CAR (SEQ ID NO.: 17) CTX (SEQ ID NO.: 18) HSPG (2, 9) (SEQ ID NO.: 19, SEQ ID NO.: 20) (murine heparan sulfate proteoglycan core protein Ig-like domains 2 and 9, sp Q05793); PECAM (SEQ ID NO.: 21) (human CD31, pir JL0142); VCAM-1 (SEQ ID NO.: 22) (human, sp P19320).

FIG. 2. Expression of CAR protein on transfected CHO cells

A. Immunofluorescence. CHO cells transfected with CAR (CHO-CAR), control CHO cells transfected with the integrin α2 subunit (CHO-al 2), and HeLa cells were incubated with MAb RmcB or the control mycloma protein MOPC 195 for one hour on ice, then cells were washed and incubated with fluorescein isothiocyanate-conjugated goat anti-mouse immunoglobulin and analyzed by flow cytometry. RmcB staining is shown with the thicker line in each panel.

B. Immunoprecipitation. HeLa cells, CHO-CAR cells, or control CHO-alpha 2 cells were iodinated, extracted in buffer containing 1% Triton X-100, and immunoprecipitation was performed with the control antibody MOPC 195 (M) or MAb RmcB (R) bound to protein G-Sepharose beads. Immunoprecipitated proteins were analyzed in 10% SDS-polyacrylamide gels under reducing conditions. Molecular weights of marker proteins are indicated in kD.

FIG. 3. Coxsackie B virus interaction with CAR on transfected CHO cells.

A. Virus attachment. CHO-CAR or CHO-alpha 2 monolayers were incubated with MAb RmcB or with the control myeloma protein MOPC 195 for 1 hour at room temperature, then rinsed and incubated for 4 hours with $^{35}$S-labeled coxsackievirus B3 or coxsackievirus B4 (20,000 cpm). Monolayers were then washed and dissolved, and cell-bound radioactivity was measured in a scintillation counter. The figure shows mean virus bound (counts per minute) ±SD for triplicate monolayers.

B. Virus infection. CHO-CAR or CHO-alpha 2 monolayers were incubated for 1 hr at room temperature with coxsackievirus B3 (1 PFU/cell) or coxsackievirus B4 (4 PFU/cell), then monolayers were washed to remove unbound virus and incubated at 37° C. for 1 hr (0 days), 1 day, or 2 days. Monolayers were frozen and thawed to release virus, and plaque assays were performed. The figure shows the mean virus titer for triplicate cultures.

FIG. 4. Attachment of adenovirus and adenovirus fibers to CAR.

A. Adenovirus 2 and 35. CHO-CAR, CHO-alpha 2, and HeLa monolayers were incubated with $^{35}$S-labeled adenoviruses (20,000 cpm) for 1 hour at room temperature, then monolayers were washed to remove unbound virus and dissolved for scintillation counting.

B. Adenovirus 2 fibers. CHO-CAR, CHO-alpha 2, and HeLa monolayers were incubated with $^{35}$S-labeled adenovirus fibers (15,000 cpm) for 90 min at room temperature, then monolayers were washed and dissolved for scintillation counting.

C. Inhibition by adenovirus 5 knob domains. CHO-CAR or HeLa monolayers were incubated with recombinant knob domains before addition of radiolabeled viruses. Each panel shows mean virus or fiber bound (counts per minute) ±SD for triplicate mono layers.

FIG. 5. Adenovirus-mediated gene transfer to CAR-transfected CHO cells

A. In situ staining with X-gal. CHO-CAR and CHO alpha-2 cells in 24 well plates were exposed to Ad.CMV-βgal at different multiplicities of infection for 1 hr at room temperature, then unbound virus was removed and cells were incubated for 40 hr at 37° C. Cells were fixed with 2% paraformaldehyde and β-galactosidase activity was determined by incubation with X-gal.

B. β-galactosidase activity in cell lysates. CHO-CAR, CHO alpha-2 and HeLa cells in 24 well plates were exposed to Ad5.CMV-βgal at different multiplicities of infection for 1 hr at room temperature, then unbound virus was removed and cells were incubated for 40 hr at 37° C. Cells were lysed and β-galactosidase activity was measured in a kinetic assay. Results are shown as the $V_{max}$ in mOD/min ±SD for triplicate lysates.

Figure 6:
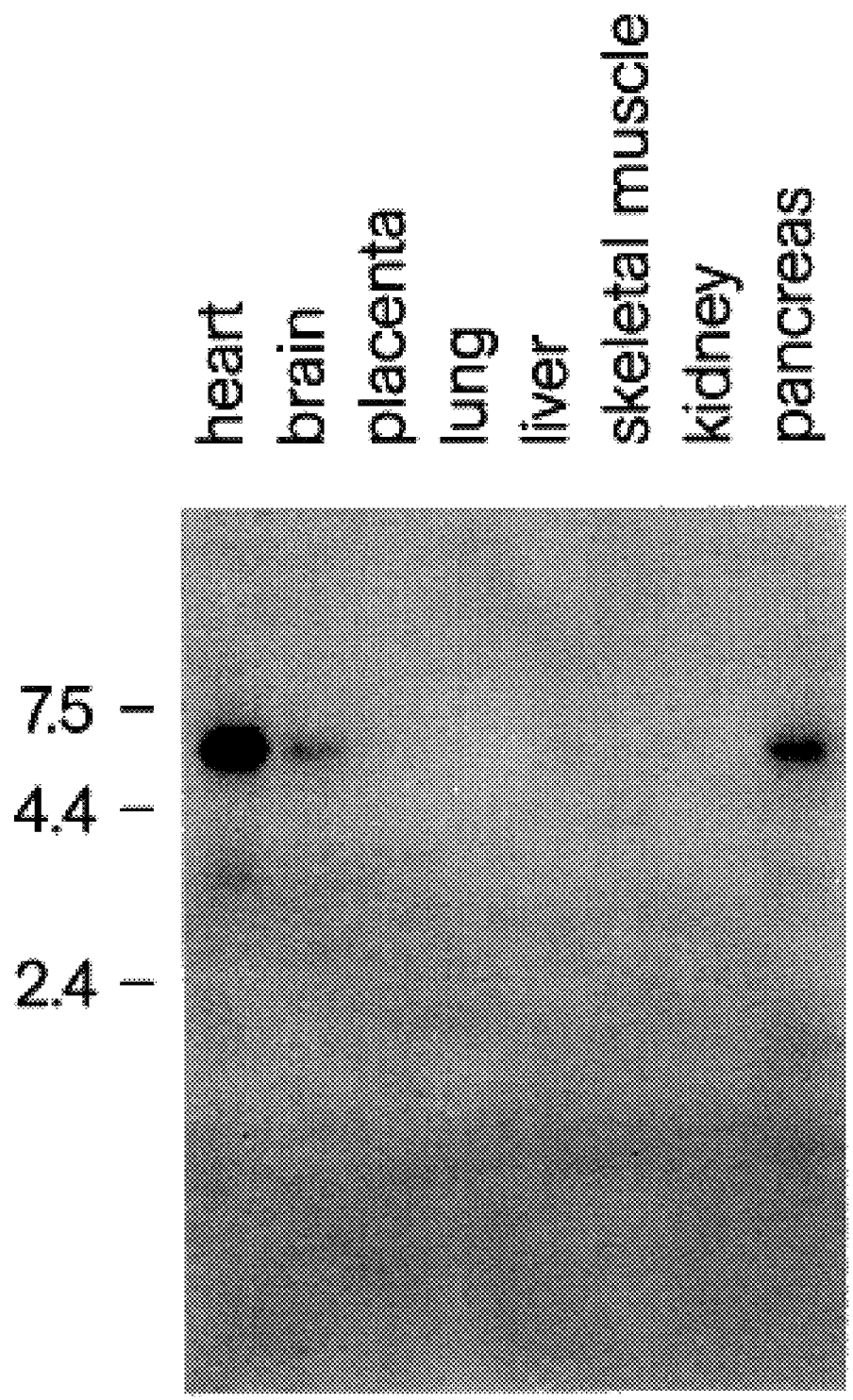

FIG. 6. RNA blot analysis of CAR expression in human tissues

A multiple tissue Northern blot (Clontech) containing 2 mcg of poly A$^+$ RNA from each of the indicated tissues was probed with the complete coding region of CAR RNA. Positions of marker RNAs are indicated in kilobases. Hybridization with a human actin probe confirmed the presence of equivalent amounts of RNA in each lane.

FIG. 7. Murine and human CAR amino acid sequences

The human CAR sequence (h), (SEQ ID NO.: 2) the sequence of a murine homologue (clone m1), (SEQ ID NO.: 23) and a murine homologue with an altered C-terminus (clone m2) (SEQ ID NO.: 24) are shown. Predicted hydrophobic leader [determined as in Nielson, H., J. Engelbrecht, S. Brunak, and G. v. Heijne, 1997, Identification of prokaryotic and eukaryotic signal peptides and prediction of their cleavage sites, *Protein engineering*, 10: 1–6] and transmembrane domains are underlined. Potential sites for N-linked glycosylation are marked with an asterisk.

FIG. 8. Expression of mCAR on transfected CHO cells

Control CHO cells transfected with the human integrin α2 subunit (CHO-aI2) or CHO cells transfected with mCAR cDNA (clone m2, CHO-mCAR) were incubated first with normal rat serum (dotted line) or with serum from rats immunized with the 46 kD mouse brain receptor (solid line), then with FITC-conjugated goat antibody to rat immunoglobulin. Results with clone m2 are shown; similar results were obtained with clone m1.

Figure 9:
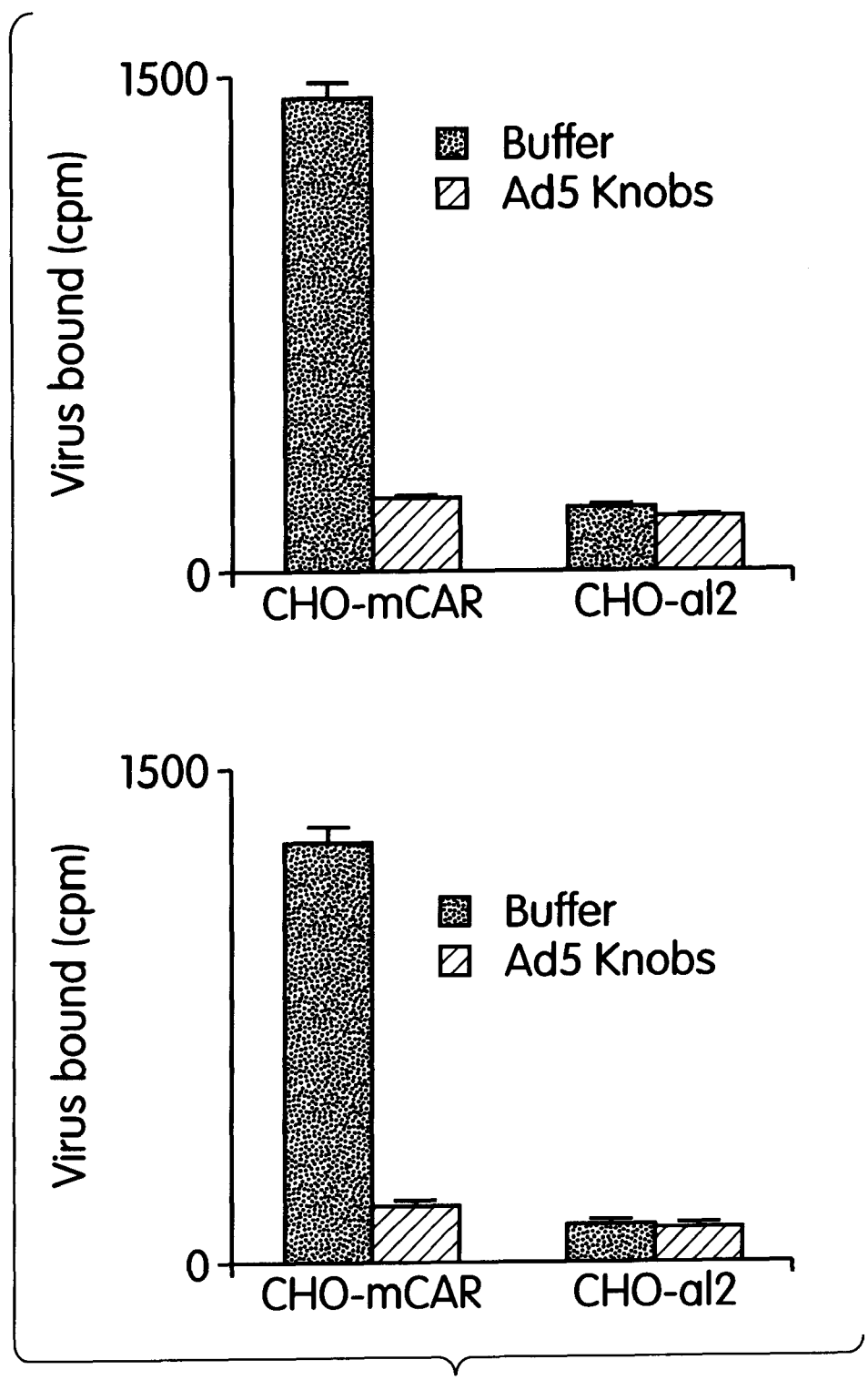

FIG. 9. Coxsackie B virus attachment to mCAR on transfected CHO cells

Confluent monolayers of CHO-mCAR or control CHO-al2 cells were incubated with radiolabeled CB3 or CB4 (29,000 cpm) for 4 hr at room temperature, then washed and dissolved for scintillation counting. Results with clone m2 are shown; similar results were obtained with clone m1. Some monolayers are preincubated with recombinants adenovirus 5 knob domains (0.7 μg) before exposure to radiolabeled virus. Mean virus bound (cpm+1SD) is shown for triplicate samples.

Figure 10:
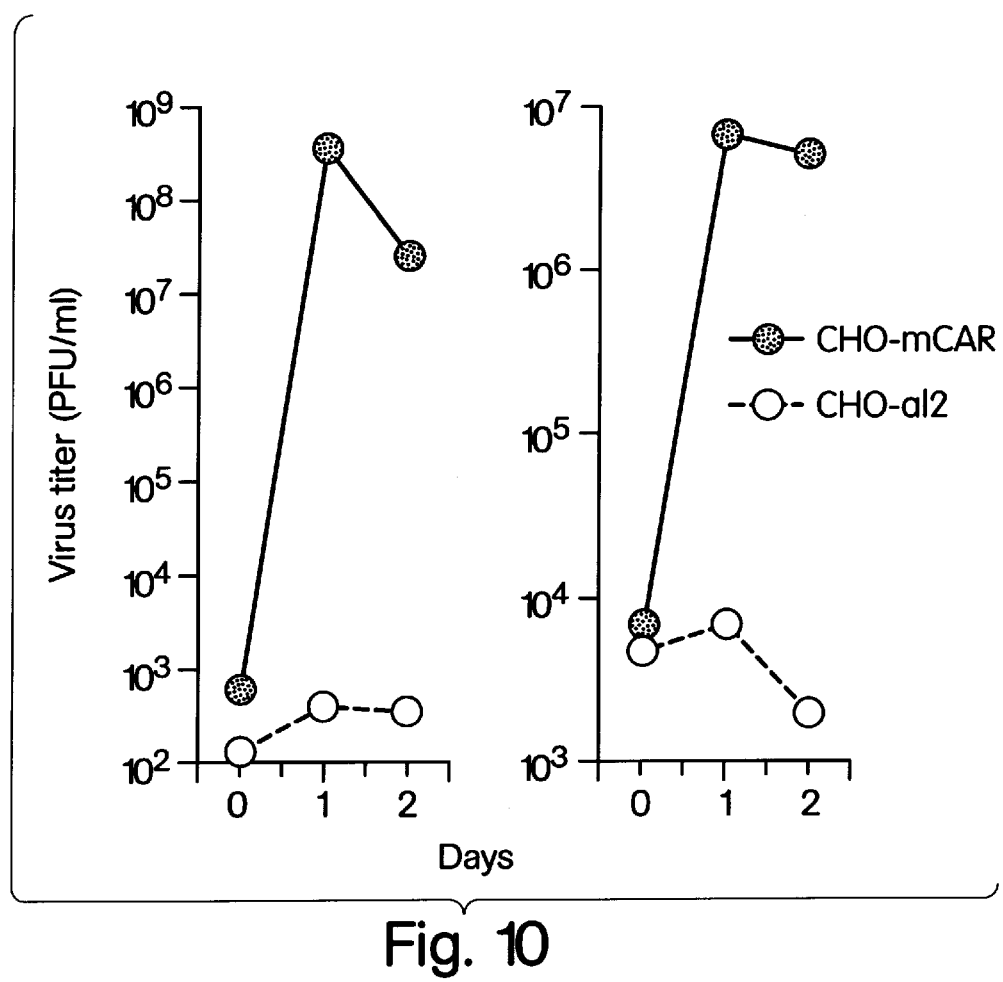

FIG. 10. Coxsackievirus production by transfected CHO cells

Figure 11:
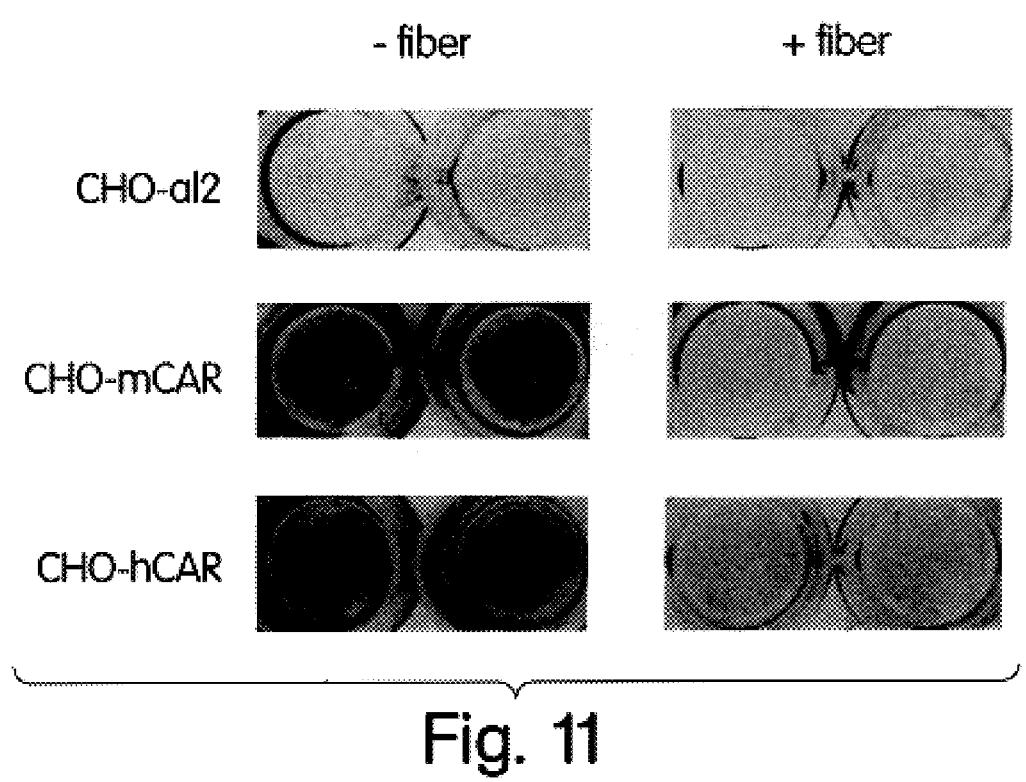

CHO-mCAR and CHO-al2 monolayers were exposed to CB3 or CB4 (10 PFU/cell) for 1 hr at room temperature, then FIG. 11. Adenovirus-mediated gene transfer Duplicate monolayers of CHO-al2, CHO-mCAR, or CHO cells transfected with human CAR cDNA (CHO-hCAR) were exposed to Ad.CMV-βgal for one hour at room temperature, then monolayers were washed. After incubation at 37° C. for 40 hrs, β-galactosidase activity was detected by in situ staining with X-gal. Some monolayers were incubated with 1.5 µg of purified adenovirus 2 fibers before exposure to virus. Results with clone m2 are shown; similar results were obtained with clone m1.

Figure 12:
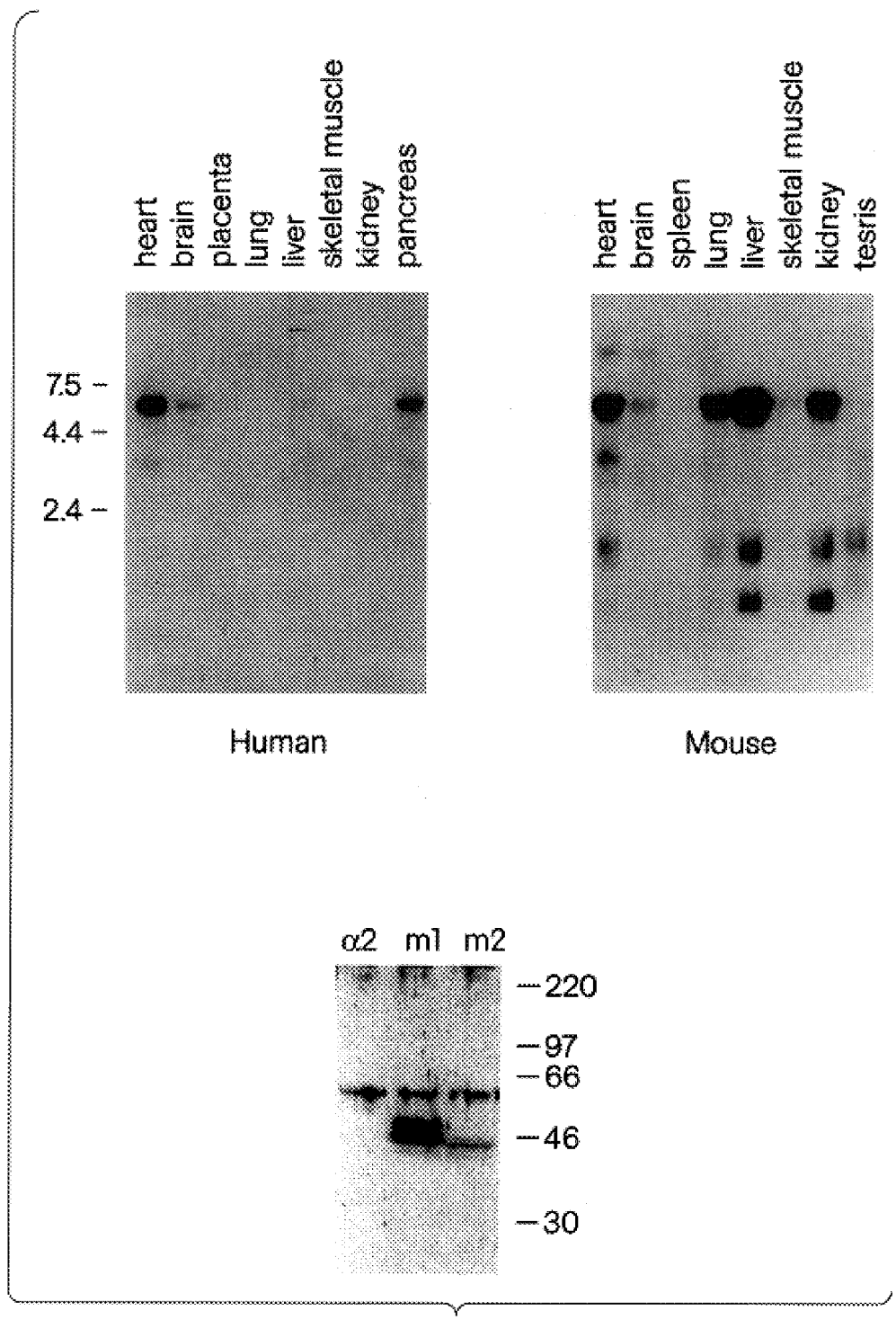

FIG. 12. CAR mRNA expression in human and murine tissues

Multiple tissue Northern blots (Clontech) containing 2 mcg of poly A+RNA from each of the indicated tissues were probed with human and murine CAR cDNA as described in Materials and Methods. Positions of marker RNAs are indicated in kilobases. Hybridization with a human actin probe confirmed the presence of equivalent amounts of RNA in each lane.

FIG. 13. Human DNA CAR Sequence

Human DNA CAR sequence (SEQ ID NO.: 1) is shown with the coding region highlighted.

Figure 14:
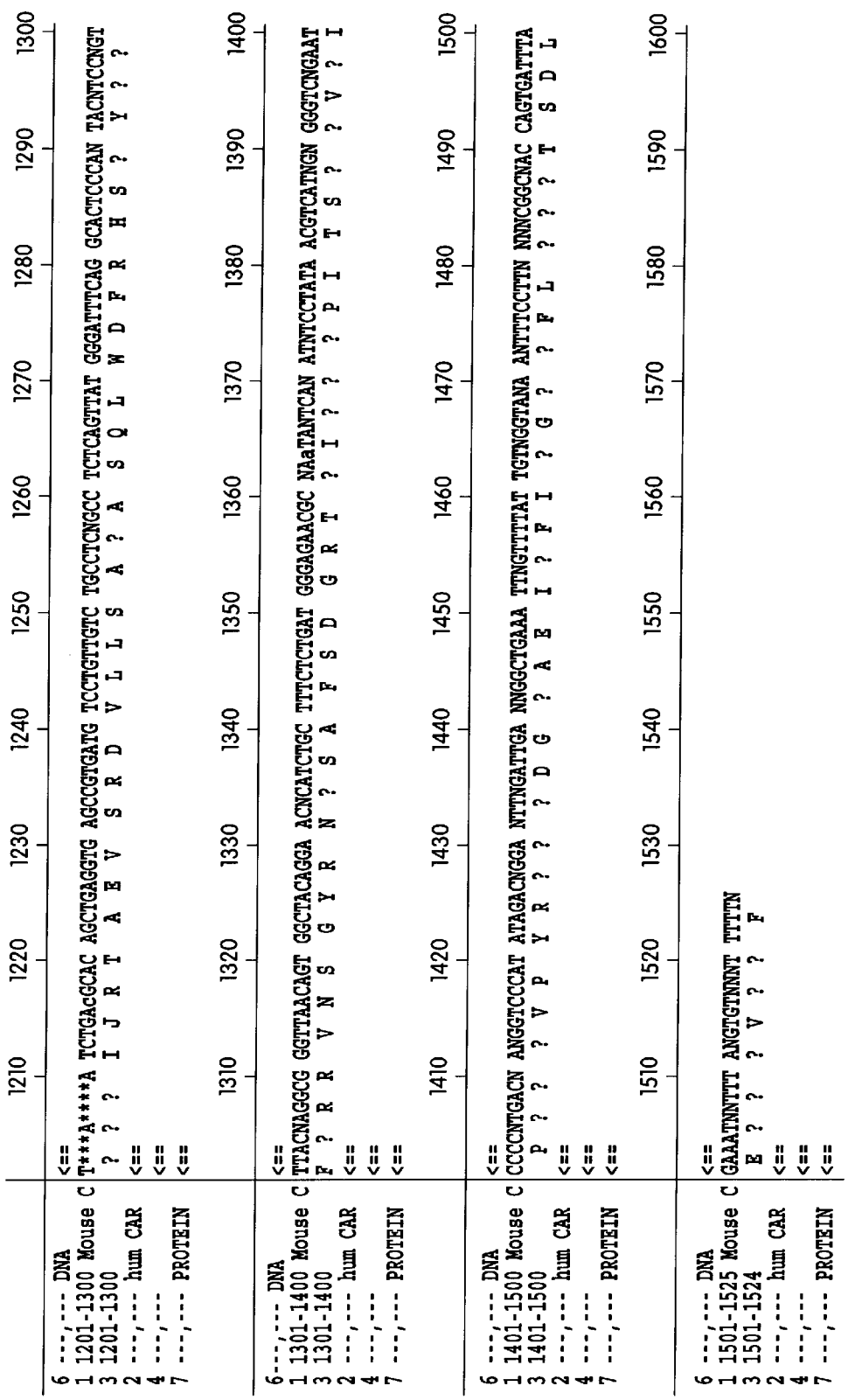

FIG. 14. DNA Mouse CAR, DNA Human CAR, and Protein Alignment Alignment of DNA Mouse CAR, (SEQ ID NO.: 25), Protein CAR (SEQ ID NO.: 26) DNA Human CAR, (SEQ ID NO.: 1, Protein Human CAR (SEQ ID NO.: 2) and Protein.

DETAILED DESCRIPTION OF THE INVENTION

The present invention is based on the discovery of novel molecules which serve as an attachment receptor for coxsackie B viruses and adenoviruses and is referred to herein as CAR nucleic acid (For example, the human CAR DNA sequence as shown in FIG. 13) and protein molecules (For example, the alignment of human CAR DNA, mouse CAR DNA, and protein as shown in FIG. 14). The coxsackie B and adenovirus receptor (CAR) is a novel transmembrane protein with a distinctive pattern of expression in human tissues. The relatively large cytoplasmic domain suggests the potential for interaction with other intracellular proteins.

CAR as a coxsackievirus receptor

Expression of CAR protein on CHO cells renders them susceptible to infection by coxsackieviruses B3 and B4, confirming that this protein is a functional receptor. MAb RmcB prevents virus attachment to CAR. This antibody was previously shown to protect cells from infection by prototype strains of all six coxsackie B serotypes (Hsu, K.-H. L., et al. J. Virol. 62, 1647–1652), consistent with the observation that all six serotypes compete for a common cell surface attachment site (Crowell, R. L. and Tomko, R. P. (1994). Receptors for picornaviruses. In Cellular Receptors for Animal Viruses, E. Wimmer, ed. (Plainview, N.Y.: Cold Spring Harbor Laboratory Press), pp. 75–99. It is likely that CAR is the major receptor for all coxsackie B viruses.

Some strains of coxsackie B1, B3 and B5 have gained the capacity to bind to an additional receptor, the complement regulatory protein decay accelerating factor (DAF) (Bergelson, J. M., et al.Mohanty, (1995). J. Virology 69, 1903–1906; Shafren, D. R. et al., (1995). J. Virology 69, 3873–3877). The coxsackie B3 strain used in these experiments does not bind to DAF. CB3-RD (Reagan, K. J., et al. (1984). J. Virology 49, 635–640), a coxsackie B3 variant known to bind DAF (Bergelson et al., 1995), also binds to CHO cells expressing CAR, confirming that this virus strain interacts with two receptors. Interestingly, virus attachment to CHO-CAR transfectants leads to productive infection, but attachment to CHO-DAF transfectants does not. It is possible that DAF functions in virus attachment for some strains, but that subsequent events, such as virus internalization, and the initiation of virus uncoating, depend on interaction with CAR. The recently determined three dimensional structure of coxsackievirus B3 is remarkable for the presence of two distinct surface depressions, which have been proposed to be the attachment sites for two cellular receptors (Muckelbauer, J. K., et al. (1995). Structure 3, 653–667). A canyon surrounding the icosahedral five-fold axis of symmetry may be the site where CAR attaches. The rhinovirus receptor, ICAM-1, like CAR a member of the immunoglobulin gene superfamily, binds to a similar canyon on the rhinovirus surface (Olson, N. H., et al. (1993). Proc. Natl. Acad. Sci. USA 90, 507–511).

In a survey of human tissues, CAR mRNA was most highly expressed in myocardium, consistent with the known tropism of coxsackie B viruses for the heart, where they are the viruses most frequently implicated in acute viral myocarditis and pericarditis (Lerner, A. M. and Wilson, F. M. (1973). Prog. Med. Virol. 15, 63–91; Woodruff, J. (1980). Am. J. Pathol. 101, 427–479; Grist, N. R. and Reid, D. (1993). Epidemiology of viral infections of the heart. In Viral Infections of the Heart, J. Banatvala, ed. (London: Edward Arnold), pp.23–31). In a number of studies, nearly half of patients with acute myocarditis showed evidence of recent coxsackie B infection, and World Health Organization surveillance indicates that up to 4% of coxsackie B infections are associated with cardiac disease [reviewed in (Grist and Reid, 1993)]. Although the relationship is controversial, coxsackievirus myocarditis may contribute to the subsequent development of dilated cardiomyopathy (Easton, A. J. and Eglin, R. P. (1988). J. Gen. Virol. 69, 285–291; Muir, P., et al. (1989). Lancet i, 804–807; Jin, O., et al. (1990). Circulation 82, 8–16; Kandolf, R., et al. (1991). Eur. Heart. J. 80 (suppl D), 49–55; Schwaiger, A., et al. (1993). Am. Heart J. 126, 406–410), an illness leading to 9,000 deaths in the U.S. each year (Grist and Reid, 1993).

High levels of CAR expression were also seen in the brain and pancreas, and CAR cDNA has been isolated from brain and pancreatic islet cell libraries. Central nervous system infection by coxsackieviruses is common (Melnick, J. L. (1996). In Virology, B. N. Fields, D. M. Knipe and P. M. Howley, eds. (Philadelphia: Lippincott-Raven), 3rd edition, pp. 655–712), and abnormalities of pancreatic function are reported to be frequent in children infected by coxsackie B (Nakao, et al. (1964). Tohoku Journal of Experimental Medicine 83, 94–102). In addition, coxsackie B virus infection of the pancreas has been proposed to be a trigger for childhood onset diabetes mellitus (Yoon, J. W., et al. (1979). New England Journal of Medicine 300, 1173–79; Clements, G. B., et al. (1995). Lancet 346, 221–223). The correspondence between the tissue-specific expression of CAR mRNA and the major clinical syndromes caused by coxsackie B viruses suggests that CAR is an important determinant of virus tropism in vivo.

CAR as an adenovirus receptor

Adenovirus enters cells by receptor-mediated endocytosis (Pastan, I., et al. (1987). Adenovirus entry into cells: some new observations on an old problem. In Concepts in Viral Pathogenesis, A. Notkins and M. Oldstone, eds. (New York:

Springer-Verlag), pp. 141–146), and within the endosomal compartment is disassembled in a stepwise process that results in release of viral DNA (Greber, U. F., et al. (1993). Cell75, 477–486). Despite considerable interest in the early events in adenovirus infection, and several efforts to isolate proteins with affinity for virus (Meager, A., et al. (1976). Eur. J. Biochem. 61, 345–353; Hennache, B. and Boulanger, P. (1977). Biochemical Journal 166, 237–247; Svensson, U., et al. (1981). J. Virology 38, 70–81), the cell surface molecule responsible for virus attachment had not been identified previously. The experiments described here demonstrate that adenovirus binds to the same protein, CAR, that functions as a receptor for coxsackie B viruses.

Adenovirus attachment to most cell types is mediated by 186 kD fiber structures projecting from the virus capsid (Philipson, L., et al. (1968). Virus-receptor interaction in an adenovirus system. J. Virology 2, 1064–1075). A globular knob at the tip of each fiber binds directly to the cellular receptor (Henry. L. J., et al. (1994). J. Virology 68, 5239–5246; Louis, N., et al. (1994). J. Virology 68, 4104–4106; Stevenson, S. C., et al. (1995). J. Virology 69, 2850–2857). Isolated fibers as well as intact virions bound specifically to CHO cells expressing CAR protein, and virus attachment to CHO-CAR cells was prevented by isolated knob domains. From its crystal structure (Xia, D., (1994). Structure 2, 1259–1270), the knob is a trimer, with three identical domains arranged as a trefoil. A deep central depression and three radiating valleys are located at the three-fold axis of symmetry, facing away from the virus surface. This depression is likely to be the site at which virus attaches to CAR. Adenovirus types 2 and 5, both of which bind CAR, show considerable sequence variation on the knob surface, but the residues lining the depression and valleys are conserved.

Each adenovirus fiber is fixed to a 400 kD protein pentamer, the penton base, located at the vertex of the icosahedral virus capsid. Whereas adenovirus attachment to most cells is mediated by the fiber, virus internalization is facilitated by interaction between an RGD recognition sequence within the penton base protein and $\alpha_v$ integrins on the cell surface (Wickham, T. J., et al. (1993). Cell 73, 309–319). Interaction between the penton base RGD and another integrin. $\alpha_M\beta_2$, has recently been shown to promote adenovirus attachment to monocytic cells by a fiber-independent pathway, although virus entry into these cells also depends on a separate interaction with $\alpha_v$ integrins (Huang, S., et al. (1996). J. Virology 70, 4502–4508). CAR expression on CHO cells enhanced adenovirus-mediated gene transfer 100-fold, indicating that virus attachment to CAR protein is followed by virus entry. Once fiber-mediated virus attachment to CAR protein has occurred, internalization may involve a second interaction with $\alpha_v$ integrins or other molecules endogenously expressed on CHO cells.

Adenoviruses, including types 2 and 5, are known predominantly as respiratory pathogens, and are believed to replicate in the epithelium of the upper respiratory tract (Horwitz, M. S. (1996). Adenoviruses. In Virology, B. N. Fields, D. M. Knipe and P. M. Howley, eds. (Philadelphia: Lippincott-Raven), 3rd edition, pp. 2149–2171). Low levels of CAR mRNA were detectable in lung tissue, and both mRNA and protein are expressed in transformed epithelial cell lines such as HeLa. Consistent with the high levels of CAR mRNA expression in myocardium, adenoviruses have recently been recognized as important agents in viral myocarditis (Martin, A. B., et al. (1994). Circulation 90, 330–339). However, adenovirus infections of the pancreas (Niemann, T. H., et al. (1993). Human Pathology 24, 1145–1148), and brain (Kelsey, D. S. (1978). Pediatrics 61, 291–293), two other sites where CAR mRNA is highly expressed, are uncommon. It seems likely that additional factors, including the route of inoculation, delivery to tissues from a primary site of replication, or post-attachment restrictions to virus replication (including the expression of certain integrins), may be important in determining the pattern of illness caused by adenoviruses.

Human adenoviruses can enter a variety of non-human cells, and adenovirus vectors are widely used for gene transfer into experimental animals. Expression of human CAR protein greatly enhanced the efficiency of gene transfer into CHO cells. However, when CFIO cells were exposed to virus at high multiplicity, low levels of transfer were observed even in the absence of CAR. This is consistent with the results of earlier experiments, in which delayed replication of adenovirus DNA was detected in CHO cells exposed to virus at high multiplicity (Longiaru, M. and Horwitz, M. S. (1981). Molecular and Cellular Biology 1, 208–215).

Adenoviruses have generated considerable interest as potential vectors for genetic therapy (Kremer, E. J. and Perricaudet, M. (1995). British Medical Bulletin 51, 31–44). The defective vectors in present use, like the Ad.CMV-βgal used in these studies, are derived from adenovirus 5 and will bind to CAR. Identification of the adenovirus receptor, and an understanding of its tissue distribution, can be important in targeting gene delivery to specific tissues. Manipulation of receptor expression can be used in achieving efficient adenovirus-mediated transduction both in vivo and in vitro. It is remarkable that two viruses so structurally disparate as adenovirus and coxsackievirus have evolved to use the same receptor protein. Identification of CAR as the functional receptor for coxsackie B viruses and adenoviruses can also facilitate development of new strategies to limit infection by these pathogens.

I. Isolated Nucleic Acid Molecules

One aspect of the invention pertains to isolated nucleic acid molecules that encode CAR or biologically active portions thereof, as well as nucleic acid fragments sufficient for use as hybridization probes to identify CAR-encoding nucleic acid (e.g., CAR mRNA). As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated CAR nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a brain cell). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having the nucleotide sequence of SEQ ID NO: 1, or the nucleic acid sequence of the DNA insert of the plasmid deposited with the EMBL Accession Number Y07593, or SEQ ID NO:3, or a portion thereof can be isolated using standard molecular biology techniques and the sequence information provided herein. For example, a human CAR cDNA can be isolated from a human heart or pancreas library using all or portion of SEQ ID NO: 1, or the nucleic acid sequence of the DNA insert of the plasmid deposited with the EMBL Accession Number Y07593, or SEQ ID NO:3 as a hybridization probe and standard hybridization techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989). Moreover, a nucleic acid molecule encompassing all or a portion of SEQ ID NO:1, or the nucleic acid sequence of the DNA insert of the plasmid deposited with the EMBL Accession Number Y07593, or SEQ ID NO:3 can be isolated by the polymerase chain reaction using oligonucleotide primers designed based upon the sequence of SEQ ID NO:1, or the nucleic acid sequence of the DNA insert of the plasmid deposited with the EMBL Accession Number Y07593, or SEQ ID NO:3. For example, mRNA can be isolated from normal heart or pancreas cells (e.g., by the guanidinium-thiocyanate extraction procedure of Chirgwin et al. (1979) *Biochemistry* 18: 5294–5299) and cDNA can be prepared using reverse transcriptase (e.g., Moloney MLV reverse transcriptase, available from Gibco/BRL Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NO:1, or the nucleic acid sequence of the DNA insert of the plasmid deposited with the EMBL Accession Number Y07593, or SEQ ID NO:3. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a CAR nucleotide sequence can be prepared by standard synthetic techniques, e.g., using an automated DNA synthesizer.

In a preferred embodiment, an isolated nucleic acid molecule of the invention comprises the nucleotide sequence shown in SEQ ID NO:1, or the nucleic acid sequence of the DNA insert of the plasmid deposited with the EMBL Accession Number Y07593, or SEQ ID NO:3. The sequence of SEQ ID NO:1, or the nucleic acid sequence of the DNA insert of the plasmid deposited with the EMBL Accession Number Y07593, or SEQ ID NO:3 corresponds to the human CAR cDNA. This cDNA comprises sequences encoding the CAR protein (i.e., "the coding region", from nucleotides 1 to 1157 as indicated in FIG. 13).

In another preferred embodiment, an isolated nucleic acid molecule of the invention comprises a nucleic acid molecule which is a complement of the nucleotide sequence shown in SEQ ID NO:1, or the nucleic acid sequence of the DNA insert of the plasmid deposited with the EMBL Accession Number Y07593, or SEQ ID NO:3 or a portion of either of this nucleotide sequence. A nucleic acid molecule which is complementary to the nucleotide sequence shown in SEQ ID NO:1, or the nucleic acid sequence of the DNA insert of the plasmid deposited with the EMBL Accession Number Y07593, or SEQ ID NO:3 is one which is sufficiently complementary to the nucleotide sequence shown in SEQ ID NO:1, or the nucleic acid sequence of the DNA insert of the plasmid deposited with the EMBL Accession Number Y07593, or SEQ ID NO:3 such that it can hybridize to the nucleotide sequence shown in SEQ ID NO:1, or the nucleic acid sequence of the DNA insert of the plasmid deposited with the EMBL. Accession Number Y07593, or SEQ ID NO:3, thereby forming a stable duplex.

In still another preferred embodiment, an isolated nucleic acid molecule of the invention comprises a nucleotide sequence which is at least about 50–60%, preferably at least about 70–80%, more preferably at least about 90–92%, and even more preferably at least about 94–96%, and even more preferably at least about 98–99% or more homologous to the nucleotide sequence shown in SEQ ID) NO:1, or the nucleic acid sequence of the DNA insert of the plasmid deposited with the EMBL Accession Number Y07593, or SEQ ID NO:3 or a portion of this nucleotide sequence. In an additional preferred embodiment, an isolated nucleic acid molecule of the invention comprises a nucleotide sequence which hybridizes, e.g., hybridizes under stringent conditions, to the nucleotide sequence shown in SEQ ID NO:1, or the nucleic acid sequence of the DNA insert of the plasmid deposited with the EMBL Accession Number Y07593, or SEQ ID NO:3 or a portion of this nucleotide sequence.

Moreover, the nucleic acid molecule of the invention can comprise only a portion of the coding region of SEQ ID NO:1, or the nucleic acid sequence of the DNA insert of the plasmid deposited with the EMBL Accession Number Y07593, or SEQ ID NO:3, for example a fragment which can be used as a probe or primer or a fragment encoding a biologically active portion of CAR. The nucleotide sequence determined from the cloning of the CAR gene allows for the generation of probes and primers designed for use in identifying and/or cloning CAR homologues in other cell types, e.g. from other tissues, as well as CAR homologues from other mammals. The probe/primer typically comprises substantially purified oligonucleotide. The oligonucleotide typically comprises a region of nucleotide sequence that hybridizes under stringent conditions to at least about 12, preferably about 25, more preferably about 40, 50 or 75 consecutive nucleotides of SEQ ID NO:1, or the nucleic acid sequence of the DNA insert of the plasmid deposited with the EMBL Accession Number Y07593, or SEQ ID NO:3 sense, an anti-sense sequence of SEQ ID NO:1, or the nucleic acid sequence of the DNA insert of the plasmid deposited with the EMBL Accession Number Y07593, or SEQ ID NO:3, or naturally occurring mutants thereof. Primers based on the nucleotide sequence in SEQ ID NO:1, or the nucleic acid sequence of the DNA insert of the plasmid deposited with the EMBL Accession Number Y07593, or SEQ ID NO:3 can be used in PCR reactions to clone CAR homologues. Probes based on the CAR nucleotide sequences can be used to detect transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. Such probes can be used as a part of a diagnostic test kit for identifying cells or tissue which misexpress a CAR protein, such as by measuring a level of an CAR-encoding nucleic acid in a sample of cells from a subject e.g., detecting CAR mRNA levels or determining whether a genomic CAR gene has been mutated or deleted.

In one embodiment, the nucleic acid molecule of the invention encodes a protein or portion thereof which includes an amino acid sequence which is sufficiently homologous to an amino acid sequence of SEQ ID NO:2 such that the protein or portion thereof maintains the ability to bind to coxsackievirus, preferably coxsackie B virus, adenovirus, or both the coxsackievirus and adenovirus. As used herein, the language "sufficiently homologous" refers to proteins or portions thereof which have amino acid sequences which include a minimum number of identical or equivalent (e.g., an amino acid residue which has a similar side chain as an amino acid residue in SEQ ID NO:2 amino acid residues to an amino acid sequence of SEQ ID NO:2 or an amino acid sequence encoded by the nucleotide sequence of SEQ ID NO:1, or the nucleic acid sequence of the DNA insert of the plasmid deposited with the EMBL Accession Number Y07593, or SEQ ID NO:3 such that the protein or portion thereof is able to serve as an attachment receptor for the coxsackievirus, adenovirus, or both coxsackievirus and adenovirus. The term "serve as an attachment receptor" as used herein refers to facilitating viral infection or entry.

Portions of proteins encoded by the CAR nucleic acid molecule of the invention are preferably biologically active portions of the CAR protein. As used herein, the term "biologically active portion of CAR" is intended to include a portion, e.g., a domain/motif, of CAR that has one or more of the following activities: 1) it can serve as an attachment receptor for coxsackievirus, adenovirus, or both coxsackievirus (preferably coxsackie B virus) and adenovirus; 2) it can modulate the activity of coxsackievirus, adenovirus, or both coxsackievirus (preferably coxsackie B virus) and adenovirus; and 3) it can modulate the attachment process of coxsackievirus, adenovirus, or both coxsackievirus (preferably coxsackie B virus) and adenovirus in a cell that is responsive to such pathogens (i.e., is capable of attachment to the coxsackievirus or adenovirus), for example, to beneficially down- or up-regulate the responsive cell. Standard binding assays, e.g., radiolabeled assays and competition binding assays as described herein, can be performed to determine the ability of a CAR protein or a biologically active portion thereof to interact with (e.g., bind to) a coxsackievirus or adenovirus. For example, a cell such as a CHO dhfr⁻ hamster cell, can be cotransfected with a nucleic acid encoding the CAR protein or biologically active portion thereof and with a selection marker such as cDNA encoding dihydrofolate reductase. CHO cells can then be exposed to radiolabeled coxsackievirus or radiolabeled adenovirus. After exposure of the cells, attachment can be determined and compared to nonexposed control cells. In addition, inhibition of binding can be measured by preincubating the cells with antibodies raised against the CAR proteins or biologically active fragments thereof.

The invention further encompasses nucleic acid molecules that differ from the nucleotide sequence shown in SEQ ID NO:1, or the nucleic acid sequence of the DNA insert of the plasmid deposited with the EMBL Accession Number Y07593, or SEQ ID NO:3 (and portions thereof) due to degeneracy of the genetic code and thus encode the same CAR protein as that encoded by the nucleotide sequence shown in SEQ ID NO:1, or the nucleic acid sequence of the DNA insert of the plasmid deposited with the EMBL Accession Number Y07593, or SEQ ID NO:3. In another embodiment, an isolated nucleic acid molecule of the invention has a nucleotide sequence encoding a protein having an amino acid sequence shown in SEQ ID NO:2. In a still further embodiment, the nucleic acid molecule of the invention encodes a full length human protein which is substantially homologous to the amino acid sequence of SEQ ID NO:2.

In addition to the human CAR nucleotide sequence shown in SEQ ID NO:1 and the mouse CAR nucleotide sequence shown in SEQ ID NO:3, it will be appreciated by those skilled in the art that DNA sequence polymorphisms that lead to changes in the amino acid sequences of CAR may exist within a population (e.g., the human population). Such genetic polymorphism in the CAR gene may exist among individuals within a population due to natural allelic variation. As used herein, the terms "gene" and "recombinant gene" refer to nucleic acid molecules comprising an open reading frame encoding a CAR protein, preferably a mammalian CAR protein. Such natural allelic variations can typically result in 1–5% variance in the nucleotide sequence of the CAR gene. Any and all such nucleotide variations and resulting amino acid polymorphisms in CAR that are the result of natural allelic variation and that do not alter the functional activity of CAR are intended to be within the scope of the invention. Moreover, nucleic acid molecules encoding CAR proteins from other species, and thus which have a nucleotide sequence which differs from the human sequence of SEQ ID NO:1, or the nucleic acid sequence of the DNA insert of the plasmid deposited with the EMBL Accession Number Y07593, or SEQ ID NO:3, are intended to be within the scope of the invention. Nucleic acid molecules corresponding to natural allelic variants and non-human homologues of the human or mouse CAR cDNA of the invention can be isolated based on their homology to the human or mouse CAR nucleic acid disclosed herein using the human or mouse cDNA, or a portion thereof, as a hybridization probe according to standard hybridization techniques under stringent hybridization conditions. Accordingly, in another embodiment, an isolated nucleic acid molecule of the invention is at least 285 nucleotides in length and hybridizes under stringent conditions to the nucleic acid molecule comprising the nucleotide sequence of SEQ ID NO:1, or the nucleic acid sequence of the DNA insert of the plasmid deposited with the EMBL Accession Number Y07593, or SEQ ID NO:3. In other embodiments, the nucleic acid is at least 300, 350, 400, 450, 500, 550, 600 650, 700, 750, 800, 850, 900, 950, 1000 or more nucleotides in length. As used herein, the term "hybridizes under stringent conditions" is intended to describe conditions for hybridization and washing under which nucleotide sequences at least 50% homologous to each other typically remain hybridized to each other. Preferably, the conditions are such that sequences at least about 60%, more preferably at least about 70%, and even more preferably at least about 75% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6×sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to the sequence of SEQ ID NO:1, or the nucleic acid sequence of the DNA insert of the plasmid deposited with the EMBL Accession Number Y07593, or SEQ ID NO:3 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural human CAR.

In addition to naturally-occurring allelic variants of the CAR sequence that may exist in the population, the skilled artisan will further appreciate that changes can be introduced by mutation into the nucleotide sequence of SEQ ID NO:1, or the nucleic acid sequence of the DNA insert of the plasmid deposited with the EMBL Accession Number Y07593, or SEQ ID NO:3, thereby leading to changes in the amino acid sequence of the encoded CAR protein, without altering the functional ability of the CAR protein. For example, nucleotide substitutions leading to amino acid substitutions at "non-essential" amino acid residues can be made in the sequence of SEQ ID NO:1, or the nucleic acid sequence of the DNA insert of the plasmid deposited with the EMBL Accession Number Y07593, or SEQ ID NO:3. A "non-essential" amino acid residue is a residue that can be altered from the wild-type sequence of CAR (e.g., the sequence of SEQ ID NO:2 without altering the activity of CAR, whereas an "essential" amino acid residue is required for CAR activity.

Accordingly, another aspect of the invention pertains to nucleic acid molecules encoding CAR proteins that contain changes in amino acid residues that are not essential for CAR activity. Such CAR proteins differ in amino acid sequence from SEQ ID NO:2 yet retain at least one of the CAR activities described herein. In one embodiment, the isolated nucleic acid molecule comprises a nucleotide sequence encoding a protein, wherein the protein comprises an amino acid sequence at least about 50% homologous to the amino acid sequence of SEQ ID NO:2 and is capable of binding to the coxsackievirus or adenovirus. Preferably, the protein encoded by the nucleic acid molecule is at least about 60% homologous to SEQ ID NO:2, more preferably at least about 70–80% homologous to SEQ ID NO:2, even more preferably at least about 90% homologous to SEQ ID NO:2, and most preferably at least about 95–99% homologous to SEQ ID NO:2.

To determine the percent homology of two amino acid sequences (e.g., SEQ ID NO:2 and a mutant form thereof) or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence (e.g., SEQ ID NO:2) is occupied by the same amino acid residue or nucleotide as the corresponding position in the other sequence (e.g., a mutant form of CAR), then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions×100).

An isolated nucleic acid molecule encoding a CAR protein homologous to the protein of SEQ ID NO:2 can be created by introducing one or more nucleotide substitutions, additions or deletions into the nucleotide sequence of SEQ ID NO:1, or the nucleic acid sequence of the DNA insert of the plasmid deposited with the EMBL Accession Number Y07593, or SEQ ID NO:3 such that one or more amino acid substitutions, additions or deletions are introduced into the encoded protein. Mutations can be introduced into SEQ ID NO:1, or the nucleic acid sequence of the DNA insert of the plasmid deposited with the EMBL Accession Number Y07593, or SEQ ID NO:3 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arglinine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in CAR is preferably replaced with another amino acid residue from the same side chain family. Alternatively, in another embodiment, mutations can be introduced randomly along all or part of a CAR coding sequence, such as by saturation mutagenesis, and the resultant mutants can be screened for a CAR activity described herein to identify mutants that retain CAR activity. Following mutagenesis of SEQ ID NO:1, or the nucleic acid sequence of the DNA insert of the plasmid deposited with the EMBL Accession Number Y07593, or SEQ ID NO:3, the encoded protein can be expressed recombinantly as described herein and the activity of the protein can be determined using, for example, assays described herein.

In addition to the nucleic acid molecules encoding CAR proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire CAR coding strand, or to only a portion thereof. In one embodiment, an antisense nucleic acid molecule is antisense to a "coding region" of the coding strand of a nucleotide sequence encoding CAR. The term "coding region" refers to the region of the nucleotide sequence comprising codons which are translated into amino acid residues (e.g., the entire coding region of SEQ ID NO:1, or the nucleic acid sequence of the DNA insert of the plasmid deposited with the EMBL Accession Number Y07593, or SEQ ID NO:3, as shown in FIG. 3). In another embodiment, the antisense nucleic acid molecule is antisense to a "noncoding region" of the coding strand of a nucleotide sequence encoding CAR. The term "noncoding region" refers to 5' and 3' sequences which flank the coding region that are not translated into amino acids (i.e., also referred to as 5' and 3' untranslated regions).

Given the coding strand sequences encoding CAR disclosed herein (e.g., SlEQ ID NO:1, or the nucleic acid sequence of the DNA insert of the plasmid deposited with the EMBL Accession Number Y07593, or SEQ ID NO:3), antisense nucleic acids of the invention can be designed according to the rules of Watson and Crick base pairing. The antisense nucleic acid molecule can be complementary to the entire coding region of CAR mRNA, but more preferably is an oligonucleotide which is antisense to only a portion of the coding or noncoding region of CAR mRNA. For example, the antisense oligonucleotide can be complementary to the region surrounding the translation start site of CAR mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a CAR protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of an antisense nucleic acid molecule of the invention includes direct injection at a tissue site. Alternatively, an antisense nucleic acid molecule can be modified to target selected cells and then administered systemically. For example, for systemic administration, an antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave CAR mRNA transcripts to thereby inhibit translation of CAR mRNA. A ribozyme having specificity for an CAR-encoding nucleic acid can be designed based upon the nucleotide sequence of a CAR cDNA disclosed herein (i.e., SEQ ID NO:1, or the nucleic acid sequence of the DNA insert of the plasmid deposited with the EMBL Accession Number Y07593, or SEQ ID NO:3). For example, a derivative of a Tetrahymena L-19 IVS RNA can be constructed in which the nucleotide sequence of the active site is complementary to the nucleotide sequence to be cleaved in an CAR-encoding mRNA. See, e.g., Cech et al. U.S. Pat. No. 4,987,071 and Cech et al. U.S. Pat. No. 5,116,742. Alternatively, CAR mRNA can be used to select a catalytic RNA having a specific ribonuclease activity from a pool of RNA molecules. See, e.g., Bartel, D. and Szostak, J. W. (1993) *Science* 261:1411–1418.

Alternatively, CAR gene expression can be inhibited by targeting nucleotide sequences complementary to the regulatory region of the CAR (e.g., the CAR promoter and/or enhancers) to form triple helical structures that prevent transcription of the CAR gene in target cells. See generally, Helene, C. (1991) *Anticancer Drug Des.* 6(6):569–84; Helene, C. et al. (1992) *Ann. N.Y. Acad. Sci.* 660:27–36; and Maher, L. J. (1992) *Bioassays* 14(12):807–15.

II. Recombinant Expression Vectors and Host Cells

Another aspect of the invention pertains to vectors, preferably expression vectors, containing a nucleic acid encoding CAR (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucicic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., CAR proteins, mutant forms of CAR, fusion proteins, etc.).

The recombinant expression vectors of the invention can be designed for expression of CAR in prokaryotic or eukaryotic cells. For example, CAR can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the CAR is cloned into a pGEX expression vector to create a vector encoding a fusion protein comprising, from the N-terminus to the C-terminus, GST-thrombin cleavage site-CAR. The fusion protein can be purified by affinity chromatography using glutathione-agarose resin. Recombinant CAR unfused to GST can be recovered by cleavage of the fusion protein with thrombin.

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111–2118). Such alteration of nucleic acid sequences of the invention can be carried out by standard DNA synthesis techniques.

In another embodiment, the CAR expression vector is a yeast expression vector. Examples of vectors for expression in yeast *S. cerivisae* include pYepSec1 (Baldari, et al., (1987) *Embo J*. 6:229–234), pMFa (Kurjan and Herskowitz, (1982) *Cell* 30:933–943), pJRY88 (Schultz et al., (1987) *Gene* 54:113–123), and pYES2 (Invitrogen Corporation, San Diego, Calif.).

Alternatively, CAR can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J*. 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis. T. *Molecular Cloning: A Laboratory Manual. 2nd, ed.,* Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43 :235–275), in particular promoters of T cell receptors (Winoto and Baltimore (1989) *EMBO J*. 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *PNAS* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to CAR mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, CAR protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed, Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding CAR or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) CAR protein. Accordingly, the invention further provides methods for producing CAR protein using the host cells of the invention. In one embodiment, the method comprises culturing the host cell of invention (into which a recombinant expression vector encoding CAR has been introduced) in a suitable medium until CAR is produced. In another embodiment, the method further comprises isolating CAR from the medium or the host cell.

The host cells of the invention can also be used to produce nonhuman transgenic animals. The nonhuman transgenic animals can be used in screening assays designed to identify agents or compounds, e.g., drugs, pharmaceuticals, etc., which are capable of ameliorating detrimental symptoms of selected disorders such as cardiovascular disorders and proliferative disorders. For example, in one embodiment, a host cell of the invention is a fertilized oocyte or an embryonic stem cell into which CAR-coding sequences have been introduced. Such host cells can then be used to create non-human transgenic animals in which exogenous CAR sequences have been introduced into their genome or homologous recombinant animals in which endogenous CAR sequences have been altered. Such animals are useful for studying the function and/or activity of CAR and for identifying and/or evaluating modulators of CAR activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous CAR gene has been altered by homologous recombination between the endogenous gene and an exogenous DNA molecule introduced into a cell of the animal, e.g., an embryonic cell of the animal, prior to development of the animal.

A transgenic animal of the invention can be created by introducing CAR-encoding, nucleic acid into the male pronuclei of a fertilized oocyte, e.g., by microinjection, retroviral infection, and allowing the oocyte to develop in a pseudopregnant female foster animal. The human CAR cDNA sequence of SEQ ID NO:1, or the nucleic acid sequence of the DNA insert of the plasmid deposited with the EMBL Accession Number Y07593, or SEQ ID NO:3 can be introduced as a transgene into the genome of a nonhuman animal. Alternatively, a nonhuman homologue of the human CAR gene, such as a mouse CAR gene, can be isolated based on hybridization to the human CAR cDNA (described further in subsection I above) and used as a transgene. Intronic sequences and polyadenylation signals can also be included in the transgene to increase the efficiency of expression of the transgene. A tissue-specific regulatory sequence(s) can be operably linked to the CAR transgene to direct expression of CAR protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the CAR transgene in its genome and/or expression of CAR mRNA in tissues or cells of the animals. A transgenic founder animal can then be used to breed additional animals carrying the transgene. Moreover, transgenic animals carrying a transgene encoding CAR can further be bred to other transgenic animals carrying other transgenes.

To create a homologous recombinant animal, a vector is prepared which contains at least a portion of a CAR gene into which a deletion, addition or substitution has been introduced to thereby alter, e.g., functionally disrupt, the CAR gene. The CAR gene can be a human gene (e.g., from a human genomic clone isolated from a human genomic library screened with the cDNA of SEQ ID NO:1, or the nucleic acid sequence of the DNA insert of the plasmid deposited with the EMBL Accession Number Y07593, or SEQ ID NO:3), but more preferably, is a nonhuman homologue of a human CAR gene. For example, a mouse CAR gene can be isolated from a mouse genomic DNA library using the human CAR cDNA of SEQ ID NO:1, or the nucleic acid sequence of the DNA insert of the plasmid deposited with the EMBL Accession Number Y07593, or SEQ ID NO:3 as a probe. The mouse CAR gene then can be used to construct a homologous recombination vector suitable for altering an endogenous CAR gene in the mouse genome. In a preferred embodiment, the vector is designed such that, upon homologous recombination, the endogenous CAR gene is functionally disrupted (i.e., no longer encodes a functional protein; also referred to as a "knock out" vector). Alternatively, the vector can be designed such that, upon homologous recombination, the endogenous CAR gene is mutated or otherwise altered but still encodes functional protein (e.g., the upstream regulatory region can be altered to thereby alter the expression of the endogenous CAR protein). In the homologous recombination vector, the altered portion of the CAR gene is flanked at its 5' and 3' ends by additional nucleic acid of the CAR gene to allow for homologous recombination to occur between the exogenous CAR gene carried by the vector and an endogenous CAR gene in an embryonic stem cell. The additional flanking CAR nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced CAR gene has homologously recombined with the endogenous CAR gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic nonhumans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *PNAS* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut, I. et al. (1997) *Nature* 385:810–813. In brief, a cell, e.g., a somatic cell, from the transgenic animal can be isolated and induced to exit the growth cycle and enter $G_o$ phase. The quiescent cell can then be used, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring borne of this female foster animal will be a clone of the animal from which the cell, e.g., the somatic cell, is isolated.

III. Isolated CAR Proteins and Anti-CAR Antibodies

Another aspect of the invention pertains to isolated CAR proteins, and biologically active portions thereof, as well as peptide fragments suitable for use as immunogens to raise anti-CAR antibodies. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of CAR protein in which the protein is separated from cellular components of the cells in which it is naturally or recombinantly produced. In one embodiment, the language "substantially free of cellular material" includes preparations of CAR protein having less than about 30% (by dry weight) of non-CAR protein (also referred to herein as a "contaminating protein"), more preferably less than about 20% of non-CAR protein, still more preferably less than about 10% of non-CAR protein, and most preferably less than about 5% non-CAR protein. When the CAR protein or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of CAR protein in which the protein is separated from chemical precursors or other chemicals which are involved in the synthesis of the protein. In one embodiment, the language "substantially free of chemical precursors or other chemicals" includes preparations of CAR protein having less than about 30% (by dry weight) of chemical precursors or non-CAR chemicals, more preferably less than about 20% chemical precursors or non-CAR chemicals, still more preferably less than about 10% chemical precursors or non-CAR chemicals, and most preferably less than about 5% chemical precursors or non-CAR chemicals. In preferred embodiments, isolated proteins or biologically active portions thereof lack contaminating proteins from the same animal from which the CAR protein is derived. Typically, such proteins are produced by recombinant expression of, for example, a human CAR protein in a nonhuman cell.

An isolated CAR protein or a portion thereof of the invention can bind to the coxsackie B virus and adenovirus. In preferred embodiments, the protein or portion thereof comprises an amino acid sequence which is sufficiently homologous to an amino acid sequence of SEQ ID NO:2 such that the protein or portion thereof maintains the bind to the coxsackie B virus and adenovirus. The portion of the protein is preferably a biologically active portion as described herein. In another preferred embodiment, the CAR protein (i.e., amino acid residues 1–365) has an amino acid sequence shown in SEQ ID NO:2 or an amino acid sequence which is encoded by the nucleotide sequence of SEQ ID NO:1, or the nucleic acid sequence of the DNA insert of the plasmid deposited with the EMBL Accession Number Y07593, or SEQ ID NO:3. In yet another preferred embodiment, the CAR protein has an amino acid sequence which is encoded by a nucleotide sequence which hybridizes, e.g., hybridizes under stringent conditions, to the nucleotide sequence of SEQ ID NO:1, or the nucleic acid sequence of the DNA insert of the plasmid deposited with the EMBL Accession Number Y07593, or SEQ ID NO:3. In still another preferred embodiment, the CAR protein has an amino acid sequence which is encoded by a nucleotide sequence that is at least about 50–66%, preferably at least about 60–70%, more preferably at least about 80–90%, more preferably at least about 90–92%, more preferably at least about 94–96%, and even more preferably at least about 98–99% or more homologous to the nucleotide sequence of SEQ ID NO:1, or the nucleic acid sequence of the DNA insert of the plasmid deposited with the EMBL Accession Number Y07593, or SEQ ID NO:3. The preferred CAR proteins of the present invention also preferably possess at least one of the CAR activities described herein. For example, a preferred CAR protein of the present invention includes an amino acid sequence encoded by a nucleotide sequence which hybridizes, e.g., hybridizes under stringent conditions, to the nucleotide sequence of SEQ ID NO:1, or the nucleic acid sequence of the DNA insert of the plasmid deposited with the EMBL Accession Number Y07593, or SEQ ID NO:3 and which can bind to the coxsackie B virus or adenovirus.

In other embodiments, the CAR protein is substantially homologous to the amino acid sequence of SEQ ID NO:2 and retains the functional activity of the protein of SEQ ID NO:2 yet differs in amino acid sequence due to natural allelic variation or mutagenesis. as described in detail in subsection I above. Accordingly, in another embodiment, the CAR protein is a protein which comprises an amino acid sequence which is at least about 50–60%, preferably at least about 70–80%, and more preferably at least about 86, 88, 90%, and most preferably at least about 90–95% or more homologous to the entire amino acid sequence of SEQ ID NO:2 and which has at least one of the CAR activities described herein. In other embodiments, the invention pertains to a full length human protein which is substantially homologous to the entire amino acid sequence of SEQ ID NO:2.

Biologically active portions of the CAR protein include peptides comprising amino acid sequences derived from the amino acid sequence of the CAR protein, e.g., the amino acid sequence shown in SEQ ID NO:2 or the amino acid sequence of a protein homologous to the CAR protein, which include less amino acids than the full length CAR protein or the full length protein which is homologous to the CAR protein, and exhibit at least one activity of the CAR protein. Typically, biologically active portions (peptides, e.g., peptides which are, for example, 5, 10, 15, 20, 30, 35, 36, 37, 38, 39, 40, 50, 100 or more amino acids in length) comprise a domain with at least one activity of the CAR protein. Preferably, the domain is derived from a human and is at least about 55%, preferably at least about 60–65%, even more preferably at least about 70–75%, and most preferably at least about 80–90% or more homologous to SEQ ID NO:2. In a preferred embodiment, the biologically active portion of the protein can bind to coxsackievirus, adenovirus, or both coxsackievirus (preferably coxsackie B virus) and adenovirus. In another embodiment, the biologically active portion facilitates virus entry into a cell. Moreover, other biologically active portions, in which other regions of the protein are deleted, can be prepared by recombinant techniques and evaluated for one or more of the activities described herein.

CAR proteins are preferably produced by recombinant DNA techniques. For example, a nucleic acid molecule encoding the protein is cloned into an expression vector (as described above), the expression vector is introduced into a host cell (as described above) and the CAR protein is expressed in the host cell. The CAR protein can then be isolated from the cells by an appropriate purification scheme using standard protein purification techniques. Alternative to recombinant expression, a CAR protein, polypeptide, or peptide can be synthesized chemically using standard peptide synthesis techniques. Moreover, native CAR protein can be isolated from cells (e.g., brain cells), for example using an anti-CAR antibody (described further below).

The invention also provides CAR chimeric or fusion proteins. As used herein, a CAR "chimeric protein" or "fusion protein" comprises a CAR polypeptide operatively linked to a non-CAR polypeptide. An "CAR polypeptide" refers to a polypeptide having an amino acid sequence corresponding to CAR, whereas a "non-CAR polypeptide" refers to a polypeptide having an amino acid sequence corresponding to a protein which is not substantially homologous to the CAR protein, e.g., a protein which is different from the CAR protein and which is derived from the same or a different organism. Within the fusion protein, the term "operatively linked" is intended to indicate that the CAR polypeptide and the non-CAR polypeptide are fused in-frame to each other. The non-CAR polypeptide can be fused to the N-terminus or C-terminus of the CAR polypeptide. For example, in one embodiment the fusion protein is a GST-CAR fusion protein in which the CAR sequences are fused to the C-terminus of the GST sequences. Such fusion proteins can facilitate the purification of recombinant CAR. In another embodiment, the fusion protein is a CAR protein containing a heterologous signal sequence at its N-terminus.

In certain host cells (e.g., mammalian host cells), expression and/or secretion of CAR can be increased through use of a heterologous signal sequence.

Preferably, a CAR chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). An CAR-encoding nucleic acid can be cloned into such an expression vector such that the fusion moiety is linked in-frame to the CAR protein.

The present invention also pertains to homologues of the CAR proteins which function as either a CAR agonist (mimetic) or a CAR antagonist. In a preferred embodiment, the CAR agonists and antagonists stimulate or inhibit, respectively, a subset of the biological activities of the naturally occurring form of the CAR protein. Thus, specific biological effects can be elicited by treatment with a homologue of limited function. In one embodiment, treatment of a subject with a homologue having a subset of the biological activities of the naturally occurring form of the protein has fewer side effects in a subject relative to treatment with the naturally occurring form of the CAR protein.

Homologues of the CAR protein can be generated by mutagenesis, e.g., discrete point mutation or truncation of the CAR protein. As used herein, the term "homologue" refers to a variant form of the CAR protein which acts as an agonist or antagonist of the activity of the CAR protein. An agonist of the CAR protein can retain substantially the same, or a subset, of the biological activities of the CAR protein. An antagonist of the CAR protein can inhibit one or more of the activities of the naturally occurring form of the CAR protein, by, for example, competitively binding to a downstream or upstream member of the CAR cascade which includes the CAR protein. Thus, the mammalian CAR protein and homologues thereof of the present invention can be either positive or negative regulators of the CAR binding to the coxsackie B virus and adenovirus.

In an alternative embodiment, homologues of the CAR protein can be identified by screening combinatorial libraries of mutants, e.g., truncation mutants, of the CAR protein for CAR protein agonist or antagonist activity. In one embodiment, a variegated library of CAR variants is generated by combinatorial mutagenesis at the nucleic acid level and is encoded by a variegated gene library. A variegated library of CAR variants can be produced by, for example, enzymatically ligating a mixture of synthetic oligonucleotides into gene sequences such that a degenerate set of potential CAR sequences is expressible as individual polypeptides, or alternatively, as a set of larger fusion proteins (e.g., for phage display) containing the set of CAR sequences therein. There are a variety of methods which can be used to produce libraries of potential CAR homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential CAR sequences. Methods for synthesizing degenerate oligonucleotides are known in the art (see, e.g., Narang, S. A. (1983) *Tetrahedron* 39:3; Itakura et al. (1984) *Annu. Rev. Biochem*. 53:323; Itakura et al. (1984) *Science* 198:1056; Ike et al. (1983) *Nucleic Acid Res*. 11:477.

In addition libraries of fragments of the CAR protein coding can be used to generate a variegated population of CAR fragments for screening and subsequent selection of homologues of a CAR protein. In one embodiment, a library of coding sequence fragments can be generated by treating a double stranded PCR fragment of a CAR coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the CAR protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of CAR homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique which enhances the frequency of functional mutants in the libraries, can be used in combination with the screening assays to identify CAR homologues (Arkin and Yourvan (1992) *PNAS* 89:7811–7815; Delgrave et al. (1993) *Protein Engineering* 6(3):327–331).

In one embodiment, cell based assays can be exploited to analyze a variegated CAR library. For example, a library of expression vectors can be transfected into a cell line ordinarily capable of binding to the coxsackievirtis or adenovirus. The transfected cells are then contacted with radiolabeled coxsackievirus or adenovirus and the effect of the CAR mutant on binding to the coxsackie B virus and adenovirus can be detected. Plasmid DNA can then be recovered from the cells which score for inhibition, or alternatively, potentiation of binding to the coxsackie B virus and adenovirus, and the individual clones further characterized.

An isolated CAR protein, or a portion or fragment thereof, can be used as an immunogen to generate antibodies that bind CAR using standard techniques for polyclonal and monoclonal antibody preparation. The full-length CAR protein can be used or, alternatively, the invention provides antigenic peptide fragments of CAR for use as immunogens. The antigenic peptide of CAR comprises at least 8 amino acid residues of the amino acid sequence shown in SEQ ID NO:2 and encompasses an epitope of CAR such that an antibody raised against the peptide forms a specific immune complex with CAR. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of CAR that are located on the surface of the protein, e.g., hydrophilic regions.

A CAR immunogen typically is used to prepare antibodies by immunizing a suitable subject, (e.g., rabbit, goat, mouse or other mammal) with the immunogen. An appropriate immunogenic preparation can contain, for example, recombinantly expressed CAR protein or a chemically synthesized CAR peptide. The preparation can further include an adjuvant, such as Freund's complete or incomplete adjuvant, or similar immunostimulatory agent. Immunization of a suitable subject with an immunogenic CAR preparation induces a polyclonal anti-CAR antibody response.

Accordingly, another aspect of the invention pertains to anti-CAR antibodies. The term "antibody" as used herein refers to immunoglobulin molecules and immunologically active portions of immunoglobulin molecules, i.e., molecules that contain an antigen binding site which specifically binds (immunoreacts with) an antigen, such as CAR. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind CAR. The term "monoclonal antibody" or "monoclonal antibody composition", as used herein, refers to a population of antibody molecules that contain only one species of an antigen binding site capable of immunoreacting with a particular epitope of CAR. A monoclonal antibody composition thus typically displays a single binding affinity for a particular CAR protein with which it immunoreacts.

Polyclonal anti-CAR antibodies can be prepared as described above by immunizing a suitable subject with a CAR immunogen. The anti-CAR antibody titer in the immunized subject can be monitored over time by standard techniques, such as with an enzyme linked immunosorbent assay (ELISA) using immobilized CAR. If desired, the antibody molecules directed against CAR can be isolated from the mammal (e.g., from the blood) and further purified by well known techniques, such as protein A chromatography to obtain the IgG fraction. At an appropriate time after immunization, e.g., when the anti-CAR antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *PNAS* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with a CAR immunogen as described above, and the culture supernatants of the resulting hybridoma cells are screened to identify a hybridoma producing a monoclonal antibody that binds CAR.

Any of the many well known protocols used for fusing lymphocytes and immortalized cell lines can be applied for the purpose of generating an anti-CAR monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind CAR, e.g., using a standard ELISA assay.

Alternative to preparing monoclonal antibody-secreting hybridomas, a monoclonal anti-CAR antibody can be identified and isolated by screening a recombinant combinatorial immunoglobulin library (e.g., an antibody phage display library) with CAR to thereby isolate immunoglobulin library members that bind CAR. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technolooy* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734; Hawkins et al. (1992) *J. Mol. Biol.* 226:889–896; Clarkson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc. Acid Res.* 19:4133–4137; Barbas et al. (1991) *PNAS* 88:7978–7982; and McCafferty et al. *Nature* (1990) 348:552–554.

Additionally, recombinant anti-CAR antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171, 496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *PNAS* 84:3439–3443; Liu et al. (1987) *J. Immunol.* 139:3521–3526; Sun et al. (1987) *PNAS* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyan et al. (1988) *Science* 239: 1534; and Beidler et al. (1988) *J. Immunol.* 141:4053–4060.

An anti-CAR antibody (e.g., monoclonal antibody) can be used to isolate CAR by standard techniques, such as affinity chromatography or immunoprecipitation. An anti-CAR antibody can facilitate the purification of natural CAR from cells and of recombinantly produced CAR expressed in host cells. Moreover, an anti-CAR antibody can be used to detect CAR protein (e.g., in a cellular lysate or cell supernatant) in order to evaluate the abundance and pattern of expression of the CAR protein. Anti-CAR antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$ $^{35}S$ or $^{3}H$ IV. Pharmaceutical Compositions The CAR nucleic acid molecules, CAR proteins, CAR modulators, and anti-CAR antibodies (also referred to herein as "active compounds") of the invention can be incorporated into pharmaceutical compositions suitable for administration to a subject, e.g., a human. Such compositions typically comprise the nucleic acid molecule, protein, modulator, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions.

A pharmaceutical composition of the invention is formulated to be compatible with its intended route of administration. Examples of routes of administration include parenteral. e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a CAR protein or anti-CAR antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate. polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) PNAS 91 :3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, modulators, and antibodies described herein can be used in one or more of the following methods: 1) drug screening assays; 2) diagnostic assays; and 3) methods of treatment. A CAR protein of the invention has one or more of the activities described herein and can thus be used to, for example, modulate the attachment mechanism infectivity, or entry of the coxsackievirus or adenovirus to a responsive cell. The isolated nucleic acid molecules of the invention can be used to express CAR protein (e.g., via a recombinant expression vector in a host cell in gene therapy applications), to detect CAR mRNA (e.g., in a biological sample) or a genetic lesion in a CAR gene, and to modulate CAR activity, as described further below. In addition, the CAR proteins can be used to screen drugs or compounds which modulate CAR protein activity as well as to treat disorders characterized by production and expression of CAR protein. Also, the anti-CAR antibodies of the invention can be used to detect and isolate CAR protein and modulate CAR protein activity.

a. Drug Screening Assays:

The invention provides methods for identifying compounds or agents which can be used to treat disorders characterized by (or associated with) CAR nucleic acid expression and/or CAR protein activity. These methods are also referred to herein as drug screening assays and typically include the step of screening a candidate/test compound or agent for the ability to interact with (e.g., bind to) a CAR protein, to modulate the interaction of a CAR protein and a target molecule, and/or to modulate CAR nucleic acid expression and/or CAR protein activity. Candidate/test compounds or agents which have one or more of these abilities can be used as drugs to treat disorders characterized by CAR nucleic acid expression and/or CAR protein activity. Candidate/test compounds such as small molecules, e.g., small organic molecules, and other drug candidates can be obtained, for example, from combinatorial and natural product libraries.

In one embodiment, the invention provides assays for screening candidate/test compounds which interact with (e.g., bind to) CAR protein. Typically, the assays are cell-free assays which include the steps of combining a CAR protein or a biologically active portion thereof, and a candidate/test compound, e.g., under conditions which allow for interaction of (e.g., binding of) the candidate/test compound to the CAR protein or portion thereof to form a complex, and detecting the formation of a complex, in which the ability of the candidate compound to interact with (e.g., bind to) the CAR protein or portion thereof is indicated by the presence of the candidate compound in the complex.

Formation of complexes between the CAR protein and the candidate compound can be quantitated, for example, using standard immunoassays.

In another embodiment, the invention provides screening assays to identify candidate/test compounds which modulate (e.g. stimulate or inhibit) the interaction (and most likely CAR activity as well) between a CAR protein and a molecule (target molecule) with which the CAR protein normally interacts. Examples of such target molecules includes proteins in the same signaling path as the CAR protein, e.g., proteins which may function upstream (including both stimulators and inhibitors of activity) or downstream of the CAR protein. Typically, the assays are cell-free assays which include the steps of combining a CAR protein or a biologically active portion thereof, a CAR target molecule (e.g., a CAR ligand) and a candidate/test compound, e.g., under conditions wherein but for the presence of the candidate compound, the CAR protein or biologically active portion thereof interacts with (e.g., binds to) the target molecule, and detecting the formation of a complex which includes the CAR protein and the target molecule or detecting the interaction/reaction of the CAR protein and the target molecule. Detection of complex formation can include direct quantitation of the complex by, for example, measuring inductive effects of the CAR protein. A statistically significant chance, such as a decrease, in the interaction of the CAR and target molecule (e.g. in the formation of a complex between the CAR and the target molecule) in the presence of a candidate compound (relative to what is detected in the absence of the candidate compound) is indicative of a modulation (e.g., stimulation or inhibition) of the interaction between the CAR protein and the target molecule. Modulation of the formation of complexes between the CAR protein and the target molecule can be quantitated using, for example, an immunoassay.

To perform the above drug screening assays, it is desirable to immobilize either CAR or its target molecule to facilitate separation of complexes from uncomplexed forms of one or both of the proteins, as well as to accommodate automation of the assay. Interaction (e.g., binding of) of CAR to a target molecule, in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows the protein to be bound to a matrix. For example, glutathione-S-transferase/CAR fusion proteins can be adsorbed onto glutathione sepharose beads (Sigma Chemical, St. Louis, Mo.) or glutathione derivatized microtitre plates, which are then combined with the cell lysates (e.g. $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of CAR-binding protein found in the bead fraction quantitated from the gel using standard electrophoretic techniques.

Other techniques for immobilizing proteins on matrices can also be used in the drug, screening assays of the invention. For example. either CAR or its target molecule can be immobilized utilizing conjugation of biotin and streptavidin. Biotinylated CAR molecules can be prepared from biotin-Nf IS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with CAR but which do not interfere with binding of the protein to its target molecule can be derivatized to the wells of the plate, and CAR trapped in the wells by antibody conjugation. As described above, preparations of a CAR-binding protein and a candidate compound are incubated in the CAR-presenting wells of the plate, and the amount of complex trapped in the well can be quantitated. Methods for detecting such complexes, in addition to those described above for the GST-immobilized complexes, include immunodetection of complexes using antibodies reactive with the CAR target molecule, or which are reactive with CAR protein and compete with the target molecule; as well as enzyme-linked assays which rely on detecting an enzymatic activity associated with the target molecule.

In yet another embodiment, the invention provides a method for identifying a compound (e.g., a screening assay) capable of use in the treatment of a disorder characterized by (or associated with) CAR nucleic acid expression or CAR protein activity. This method typically includes the step of assaying the ability of the compound or agent to modulate the expression of the CAR nucleic acid or the activity of the CAR protein thereby identifying a compound for treating a disorder characterized by CAR nucleic acid expression or CAR protein activity. Disorders characterized by CAR nucleic acid expression or CAR protein activity are described herein. Methods for assaying the ability of the compound or agent to modulate the expression of the CAR nucleic acid or activity of the CAR protein are typically cell-based assays. For example, cells can be induced to overexpress a CAR protein in the presence and absence of a candidate compound. Candidate compounds which produce a statistically significant change in CAR-dependent responses (either stimulation or inhibition) can be identified. In one embodiment, expression of the CAR nucleic acid or activity of a CAR protein is modulated in cells and the effects of candidate compounds on the readout of interest (such as rate of cell proliferation or differentiation) are measured. For example, the expression of genes which are up- or down-regulated in response to a CAR-dependent signal cascade can be assayed. In preferred embodiments, radiolabeled coxsackievirus or adenovirus, as well as, competition binding assay, are used for detection and quantitation.

Alternatively, modulators of CAR expression (e.g., compounds which can be used to treat a disorder characterized by CAR nucleic acid expression or CAR protein activity) can be identified in a method wherein a cell is contacted with a candidate compound and the expression of CAR mRNA or protein in the cell is determined. The level of expression of CAR mRNA or protein in the presence of the candidate compound is compared to the level of expression of CAR mRNA or protein in the absence of the candidate compound. The candidate compound can then be identified as a modulator of CAR nucleic acid expression based on this comparison and be used to treat a disorder characterized by CAR nucleic acid expression. For example, when expression of CAR mRNA or protein is greater (statistically significantly greater) in the presence of the candidate compound than in its absence, the candidate compound is identified as a stimulator of CAR mRNA or protein expression. Alternatively, when expression of CAR mRNA or protein is less (statistically significantly less) in the presence of the candidate compound than in its absence, the candidate compound is identified as an inhibitor of CAR mRNA or protein expression. The level of CAR mRNA or protein expression in the cells can be determined by methods described herein for detecting CAR mRNA or protein.

In yet another aspect of the invention, the CAR proteins can be used as "bait proteins" in a two-hybrid assay (see, e.g., U.S. Pat. No. 5,283,317; Servos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO 94/10300), to identify other proteins, which bind to or interact with CAR ("CAR-binding proteins" or "CAR-bp") and modulate CAR protein activity. Such CAR-binding proteins are also likely to be involved in the propagation of signals by the CAR proteins as. for example, upstream or downstream elements of the CAR pathway.

The two-hybrid system is based on the modular nature of most transcription factors, which consist of separable DNA-binding and activation domains. Briefly, the assay utilizes two different DNA constructs. In one construct, the gene that codes for CAR is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo forming an CAR-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with CAR.

Modulators of CAR protein activity and/or CAR nucleic acid expression identified according to these drug screening assays can be used to treat infections affecting. for example, the heart, pancreas, and central nervous system, as well as, the respiratory and gastrointestinal tracts. Examples of other diseases or disorders which could be treated using modulators of CAR protein activity and/or nucleic acid expression are described in Grist, N. R. and Reid, D. (1993). Epidemiology of viral infections of the heart. In Viral Infections of the Heart, J. Banatvala, ed. (London: Edward Arnold), pp. 23–31; Yoon, J. W., et al. (1979). New England Journal of Medicine 300, 1173–79; Woodruff, J. (1980). Am. J. Pathol. 101, 427–479; Nakao, T., (1964). Tohoku Journal of Experimental Medicine 83, 94–102; Lerner, A. M. and Wilson, F. M. (1973). Prog. Med. Virol. 15, 63–91. These methods of treatment include the steps of administering the modulators of CAR protein activity and/or nucleic acid expression, e.g., in a pharmaceutical composition as described in subsection IV above, to a subject in need of such treatment, e.g., a subject with cardiac infection.

b. Diagnostic Assays:

The invention further provides a method for detecting the presence of CAR in a biological sample. The method involves contacting the biological sample with a compound or an agent capable of detecting CAR protein or mRNA such that the presence of CAR is detected in the biological sample. A preferred agent for detecting CAR mRNA is a labeled or labelable nucleic acid probe capable of hybridizing to CAR mRNA. The nucleic acid probe can be, for example, the full-length CAR eDNA of SEQ ID NO:1, or the nucleic acid sequence of the DNA insert of the plasmid deposited with the EMBL Accession Number Y07593, or SEQ ID NO:3, or a portion thereof, such as an oligonucleotide of at least 15, 30, 50, 100, 250 or 500 nucleotides in length and sufficient to specifically hybridize under stringent conditions to CAR mRNA. A preferred agent for detecting CAR protein is a labeled or labelable antibody capable of binding to CAR protein. (See, Hsu, K.-H. L., et al. (1988). J. Virol. 62, 1647–1652). Antibodies can be polyclonal, or more preferably, monoclonal. An intact antibody, or a fragment thereof (e.g., RmcB) can be used. The term "labeled or labelable", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect CAR mRNA or protein in a biological sample in vitro as well as in vivo. For example, in vitro techniques for detection of CAR mRNA include Northern hybridizations and in situ hybridizations. In vitro techniques for detection of CAR protein include enzyme linked immunosorbent assays (ELISAs), Western blots, immunoprecipitations and immunofluorescence. Alternatively, CAR protein can be detected in vivo in a subject by introducing into the subject a labeled anti-CAR antibody. For example, the antibody can be labeled with a radioactive marker whose presence and location in a subject can be detected by standard imaging techniques.

In one preferred embodiment of the detection method, the biological sample is a cardiac cell sample. A tissue section, for example, a freeze-dried or fresh frozen section of tissue removed from a patient, can be used as the cardiac cell sample. Alternatively, the biological sample can comprise a biological fluid obtained from a subject having a cardiac infection.

The invention also encompasses kits for detecting the presence of CAR in a biological sample. For example, the kit can comprise a labeled or labelable compound or agent capable of detecting CAR protein or mRNA in a biological sample; means for determining the amount of CAR in the sample; and means for comparing the amount of CAR in the sample with a standard. The compound or agent can be packaged in a suitable container. The kit can further comprise instructions for using the kit to detect CAR mRNA or protein.

The methods of the invention can also be used to detect genetic lesions in a CAR gene, thereby determining if a subject with the lesioned gene is at risk for a disorder characterized by CAR nucleic acid expression or CAR protein activity as defined herein. In preferred embodiments, the methods include detecting, in a sample of cells from the subject, the presence or absence of a genetic lesion characterized by at least one of an alteration affecting the integrity of a gene encoding a CAR protein, or the misexpression of the CAR gene. For example, such genetic lesions can be detected by ascertaining the existence of at least one of 1) a deletion of one or more nucleotides from a CAR gene; 2) an addition of one or more nucleotides to a CAR gene; 3) a substitution of one or more nucleotides of a CAR gene, 4) a chromosomal rearrangement of a CAR gene; 5) an alteration in the level of a messenger RNA transcript of a CAR gene, 6) aberrant modification of a CAR gene, such as of the methylation pattern of the genomic DNA, 7) the presence of a non-wild type splicing pattern of a messenger RNA transcript of a CAR gene, 8) a non-wild type level of a CAR-protein, 9) allelic loss of a CAR gene, and 10) inappropriate post-translational modification of a CAR-protein. As described herein, there are a large number of assay techniques known in the art which can be used for detecting lesions in a CAR gene.

In certain embodiments, detection of the lesion involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91 :360–364), the latter of which can be particularly useful for detecting point mutations in the CAR-gene (see Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a CAR gene under conditions such that hybridization and amplification of the CAR-gene (if present) occurs, and detecting the presence or absence of an amplification product, or detecting the size of the amplification product and comparing the length to a control sample.

In an alternative embodiment, mutations in a CAR gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In yet another embodiment, any of a variety of sequencing reactions known in the art can be used to directly sequence the CAR gene and detect mutations by comparing the sequence of the sample CAR with the corresponding wild-type (control) sequence. Examples of sequencing reactions include those based on techniques developed by Maxim and Gilbert ((1977) *PNAS* 74:560) or Sanger ((1977) *PNAS* 74:5463). A variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr*, 36:127–162; and Griffin et al. (1993) *Appl. Biochem. Biotechnol.* 38:147–159).

Other methods for detecting mutations in the CAR gene include methods in which protection from cleavage agents is used to detect mismatched bases in RNA/RNA or RNA/DNA duplexes (Myers et al. (1985) *Science* 230:1242); Cotton et al. (1988) *PNAS* 85:4397; Saleeba et al. (1992) *Meth. Enzymol.* 217:286–295), electrophoretic mobility of mutant and wild type nucleic acid is compared (Orita et al. (1989) *PNAS* 86:2766; Cotton (1993) *Mutat Res* 285:125–144; and Hayashi (1992) *Genet Anal Tech Appl* 9:73–79), and movement of mutant or wild-type fragments in polyacrylamide gels containing a gradient of denaturant is assayed using denaturing gradient gel electrophoresis (Myers et al (1985) *Nature* 313 :495). Examples of other techniques for detecting point mutations include, selective oligonucleotide hybridization, selective amplification, and selective primer extension.

c. Methods of Treatment

Another aspect of the invention pertains to methods for treating a subject, e.g., a human, having a disease or disorder characterized by (or associated with) CAR nucleic acid expression and/or CAR protein activity. These methods include the step of administering a CAR modulator to the subject such that treatment occurs. As the CAR protein is involved in the attachment and infectivity or entry of the coxsackievirus and the adenovirus, CAR activity or expression creates an increased risk of infection. Non-limiting examples of disorders or diseases characterized by or associated with CAR activity or expression include infections affecting the heart, pancreas, and central nervous system, as well as, the respiratory and gastrointestinal tracts. Cardiac infections are disorders which detrimentally affect normal cardiovascular function. Examples of cardiac infections include acute viral myocarditis and pericarditis, as well as, dilated cardiomyopathy. Pancreatic and central nervous system infections are disorders which detrimentally affect the normal function of the pancreas and central nervous system, e.g., acute pancreatitis, meningoencephalitis, and non-specific febrile illnesses. Another disorder characterized by or associated with CAR activity or expression includes childhood onset diabetes. Additional methods of the invention include methods for treating a subject having a disorder characterized by CAR activity or expression. These methods include administering to the subject a CAR modulator such that treatment of the subject occurs. The terms "treating" or "treatment", as used herein, refer to reduction or alleviation of at least one adverse effect or symptom of a disease or disorder, e.g., a disease or disorder characterized by or associated with CAR protein activity or CAR nucleic acid expression.

As used herein, a CAR modulator is a molecule which can modulate CAR nucleic acid expression and/or CAR protein activity. For example, a CAR modulator can modulate, e.g., Lip-regulate (activate) or down-regulate (suppress), CAR nucleic acid expression. In another example, a CAR modulator can modulate (e.g., stimulate or inhibit) CAR protein activity. If it is desirable to treat a disease or disorder characterized by (or associated with) CAR nucleic acid expression and/or CAR protein activity by inhibiting CAR nucleic acid expression, a CAR modulator can be an antisense molecule, e.g., a ribozyme, as described herein. Examples of antisense molecules which can be used to inhibit CAR nucleic acid expression include antisense molecules which are complementary to a portion of the 5' untranslated region of SEQ ID NO:1, or the nucleic acid sequence of the DNA insert of the plasmid deposited with the EMBL Accession Number Y07593, or SEQ ID NO:3 which also includes the start codon and antisense molecules which are complementary to a portion of the 3' untranslated region of SEQ ID NO:1, or the nucleic acid sequence of the DNA insert of the plasmid deposited with the EMBL Accession Number Y07593, or SEQ ID NO:3. A CAR modulator which inhibits CAR nucleic acid expression can also be a small molecule or other drug, e.g., a small molecule or drug identified using the screening assays described herein, which inhibits CAR nucleic acid expression. If it is desirable to treat a disease or disorder characterized by (or associated with) CAR nucleic acid expression and/or CAR protein activity by stimulating CAR nucleic acid expression, a CAR modulator can be, for example, a nucleic acid molecule encoding CAR (e.g., a nucleic acid molecule comprising a nucleotide sequence homologous to the nucleotide sequence of SEQ ID NO:1, or the nucleic acid sequence of the DNA insert of the plasmid deposited with the EMBL Accession Number Y07593, or SEQ ID NO:3) or a small molecule or other drug, e.g., a small molecule (peptide) or drug identified using the screening assays described herein, which stimulates CAR nucleic acid expression.

Alternatively, if it is desirable to treat a disease or disorder characterized by (or associated with) CAR nucleic acid expression and/or CAR protein activity by inhibiting CAR protein activity, a CAR modulator can be an anti-CAR antibody or a small molecule or other drug, e.g., a small molecule or drug identified using the screening assays described herein, which inhibits CAR protein activity. If it is desirable to treat a disease or disorder characterized by (or associated with) CAR nucleic acid expression and/or CAR protein activity by stimulating CAR protein activity, a CAR modulator can be an active CAR protein or portion thereof (e.g., a CAR protein or portion thereof having an amino acid sequence which is homologous to the amino acid sequence of SEQ ID NO:2 or a portion thereof) or a small molecule or other drug, e.g., a small molecule or drug identified using the screening assays described herein, which stimulates CAR protein activity.

Other aspects of the invention pertain to methods for modulating a cell associated activity. These methods include contacting the cell with an agent (or a composition which includes an effective amount of an agent) which modulates CAR activity or CAR expression such that a cell associated activity is altered relative to a cell associated activity of the cell in the absence of the agent. As used herein, "a cell associated activity" refers to a normal or abnormal activity or function of a cell. Examples of cell associated activities include proliferation, migration, differentiation, production or secretion of molecules, such as proteins, and cell survival. In a preferred embodiment, the cell is capable of serving as an attachment receptor for coxsackievirus or adenovirus. The term "altered" as used herein refers to a change, e.g., an increase or decrease, of a cell associated activity. In one embodiment, the agent stimulates CAR protein activity or CAR nucleic acid expression. Examples of such stimulatory agents include an active CAR protein, a nucleic acid molecule encoding CAR that has been introduced into the cell, and a modulatory agent which stimulates CAR protein activity or CAR nucleic acid expression and which is identified using the drug screening assays described herein. In another embodiment, the agent inhibits CAR protein activity or CAR nucleic acid expression. Examples of such inhibitory agents include an antisense CAR nucleic acid molecule, an anti-CAR antibody, and a modulatory agent which inhibits CAR protein activity or CAR nucleic acid expression and which is identified using the drug screening assays described herein. These modulatory methods can be performed in vitro (e.g., by culturing the cell with the agent) or, alternatively, in vivo (e.g., by administering the agent to a subject). In a preferred embodiment, the modulatory methods are performed in vivo, i.e., the cell is present within a subject, e.g., a mammal, e.g., a human, and the subject has a disorder or disease characterized by or associated with CAR activity or expression.

A nucleic acid molecule, a protein, a CAR modulator etc. used in the methods of treatment can be incorporated into an appropriate pharmaceutical composition described herein and administered to the subject through a route which allows the molecule, protein, modulator etc. to perform its intended function. Examples of routes of administration are also described herein under subsection IV.

Another aspect of the invention pertains to a method for enhancing gene transfer for genetic therapy. This method typically includes the step of introducing CAR nucleic acid, or CAR peptides, or a biologically active portion thereof into the host cell to up-regulate, increase, or enhance attachment or entry of coxsackiesvirus, preferably adenovirus, or both coxsackievirus and adenovirus vectors with/into the host cells.

This invention is further illustrated by the following examples which should not be construed as limiting. The contents of all references, patent applications, patents, and published patent applications cited throughout this application are hereby incorporated by reference.

Materials and Methods

The following materials and methods were used throughout the following examples.

Affinity purification using MAb RmcB

All procedures were performed at 0–4° C. $2.7 \times 10^{10}$ HeLa S3 cells (grown by the Cell Culture Center, Cellex Biosciences, Minneapolis) were homogenized in 10 mM Tris buffer pH 7.6 containing 2.5 mM EDTA, 2.5 mM EGTA, and protease inhibitors (1.5 mM PMSF, 40 mcg/ml aprotinin, 1 mcg/ml pepstatin, and 2 mcg/ml leupeptin). After centrifugation at 145,000×g for 90 minutes the pellet containing membranes and nuclei was homogenized in 50 mM Tris pH 7.6, 150 mM NaCl, 2 mM EDTA, 2mM EGTA (Lysis Buffer, LB) containing protease inhibitors as above. Triton X-100 was added to a final concentration of 1% and proteins were extracted for three hours. Insoluble material was removed by centrifugation for 90 min at 145,000×g, then the clarified extract was precleared with CL4B Protein A-Sepharose beads overnight.

Additional preclearing was performed by pumping the extract through pre-columns containing, first, polyclonal rabbit anti-human albumin antibody (Sigma) and anti-β1 integrin MAb DE9 (Bergelson et al., 1992) covalently coupled to Protein G-Sepharose (Gammabind, Pharmacia), and then a mixture of Protein A- and Protein G-Sepharose. Affinity chromatography was performed by pumping the precleared extract through a 1.2 ml column containing 6 mg of MAb RmcB coupled to Protein-G Sepharose. Unbound proteins were removed by washing with 1,000 ml of LB-1% Triton, 200 ml of LB-1% Triton-0.2% sodium deoxycholate, 50 ml of 5 M LiCl-20 mM Tris pH 7.6, then 20 ml of 10 mM Tris pH 8.0. Bound protein was eluted by incubating the column for 1 hr in 50 mM diethylamine pH 11.5. Fractions were then collected and analyzed on a silver-stained polyacrylamide gel.

Fractions containing a 44/46 kD protein doublet were pooled, lyophilized, and heated for 5 min at 92° C. in 3×Laemmli sample buffer before electrophoresis in a 10% SDS-polyacrylamide gel. Proteins were visualized by staining for 20 min in 20% methanol containing 0.5% acetic acid and 0.2% Coomassie Brilliant Blue (Biorad R-250), and destaining in 30% methanol as described (Rosenfeld et al., 1992).

The protein bands were excised and pooled. After in-gel digestion with trypsin, the sequences of four peptides were determined at the Harvard Microchemistry Facility by collisionally activated dissociation (CAD) on a Finnigan TSQ 7000 triple quadrupole mass spectrometer.

cDNA Isolation, Transfection, and Measurement of CAR Protein and mRNA Expression A corresponding EST cDNA isolated from an infant brain library was identified by a BLAST search (Altschul et al., 1990) of the dbEST database. A 282 bp HindIII/NdeI fragment excised from the EST cDNA [emb F05145; I.M.A.G.E. Consortium Clone ID 25001 (Lennon et al., 1996)] (Genome Systems, St. Louis) was labeled with $^{32}$P and used to screen 850,000 colonies of a pcDNAI HeLa cell library (Invitrogen, San Diego) by standard techniques (Ausubel et al., 1995). Five cDNA clones were obtained and analyzed by restriction digestion and partial sequencing. One of these (named CAR) was sufficiently long to encode a protein of the expected size, and its complete nucleotide sequence was determined.

Electroporation of dhfr$^-$ CHO cells with CAR cDNA and a plasmid encoding dihydrofolate reductase, selection of transfectants in nucleoside-free medium, and fluorescence-activated cell sorting were performed as described for transfection with the integrin α2 subunit (Bergelson et al., 1993).

Cell surface Iodination was performed by the glucose-oxidase/lactoperoxidase method (Hubbard and Cohn, 1972), cell lysates were prepared in LB-1% Triton X-100, and immunoprecipitation was performed using monoclonal antibodies bound to Protein G-Sepharose. For RNA blot analysis, an 1137 bp cDNA fragment encoding the CAR protein, excised with endonucleases PstI and NdeI, was labeled with $^{32}$P and used to probe a multiple tissue northern blot (Clontech) containing 2 mcg of poly A$^+$ RNA from each of eight human tissues. Final washes were in 0×SSC, 0.1% SDS at 50° C.

Assays of virus attachment and infection

Coxsackievirus B3 (strain Nancy), maintained in the laboratory of R.L.C., and coxsackievirus B4 (strain J.V.B.) and echovirus 1 (strain Farouk) obtained from the American Type Culture Collection were radiolabeled by growth in medium containing $^{35}$S-methionine and purified by sedimentation on sucrose gradients as described (Bergelson et al., 1993). Plaque assays were performed on HeLa cell monolaycrs as described (Bergelson et al., 1993). Adenovirus 2 was labeled by growth in $^{35}$S-methionine. 18 hours after infection (4,000 particles/cell), HeLa cells were transferred to Joklick's modified Eagle's medium containing 1/50th the usual concentration of methionine, and radiolabeled methionine (1.0 mCi per 3.5L of cell suspension) was added. Infected cells were harvested 48 hours later and virus was purified by centrifugation in CsCl as described (Maizel et al., 1968). The virus band from the second CsCl gradient was stored in 50% glycerol at −20° C.

Radiolabeled virus binding assays were performed essentially as described (Bergelson et al., 1993). Cell monolayers in 24-well plates were incubated with radiolabeled virus in Hank's balanced salt solution containing 2 mM CaCl$_2$, 2 mM MgCl$_2$, 10 mM HEPES and 4% calf serum (virus binding buffer). In some experiments, monolayers were preincubated with control MAb MOPC 195 or with MAb RmcB (ascites fluid diluted 1/100), then washed before addition of radiolabeled virus. Coxsackie B viruses were allowed to bind for 4 hours, and adenoviruses for 1 hour.

$^{35}$S-labeled adenovirus 2 fibers were purified from the top 10 ml of the CsCl gradients used to purify the virus. After dialysis in 10 mM phosphate buffer (pH 7.4), the soluble proteins were loaded onto a Mono Q anion exchange column (HR10/10, Pharmacia), equilibrated with 10 mM Tris-HCl (pH 6.6) and eluted with NaCl at approximately 150 mM concentration. Radiolabeled fibers were diluted in virus binding buffer before incubation with cell monolayers in 6-well plates for 90 min at room temperature.

To prepare recombinant knob domains, the HpaI/SmaI fragment of the adenovirus 5 fiber gene (Chroboczek and Jacrot, 1987) was cloned into the pTrcHisC vector (Invitrogen). A recombinant protein including five of 22 fiber shaft repeating units. the COOH terminal knob, and a histidine tag, was expressed in E. coli and purified by adsorption to Ni2$^+$NTA-Aaarose (Quiagen) and elution with phosphate buffer containing 250 mM imidazole. Gel electrophoresis showed the presence of both monomeric and trimeric recombinant knob protein. For inhibition assays, cell monolayers were preincubated with 0.7 mcg of recombinant knob domain for 30 min at room temperature before addition of radiolabeled viruses.

Ad.CMV-β-gal (Manome et al., 1996) was kindly provided by Dr. Toshi Tanaka (Dana-Farber Cancer Institute). For assays of β-galactosidase transduction, 150,000–200,000 cells/well in 24 well plates were incubated with Ad.CMV-β-gal for 1 hour at room temperature at multiplicities of 0–100 plaque forming units per cell, then unbound virus was removed and cells were incubated for 40 hr at 37° C. Some monolayers were then fixed with 2% paraformaldehyde and stained in situ by incubation with PBS containing 5 mM ferric and 5 mM ferrous cyanide, 1 mM MgCl$_2$ and 1 mg/ml X-gal (5-bromo-4-chloro-3-indolyl-β-D-galactoside). In other experiments, monolayers were lysed for spectrophotometric assay of β-galactosidase using reagents provided in the Promega β-galactosidase enzyme assay system. Each monolayer was extracted with 200 mcl of lysis buffer, then lysates were clarified by centrifugation, diluted 1/5, and mixed with an equal volume of development buffer containing ONPG (o-nitrophenyl β-D-galactopyranoside. Absorbance at 405 nm was measured at 20 second intervals for 30 min in a kinetic microplate reader (Molecular Devices) and V$_{max}$ was calculated for each sample.

Isolation of mCAR and cDNA and mCAR expression on transfected cells.

A C57BI/6 mouse liver cDNA library (Gibco BRL) in the pCMV-Sport2 mammalian expression vector was screened with an expressed sequence tag (EST) cDNA (Gen Bask W70374) found to encode a peptide sequence homologous to the C-terminus of human CAR. Two cDNA clones were obtained, and partial nucleotide sequences of hte inserts were determined [clone ml, Gen Bank Y10320; clone m2, GenBank Y11929].

Transfection of CHO dhfr cells with mCAR cDNA and selection in nucleoside-free medium were performed as described for transfection with the integrin α2 subunit (3). Flow cytometry and fluorescence activated cell sorting were performed with rat antiserum raised against the p46 putative murine brain receptor for CB3 (30), or control serum from an unimmunized rat, followed by fluorescein isothiocyanate (FITC)-conjugated goat-antibody to rat immunoglobulin (Sigma). Sera were preadsorbed against untransfccted CHO cells overnight before use. CHO cells expressing human CAR (2) and control CHO cells expressing the human integrin α2 subunit (3) have been described.

Radiolabeled virus binding assays, plaque assays, and assays of adenovirus-mediated gene transfer.

Coxsackievirus B3 (Nancy), maintained in the laboratory of R.L.C., and coxsackie B4 (strain JVB) were radiolabeled and purified and virus binding and plaque assays were performed as described for echovirus 1 (3), except that cell monolayers were incubated with radiolabeled virus for 4 hours. To measure susceptibility to adenovirus-mediated gene transfer, cell monolayers were exposed to Ad.CMB-β-gal (21), and β-D-galactoside) as described (2). Adenovirus 2 fibers and recombinant adenovirus 5 fiber-knob domains were prepared as described (2).

Analysis of CAR mRNA expression.

For detection of human CAR mRNA, an 1137 bp cDNA fragment encoding the human CAR protein (GenBank Y07593), excised with endonucleases PstI and NdeI, was labeled with $^{32}$P and used to probe a multiple tissue northern blot (Clontech) containing 2 mcg of poly A+RNA from each of eight adult human tissues. A similar blot with RNA from 20 week-old Balb/c mice (Clontech) was probed with a 313 bp fragment, excised from the EST cDNA clone with XhoI and BamHI, that matched extracellular, transmembrane and cyto9plasmic domain sequences identical in both mCAR cDNA clones. Final washes were in 0.1×SSC, 0.1% SDS at 50° C.

Isolation of mCAR and cDNA and mCAR expression on transfected cells.

A C57BI/6 mouse liver cDNA library (Gibco BRL) in the pCMV-Sport2 mammalian expression vector was screened with an expressed sequence tag (EST) cDNA (Gen Bask W70374) found to encode a peptide sequence homologous to the C-terminus of human CAR. Two cDNA clones were obtained, and partial nucleotide sequences of hte inserts were determined [clone m1, Gen Bank Y10320; clone m2, GenBank Y11929].

Transfection of CHO dhfr cells with mCAR cDNA and selection in nucleoside-free medium were performed as described for transfection with the integrin α2 subunit (3). Flow cytometry and fluorescence activated cell sorting were performed with rat antiserum raised against the p46 putative murine brain receptor for CB3 (30), or control serum from an unimmunized rat, followed by fluorescein isothiocyanate (FITC)-conjugated goat-antibody to rat immunoglobulin (Sigma). Sera were preadsorbed against untransfected CHO cells overnight before use. CHO cells expressing human CAR (2) and control CHO cells expressing the human integrin α2 subunit (3) have been described.

EXEMPLIFICATION

Example 1

A cDNA clone encoding CAR protein

Figure 1C:
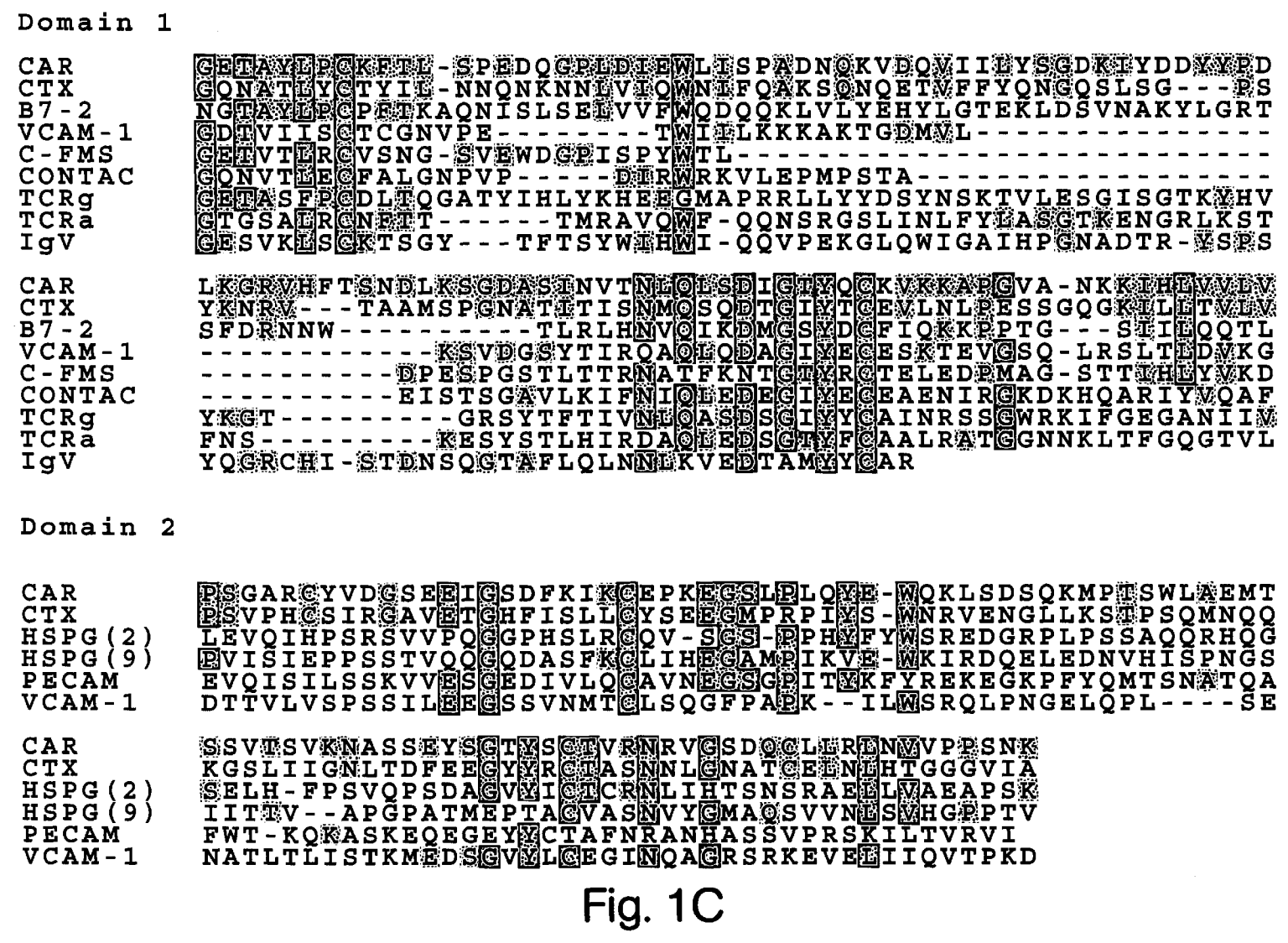

Monoclonal antibody (MAb) RmcB protects HeLa cells from infection by coxsackie B viruses (Hsu, K.-H. L., et al. (1988) J. Virol. 62, 1647–1652), and immunoprecipitates a 46 kD protein from HeLa cell lysates (FIG. 2B). The protein was purified by affinity chromatography with MAb RmcB, and the sequences of four tryptic peptides were determined (FIG. 1A). None of these peptides was identified in the Genbank nonredundant protein database, but an expressed sequence tag (EST) cDNA was identified that potentially encoded all four of the peptides. This EST cDNA was used to probe a Hela cell library constructed in the pcDNAI expression vector, and a cDNA clone was obtained. Transient transfection into murine WOP cells (Dailey, L. and Basilico, C. (1985) Sequences in polyomavirus DNA regulatory region involved in viral DNA replication and early gene expression. J. Virology 54, 739–749) and analysis by flow cytometry indicated that this cDNA encoded the protein recognized by MAb RmcB (data not shown).

The CAR cDNA encoded a 365 amino acid transmembrane protein (FIG. 1B) with a predicted 14 a.a. leader, a 222 a.a. extracellular domain, a 22 a.a. membrane-spanning helix, and a 107 a.a. intracellular domain. Alignment of the CAR sequence with sequences of proteins belonging to the immunoglobulin gene superfamily suggested that the extracellular portion of CAR consists of two immunoglobulin-like domains (FIG. 1C). Fqour potential sites for N-linked glycosylation (N-X-S/T) were present. two of them within the predicted extracellular portion of the molecule, consistent with the observation that the apparent molecular weight of the coxsackievirus receptor protein is reduced after treatment with endoglycosidase F (Hsu, K.-H. L., Paglini, S., Alstein, B. and Crowell, R. L. (1990) Identification of a second cellular receptor for a coxsackievirus B3 variant, CB3-RD. In New Aspects of Positive-Strand RNA Viruses, M. Brinton and F. Heinz, eds. (Washington, D.C.: American Society for Microbiology), pp. 271–277). The deduced amino acid sequence of a murine CAR homolog was 91% identical o that of the human protein overall and 95% identical within the cytoplasmic domain.

Figure 2B:
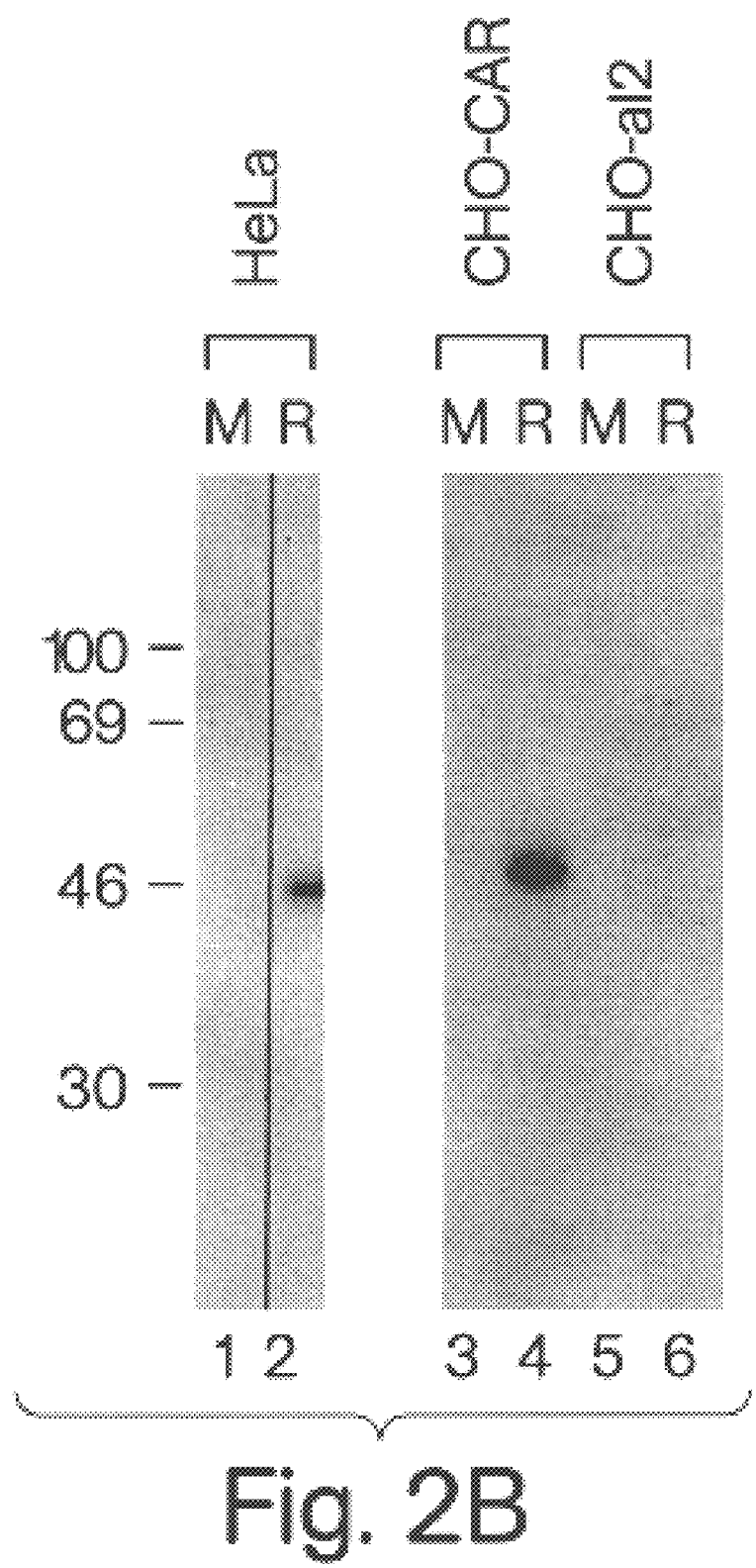

CHO dhfr⁻ hamster cells were cotransfected with CAR cDNA, and with cDNA encoding dihydrofolate reductase, and after selection in nucleoside-free medium and fluorescence activated cell sorting, a cell line, CHO-CAR, was obtained that homogeneously expressed the putative receptor protein (FIG. 2A). CAR protein was not detected on the surface of CHO cells transfected with a control cDNA encoding the human integrin α2 subunit. As expected, MAb RmcB immunoprecipitated a 46 kD cell protein from detergent lysates of iodinated CHO-CAR transfectants, but not from lysates of CHO-α2 control cells (FIG. 2B).

Example 2

The CAR protein functions as a coxsackievirus receptor

Figure 3A:
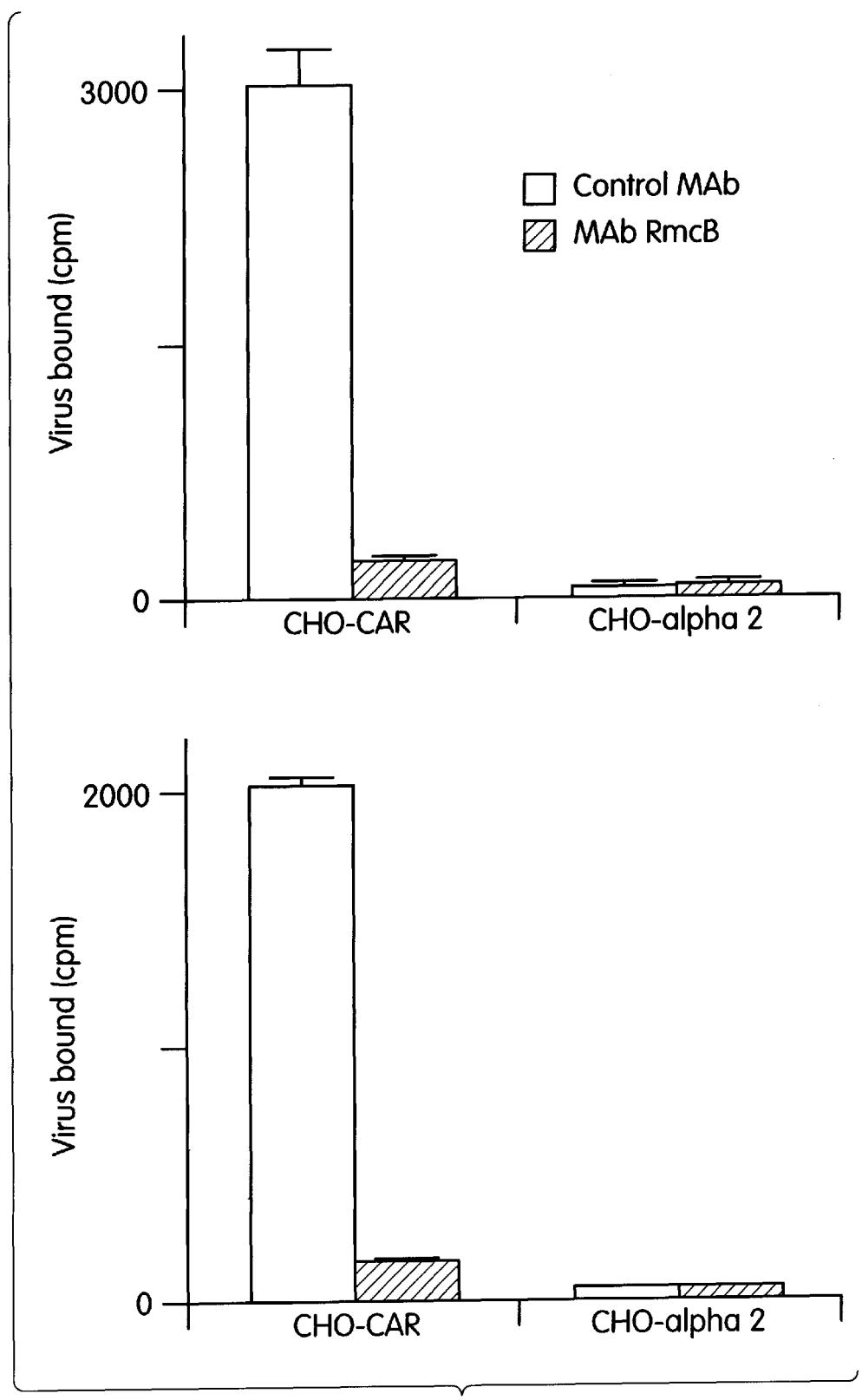
Figure 3B:
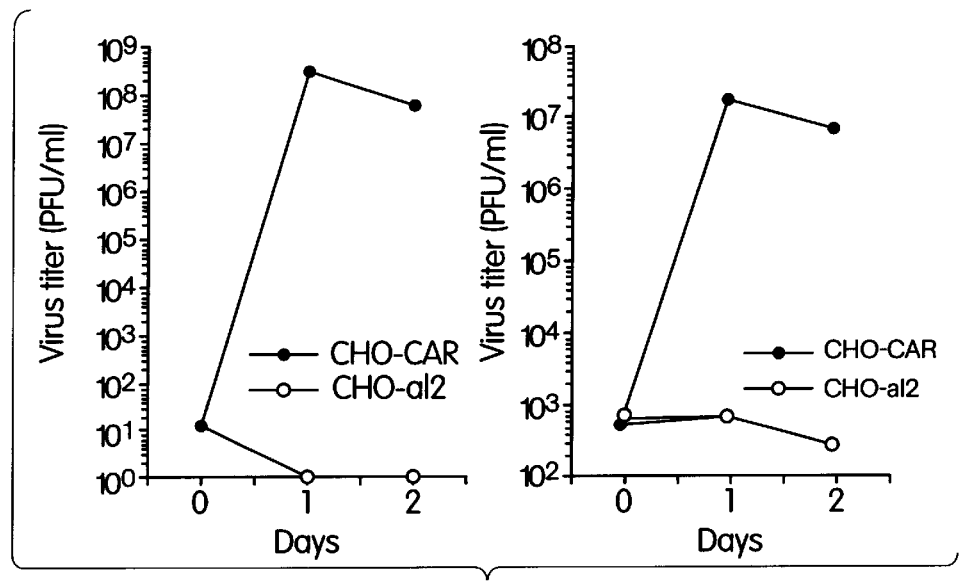

CHO-CAR cells, but not the control transfectants, bound radiolabeled coxsackievirus B3 and coxsackievirus B4, and binding was inhibited by preincubation with MAb RmcB (FIG. 3A). Echovirus 1, a picornavirus whose receptor is the human α2β1 integrin (Bergelson, J. M., et al. (1992) Science 255, 1718–1720), did not bind to CHO-CAR cells, but did, as previously demonstrated (Bergelson, J. M., et al. (1993) J. Virology 67, 6847–6852), bind to the CHO-α2 control (data not shown). CHO-CAR cells became infected by coxsackieviruses B3 and B4, as evidenced by viral cytopathic effect (not shown) and by active virus replication (FIG. 3B). These results demonstrate that the protein encoded by CAR cDNA is a functional virus receptor, mediating cell attachment and infection by coxsackieviruses B3 and B4.

Example 3

The CAR protein functions as an adenovirus receptor

Figure 4A:
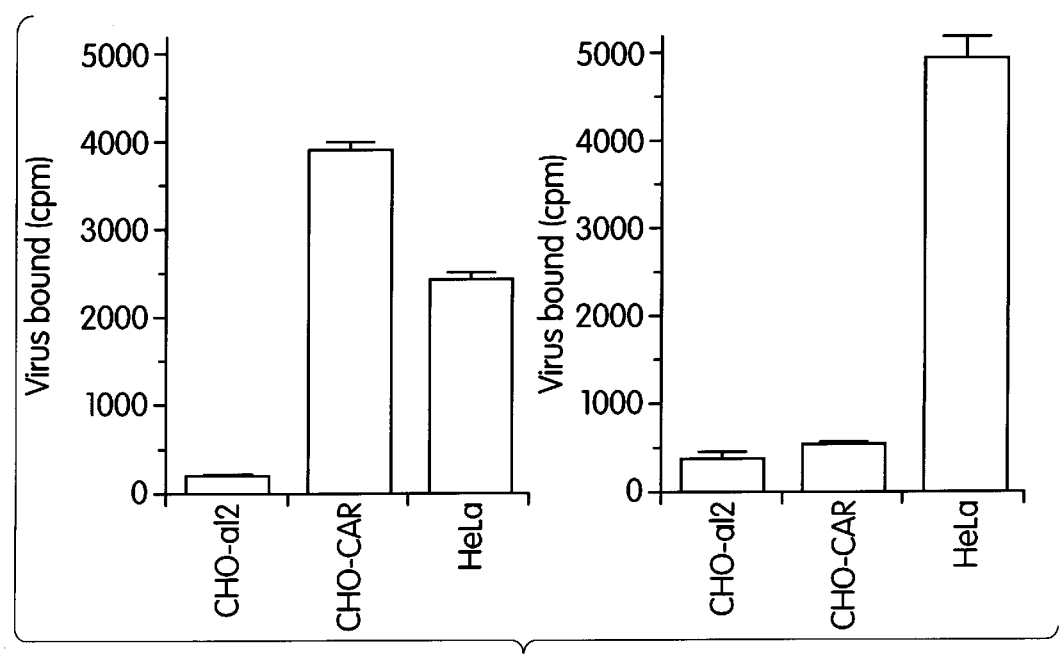
Figure 4B:
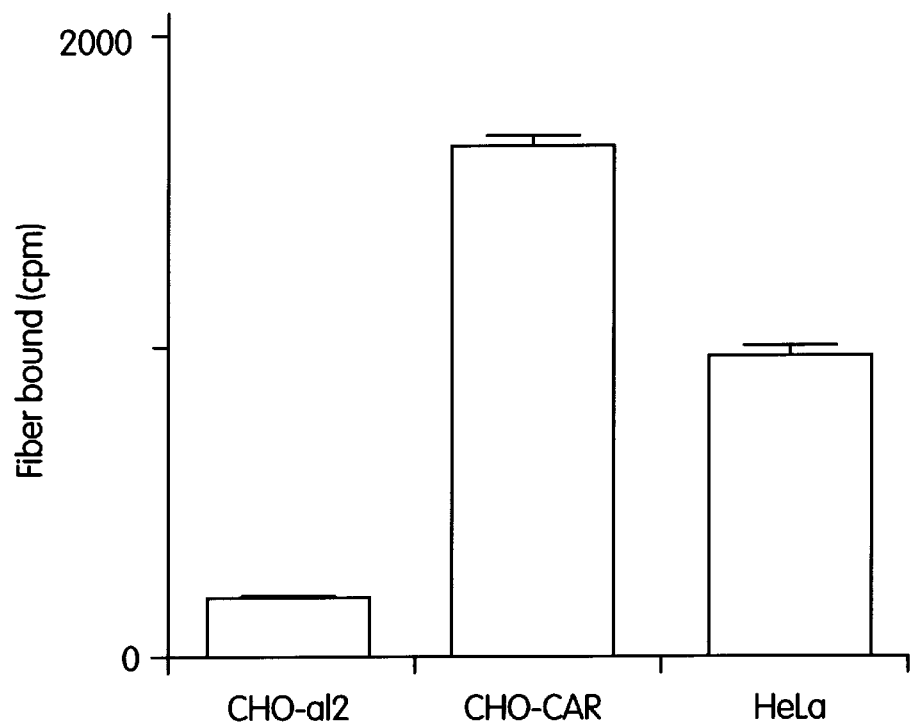
Figure 4C:
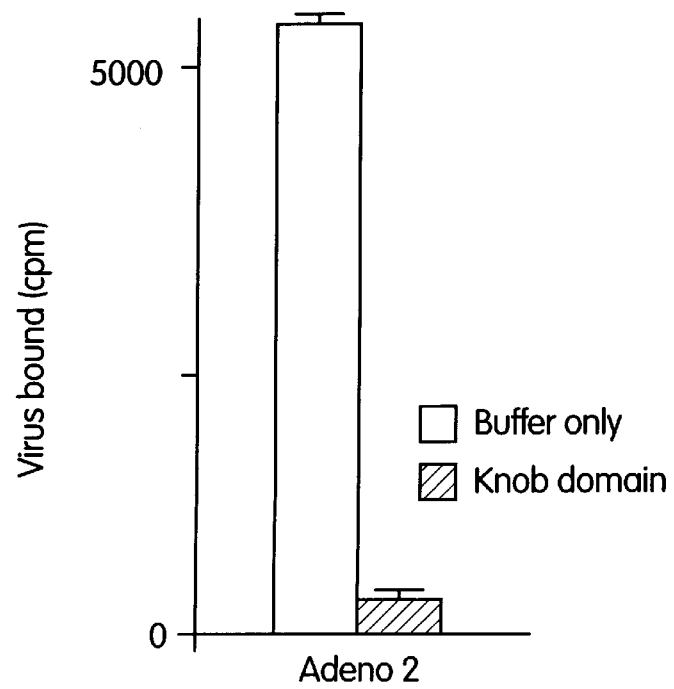
Figure 4C:
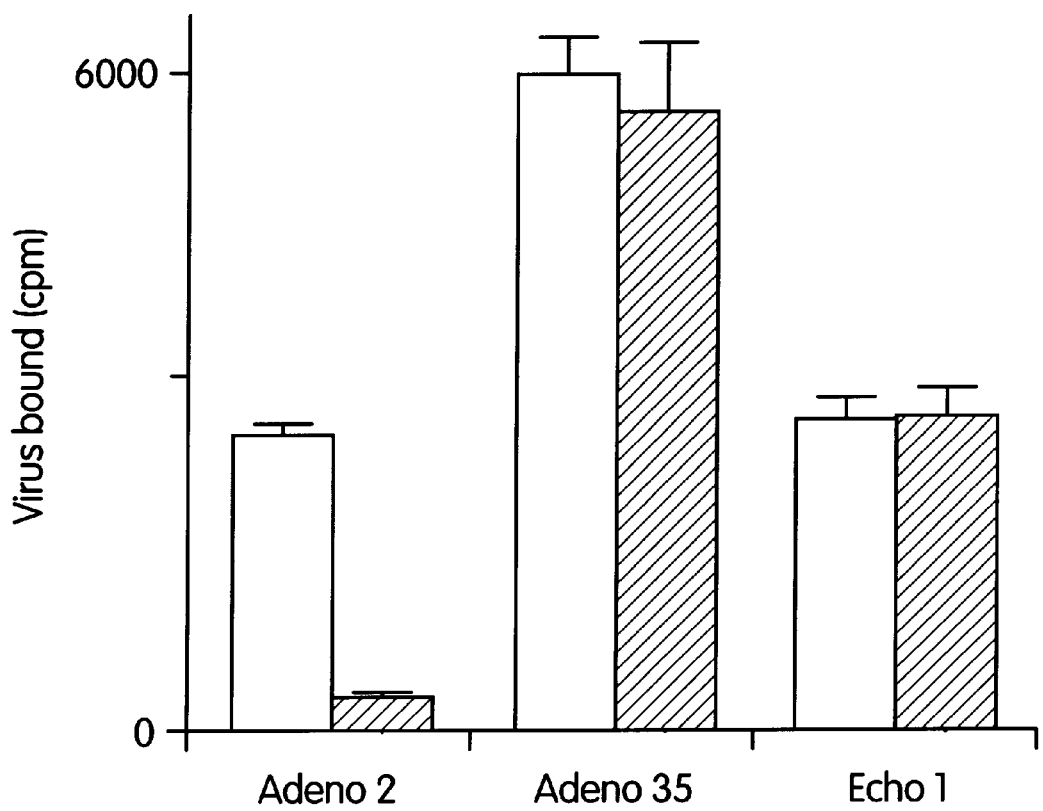

Competition binding experiments suggest that adenoviruses 2 and 5 (members of agglutination group C) bind to the same cellular receptor, distinct from the receptor for viruses belonging to group B (Defer, C., et al. (1990) J. Virology 64, 3661–3673). Virus attachment is mediated by fibers projecting from the virus capsid (Philipson et al., 1968). A globular knob at the tip of the fiber binds directly to the cellular receptor, and isolated knob domains block virus attachment (Henry et al., 1994; Louis et al., 1994; Stevenson et al., 1995). Because adenovirus 2 and coxsackievirus B3 compete for a HeLa cell attachment site (Lonberg-Holm, K., et al. (1976) Nature 259, 679–681), CAR might be a receptor for adenovirus as well as for coxsackie B. Remarkably, radiolabeled adenovirus 2 (FIG. 4A) and isolated adenovirus 2 fibers bound specifically to CHO-CAR cells (FIG. 4B). Virus attachment was blocked by recombinant adenovirus 5 knob domains (FIG. 4C). In control experiments, a group B virus, adenovirus 35, did not bind to CHO-CAR transfectants (FIG. 4A), and recombinant knob domains did not inhibit attachment of adenovirus 35 or the picornavirus echovirus 1 to HeLa cells (FIG. 4C). These results confirm that CAR protein is a receptor responsible for specific fiber-mediated adenovirus attachment to cells.

Figure 5A:
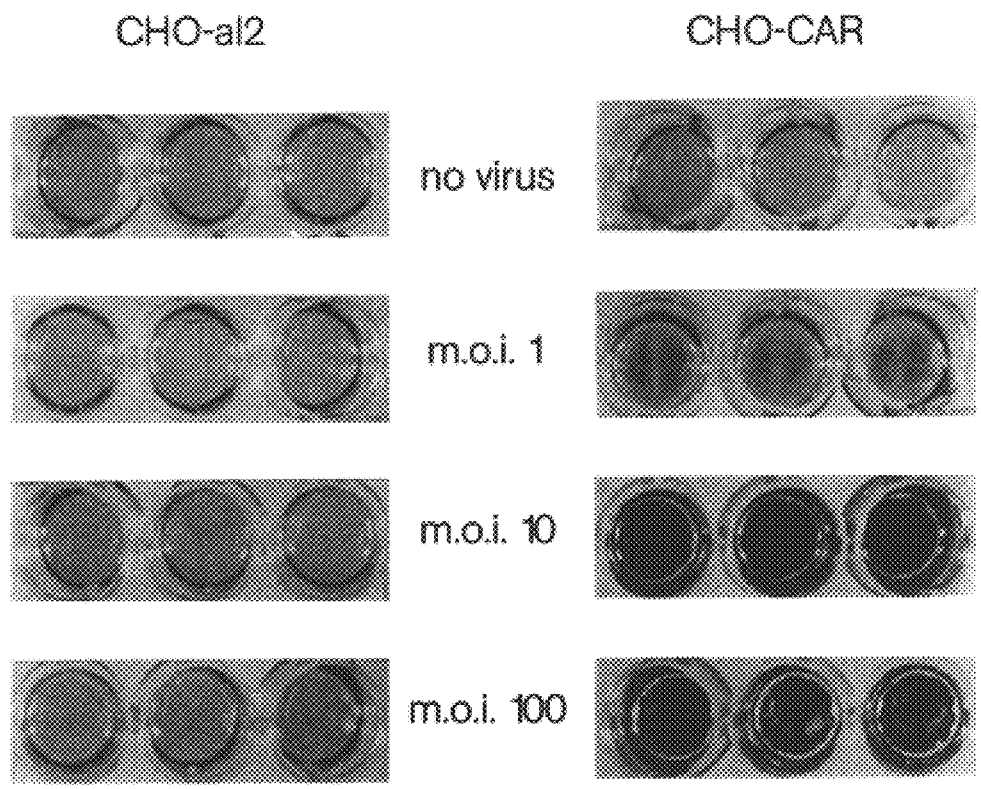
Figure 5B:
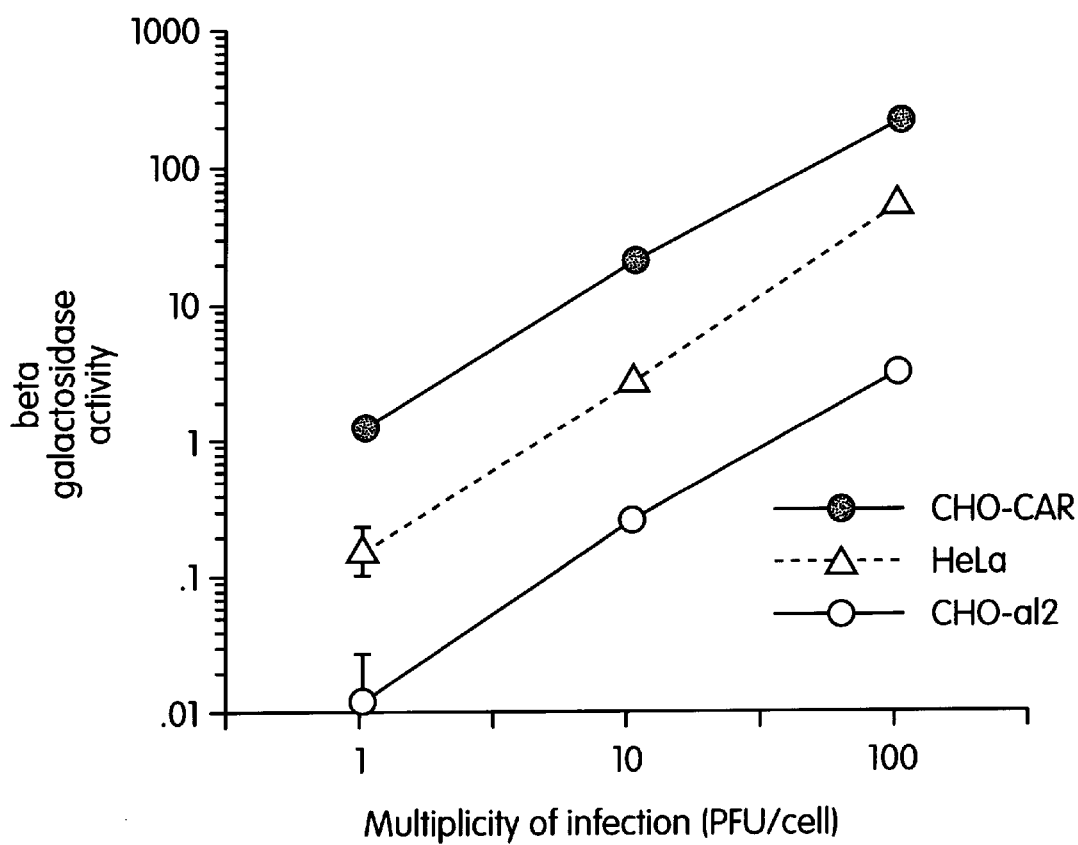

Adenovirus enters CEIO cells to some extent (although the entry process is much less efficient than entry into HeLa cells), but there is a post-entry block to viral protein synthesis and virus replication (Longiaru and Horwitz, 1981). The efficiency of adenovirus-mediated gene delivery was measured, rather than virus production, to test whether virus attachment to the CAR protein leads to adenovirus internalization. CHO-CAR cells or CHO-α2 control transfectants were incubated with adenovirus 5 engineered to encode β-galactosidase [Ad.CMV-βgal, (Manome, Y., et al. (1996) Nature Medicine 2, 567–573] at several multiplicities of infection, and β-galactosidase activity was measured 48 hours later. Cytotoxicity was noted at 48 hours in the CHO-CAR cells exposed to Ad.CMV-βgal at high multiplicity, although the mechanism by which this defective virus caused cell damage is uncertain. Expression of CAR greatly enhanced gene transduction by adenovirus 5 as demonstrated by in-situ staining with X-gal (FIG. 5A). When examined by light microscopy, 30–50% of CHO-CAR cells infected at a multiplicity of 1 PFU/cell, and virtually every cell infected at higher multiplicity, expressed β-galaetosidase (not shown). Quantitative colorimetric assay on cell lysates (FIG. 5B) was also performed. At each multiplicity of infection, enzyme activity was approximately 100-fold greater in the CAR transfectants than in the control cells (and also greater than in HeLa cells, which express endogenous CAR, but at lower levels). These results demonstrate that attachment to CAR on the cell surface markedly facilitates virus entry and adenovirus-mediated gene transfer.

Example 4
Expression of CAR RNA in human tissues

The translated portion of the CAR cDNA was used to probe a Northern blot containing RNA from several human tissues (FIG. 6). CAR cDNA hybridized to a 6.5 kb major RNA species and a minor species 3.5 kb in length. Strongest expression of CAR mRNA was noted in heart, pancreas and brain. Faint bands reflecting expression at lower levels were detected in lung and liver on the original autoradiograph.

Example 5
Identification and expression of the murine CAR homologue (mCAR).

The dbEST database was searched to identify a murine cDNA clone that could encode a protein homologous to human CAR, then used it to screen a mouse liver cDNA library. Two cDNA clones were obtained that potentially encoded proteins with over 90% amino acid identity to the extracellular domain of human CAR (FIG. 6), and up to 95% identity within the cytoplasmic domain. The predicted mCAR peptide sequences were identical in the extracellular and transmembrane domains, but diverged at the C-terminus: in clone m2, the C-terminal 26 amino acids of clone m1 were replaced by 13 different amino acids.

CHO cells transfected with each of the cDNAs expressed antigen detectable by rat antiserum raised against the 46 kD putative murine CB3 receptor (Xu, R., et al. (1995) *Virus Research*, 35: 323–340), but were not stained by control rat serum (FIG. 8, and data not shown). No staining of control cells transfected with the human integrin α2 subunit (CHO-αl2) was detected. These results suggest that mCAR is the CB3-binding protein previously identified in newborn mouse brain (Xu, et al. 1995).

Example 6
Coxsackie B virus interaction with mCAR.

CHO cells transfected with mCAR cDNA (clone m1 or m2, CHO-mCAR). but not control CHO-αl2 cells, bound radiolabeled CB3 and CB4 (FIG. 9, and data not shown). When exposed to CB3 and CB4, CHO-mCAR cells became infected, as demonstrated by viral cytopathic effects (not shown) and increase in virus titer (FIG. 10). These results indicate that mCAR is a receptor mediating coxsackie B virus attachment and injection.

Example 7
Adenovirus interaction with mCAR.

Adenovirus attachment to cells is mediated by globular knobs, located at the tips of fibers that project from the capsid surface (Defer, C., et al. (1990) *J. Virology*, 64: 3661–3673; Henry, L. J., et al. (1994) *J. Virology*, 68: 5239–5246; Louis, N., et al. (1994) *J. Virology*, 68: 4104–4106; Philipson, L., et al. (1968) *J. Virology*, 2: 1064–1075). As was previously observed with human CAR (Bergelson, J. M., et al. (1997) *Science*, 275: 1320–1323), coxsackievirus attachment to mCAR-transfected CHO cells was inhibited by recombinant adenovirus knob domains (FIG. 9), suggesting that murine CAR may also interact with adenoviruses. The efficiency of gene delivery to transfected cells using adenovirus 5 engineered to encode β-galactosidase [Ad.CMV-βgal, (26)] (FIG. 11) was measured. As determined by in situ staining with X-gal, expression of mCAR on transfected cells markedly enhanced adenovirus 5-mediated gene deliver. Similar results were obtained when CHO cells were transfected either with clone m1 or m2. Adenoviruses 2 and 5 are known to complete for a singe fiber attachment site on human CAR (Beroelson, J. M., et al. (1997) *Science*, 275: 1320–1323; Defer, C., et al. (1990) *J. Virology*, 64: 3661–3673; Philipson, L., et al. (1968) *J. Virology*, 2: 1064–1075). Consistent with this, delivery of the β-galactosidase gene to CHO-mCAR cells was inhibited by adenovirus 2 fibers (FIG. 11). These results indicate that mCAR, like the human protein, mediates fiber-dependent adenovirus interactions with adenoviruses 2 and 5.

These results demonstrate that mCAR, like the human receptor for coxsackieviruses and adenoviruses, mediates interactions with two genetically and structurally distinct viral pathogens. When transfected with mCAR cDNA, non-permissive CHO cells became susceptible to infection by coxsackieviruses B3 and B4, and showed increased susceptibility to adenovirus-mediated gene delivery. Furthermore, specific antibody staining of mCAR-transfected cells indicated that mCAR protein is the 46 kD coxsackievirus binding protein previously demonstrated in newborn mouse brain (Xu, R., et al. (1995) *Virus Research*, 35: 323–340).

Similar results were obtained when CHO cells were transfected with either of two mCAR cDNA clones, encoding proteins with divergent C-termini. It thus appears that the 26 C-terminal amino acids of clone ml, which are nearly identical to human CAR, are not essential for mCAR's receptor function. Using specific primers in RT-PCR, RNAs corresponding to both clones M1 and m2 in a variety of murine tissues (unpublished results) were detected.

Example 8
Tissue-specific expression of CAR and mCAR RNA.

Murine and human CAR cDNA was used to probe Northern blots containing RNA from adults murine and human tissues (FIG. 12). Hybridization with a 6.5 kb RNA species was most prominent in both human and murine tissues, but minor species of other sizes were also observed. Strongest expression of human CAR mRNA was noted in heart, pancreas and brain, although expression at lower levels could be detected in liver and lung on the original autoradiograph. Murine CAR mRNA was most highly expressed in the murine liver, and relatively high levels of RNA expression were also detected in heart, lung, and kidney. These results suggest that the pattern of tissue-specific CAR expression in humans may differ from the pattern of expression in mice.

In a survey of human tissues, CAR mRNA was most highly expressed in the heart, brain, and pancreas, consistent with the patter of illness caused by coxsackie B viruses (Melnick, J. L., 1996, Polioviruses, coxsackieviruses, cehoviruses, and newer enteroviruses, p. 655–712, In B. N. Fields, D. M. Knipe and P. M. Howley (ed.), *Virology*, 3 ed. Lippincott-Raven, Philadelphia). In adult mice, high levels of mCAR RNA were detected in the heart and liver, in which significant lesions are evident during CB3 infection (Melnick, J. L., (1996). Abundant mRNA was also present in murine kidney and lung, although lesions in these organs are not commonly reported in CB3-infected mice. Little CAR mRNA was detected in the spleen, although two recent reports have indicated that CB3 infects cells—predominantly B lymphocytes—within the spleen (Anderson, D. R., et al. (1996), *J. Virology*, 70: 4632–4645; Klingel, K., et al. (1996) *J. Virology*, 70: 8888–8895).

Human adenoviruses do not replicate in most rodent cells, yet murine as well as human tissues (Davidson, B. L., et al. (1993), *Nature Genetics*, 3: 219–223; Morsy, M. A., et al. (1993) *J. Clin. Investigation*, 92: 15880–1586; Yang, Y., et al. (1994) *Nature Genetics*, 7: 362–369), can be transduced with adenovirus vectors. Gene deliver may involve—in addition to the fiber receptor now identified as CAR—virus interaction with $\alpha_v$ integrins (Goldman, M. J., et al. (1995) *J. Virology*, 69: 5951–5958), which have been shown to facilitate virus entry (Wickham, T. J., et al. (1993) *Cell*, 73: 309–319). Adenoviruses may also enter cells by fiber-independent pathways (Huang, S., et al. (1996) *J. Virology*, 70: 4502–4508). However, efficient transduction has been shown to correlate with expression of the fiber receptor (Wickham, T. J., et al. (1996) *Nature Biotechnology*, 14: 1570–1573), and further definition of the receptor's tissue distribution will be important for efforts to target gene delivery to particular sites. Because murine models are used in preclinical studies of adenovirus-mediated gene deliver, it is important to consider that, as suggested by differences in mRNA expression, the CAR fiber receptor may be more highly expressed in certain murine tissues—including the liver and lung—than it is in human tissues.

Pathogenicity in newborn mice was a characteristic originally used to distinguish coxsackieviruses from other human enteroviruses (Melnick, J. L., (1996) and it is likely that coxsackievirus host range depends on virus interactions with human and murine CAR. Age-specific expression of a receptor protein—now identified as mCAR—in the brains of newborn mice (Xu, R., et al. (1997) *Virus Research* in press) has been related to the unique susceptibility of infant mice to CB3 encephalitis (Grodums, E. I., et al. (1959) *Can. J. Microbiol.* 5: 595–604; Grodums, F. I., et al. (1961) *Can. J. Microbiol.*, 7: 175–184), suggesting that mCAR may be an important determinant of virus tropism for the murine brain.

What is claimed is:

1. An isolated nucleic acid molecule which hybridizes under stringent conditions to a second nucleic acid molecule, said second nucleic acid molecule comprising SEQ ID No:1 or the complement thereto, said stringent conditions comprising hybridization in 6×sodium chloride/sodium citrate (SSC) at about 45° C., followed by one or more washes in 0.2×SSC, 0.1% SDS at 50–65° C., wherein the isolated nucleic acid molecule encodes a protein having one or more of the following functions: (1) it can serve as a receptor for coxsackievirus or adenovirus; (2) it can modulate the activity of coxsackievirus or adenovirus; and (3) it can modulate the attachment process of coxsackievirus or adenovirus in a cell that is responsive to such pathogens.

2. An isolated nucleic acid molecule comprising the nucleotide sequence of SEQ ID NO:1.

3. The isolated nucleic acid molecule of claim 2, comprising nucleotides 60 to 1157 of the nucleotide sequence of SEQ ID NO:1.

4. An isolated nucleic acid molecule encoding the amino acid sequence of SEQ ID NO:2.

5. A vector comprising the isolated nucleic acid molecule of claim 1, 2, 3 or 4.

6. The vector of claim 5, which is a recombinant expression vector.

7. A host cell containing the vector of claim 5.

8. A method for producing a protein comprising culturing the host cell of claim 7 in a suitable medium under conditions which result in the production of the protein encoded by said nucleic acid.

* * * * *

UNITED STATES PATENT AND TRADEMARK OFFICE
CERTIFICATE OF CORRECTION

PATENT NO. : 6,210,921 B1
DATED : April 3, 2001
INVENTOR(S) : Robert W. Finberg, et al.

It is certified that error appears in the above-identified patent and that said Letters Patent is hereby corrected as shown below:

<u>Title page,</u>
The residence of the Inventor, Marshall S. Horwitz, should be:
Bronx, New York, instead of Larchmont, New York Signed and Sealed this Second Day of October, 2001

*Attest:*

NICHOLAS P. GODICI
*Attesting Officer*     *Acting Director of the United States Patent and Trademark Office*

```
                           SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
        (A) LENGTH: 1584 base pairs
        (B) TYPE: nucleic acid
        (C) STRANDEDNESS: single
        (D) TOPOLOGY: linear (ii) MOLECULE TYPE: cDNA (ix) FEATURE:
         (A) NAME/KEY: CDS
         (B) LOCATION: 60..1157

(xi) SEQUENCE DESCRIPTION: SEQ ID NO:1:

GAATTCCCAG GAGCGAGAGC CGCCTACCTG CAGCCGCCGC CCACGGCACG GCAGCCACC          59

ATG GCG CTC CTG CTG TGC TTC GTG CTC CTG TGC GGA GTA GTG GAT TTC         107
Met Ala Leu Leu Leu Cys Phe Val Leu Leu Cys Gly Val Val Asp Phe
  1               5                  10                  15

GCC AGA AGT TTG AGT ATC ACT ACT CCT GAA GAG ATG ATT GAA AAA GCC         155
Ala Arg Ser Leu Ser Ile Thr Thr Pro Glu Glu Met Ile Glu Lys Ala
             20                  25                  30

AAA GGG GAA ACT GCC TAT CTG CCG TGC AAA TTT ACG CTT AGT CCC GAA         203
Lys Gly Glu Thr Ala Tyr Leu Pro Cys Lys Phe Thr Leu Ser Pro Glu
         35                  40                  45

GAC CAG GGA CCG CTG GAC ATC GAG TGG CTG ATA TCA CCA GCT GAT AAT         251
Asp Gln Gly Pro Leu Asp Ile Glu Trp Leu Ile Ser Pro Ala Asp Asn
     50                  55                  60

CAG AAG GTG GAT CAA GTG ATT ATT TTA TAT TCT GGA GAC AAA ATT TAT         299
Gln Lys Val Asp Gln Val Ile Ile Leu Tyr Ser Gly Asp Lys Ile Tyr
 65                  70                  75                  80
```

```
GAT GAC TAC TAT CCA GAT CTG AAA GGC CGA GTA CAT TTT ACG AGT AAT     347
Asp Asp Tyr Tyr Pro Asp Leu Lys Gly Arg Val His Phe Thr Ser Asn
                 85                  90                  95

GAT CTC AAA TCT GGT GAT GCA TCA ATA AAT GTA ACG AAT TTA CAA CTG     395
Asp Leu Lys Ser Gly Asp Ala Ser Ile Asn Val Thr Asn Leu Gln Leu
            100                 105                 110

TCA GAT ATT GGC ACA TAT CAG TGC AAA GTG AAA AAA GCT CCT GGT GTT     443
Ser Asp Ile Gly Thr Tyr Gln Cys Lys Val Lys Lys Ala Pro Gly Val
        115                 120                 125

GCA AAT AAG AAG ATT CAT CTG GTA GTT CTT GTT AAG CCT TCA GGT GCG     491
Ala Asn Lys Lys Ile His Leu Val Val Leu Val Lys Pro Ser Gly Ala
    130                 135                 140

AGA TGT TAC GTT GAT GGA TCT GAA GAA ATT GGA AGT GAC TTT AAG ATA     539
Arg Cys Tyr Val Asp Gly Ser Glu Glu Ile Gly Ser Asp Phe Lys Ile
145                 150                 155                 160

AAA TGT GAA CCA AAA GAA GGT TCA CTT CCA TTA CAG TAT GAG TGG CAA     587
Lys Cys Glu Pro Lys Glu Gly Ser Leu Pro Leu Gln Tyr Glu Trp Gln
                165                 170                 175

AAA TTG TCT GAC TCA CAG AAA ATG CCC ACT TCA TCG TTA GCA GAA ATG     635
Lys Leu Ser Asp Ser Gln Lys Met Pro Thr Ser Ser Leu Ala Glu Met
            180                 185                 190

ACT TCA TCT GTT ATA TCT GTA AAA AAT GCC TCT TCT GAG TAC TCT GGG     683
Thr Ser Ser Val Ile Ser Val Lys Asn Ala Ser Ser Glu Tyr Ser Gly
        195                 200                 205

ACA TAC AGC TGT ACA GTC AGA AAC AGA GTG GGC TCT GAT CAG TGC CTG     731
Thr Tyr Ser Cys Thr Val Arg Asn Arg Val Gly Ser Asp Gln Cys Leu
    210                 215                 220

TTG CGT CTA AAC GTT GTC CCT CCT TCA AAT AAA GCT GGA CTA ATT GCA     779
Leu Arg Leu Asn Val Val Pro Pro Ser Asn Lys Ala Gly Leu Ile Ala
225                 230                 235                 240

GGA GCC ATT ATA GGA ACT TTG CTT GCT CTA GCG CTC ATT GGT CTT ATC     827
Gly Ala Ile Ile Gly Thr Leu Leu Ala Leu Ala Leu Ile Gly Leu Ile
                245                 250                 255

ATC TTT TGC TGT CGT AAA AAG CGC AGA GAA GAA AAA TAT GAA AAG GAA     875
Ile Phe Cys Cys Arg Lys Lys Arg Arg Glu Glu Lys Tyr Glu Lys Glu
            260                 265                 270

GTT CAT CAC GAT ATC AGG GAA GAT GTG CCA CCT CCA AAG AGC CGT ACG     923
Val His His Asp Ile Arg Glu Asp Val Pro Pro Pro Lys Ser Arg Thr
        275                 280                 285

TCC ACT GCC AGA AGC TAC ATC GGC AGT AAT CAT TCA TCC CTG GGG TCC     971
Ser Thr Ala Arg Ser Tyr Ile Gly Ser Asn His Ser Ser Leu Gly Ser
    290                 295                 300

ATG TCT CCT TCC AAC ATG GAA GGA TAT TCC AAG ACT CAG TAT AAC CAA    1019
Met Ser Pro Ser Asn Met Glu Gly Tyr Ser Lys Thr Gln Tyr Asn Gln
305                 310                 315                 320

GTA CCA AGT GAA GAC TTT GAA CGC ACT CCT CAG AGT CCG ACT CTC CCA    1067
Val Pro Ser Glu Asp Phe Glu Arg Thr Pro Gln Ser Pro Thr Leu Pro
                325                 330                 335

CCT GCT AAG GTA GCT GCC CCT AAT CTA AGT CGA ATG GGT GCG ATT CCT    1115
Pro Ala Lys Val Ala Ala Pro Asn Leu Ser Arg Met Gly Ala Ile Pro
            340                 345                 350

GTG ATG ATT CCA GCA CAG AGC AAG GAT GGG TCT ATA GTA TAGAGCCTCC     1164
Val Met Ile Pro Ala Gln Ser Lys Asp Gly Ser Ile Val
        355                 360                 365

ATATGTCTCA TCTGTGCTCT CCGTGTTCCT TTCCTTTTTT TGATATATGA AAACCTATTC  1224

TGGTCTAAAT TGTGTTACTA GCCTCAAAAT ACATCAAAAA ATAAGTTAAT CAGGAACTGT  1284

ACGGAATATA TTTTTAAAAA TTTTTGTTTG GTTATATCGA AATAGTTACA GGCACTAAAG  1344
```

```
TTAGTAAAGA AAAGTTTACC ATCTGAAAAA GCTGGATTTT CTTTAAGAGG TTGATTATAA    1404

AGTTTTCTAA ATTTATCAGT ACCTAAGTAA GATGTAGCGC TTTGAATATG AAATCATAGG    1464

TGAAGACATG GGTGAACTTA CTTGCATACC AAGTTGATCA TTGAATAACC ATCTGAAAGT    1524

GGTACTTGAT CATTTTTACC ATTATTTTTA GGATGTGTAT TTCATTTATT TATGGCCCAC    1584
```

(2) INFORMATION FOR SEQ ID NO:2:

(i) SEQUENCE CHARACTERISTICS:
        (A) LENGTH: 365 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Leu Leu Leu Cys Phe Val Leu Leu Cys Gly Val Val Asp Phe
 1               5                  10                  15

Ala Arg Ser Leu Ser Ile Thr Thr Pro Glu Glu Met Ile Glu Lys Ala
            20                  25                  30

Lys Gly Glu Thr Ala Tyr Leu Pro Cys Lys Phe Thr Leu Ser Pro Glu
        35                  40                  45

Asp Gln Gly Pro Leu Asp Ile Glu Trp Leu Ile Ser Pro Ala Asp Asn
    50                  55                  60

Gln Lys Val Asp Gln Val Ile Leu Tyr Ser Gly Asp Lys Ile Tyr
65                  70                  75                  80

Asp Asp Tyr Tyr Pro Asp Leu Lys Gly Arg Val His Phe Thr Ser Asn
                85                  90                  95

Asp Leu Lys Ser Gly Asp Ala Ser Ile Asn Val Thr Asn Leu Gln Leu
            100                 105                 110

Ser Asp Ile Gly Thr Tyr Gln Cys Lys Val Lys Lys Ala Pro Gly Val
        115                 120                 125

Ala Asn Lys Lys Ile His Leu Val Leu Val Lys Pro Ser Gly Ala
    130                 135                 140

Arg Cys Tyr Val Asp Gly Ser Glu Glu Ile Gly Ser Asp Phe Lys Ile
145                 150                 155                 160

Lys Cys Glu Pro Lys Glu Gly Ser Leu Pro Leu Gln Tyr Glu Trp Gln
                165                 170                 175

Lys Leu Ser Asp Ser Gln Lys Met Pro Thr Ser Ser Leu Ala Glu Met
            180                 185                 190

Thr Ser Ser Val Ile Ser Val Lys Asn Ala Ser Ser Glu Tyr Ser Gly
        195                 200                 205

Thr Tyr Ser Cys Thr Val Arg Asn Arg Val Gly Ser Asp Gln Cys Leu
    210                 215                 220

Leu Arg Leu Asn Val Val Pro Pro Ser Asn Lys Ala Gly Leu Ile Ala
225                 230                 235                 240

Gly Ala Ile Ile Gly Thr Leu Leu Ala Leu Ala Leu Ile Gly Leu Ile
                245                 250                 255

Ile Phe Cys Cys Arg Lys Lys Arg Glu Glu Lys Tyr Glu Lys Glu
            260                 265                 270

Val His His Asp Ile Arg Glu Asp Val Pro Pro Lys Ser Arg Thr
        275                 280                 285

Ser Thr Ala Arg Ser Tyr Ile Gly Ser Asn His Ser Ser Leu Gly Ser
    290                 295                 300

Met Ser Pro Ser Asn Met Glu Gly Tyr Ser Lys Thr Gln Tyr Asn Gln
305                 310                 315                 320
```

```
Val Pro Ser Glu Asp Phe Glu Arg Thr Pro Gln Ser Pro Thr Leu Pro
            325                 330                 335

Pro Ala Lys Val Ala Ala Pro Asn Leu Ser Arg Met Gly Ala Ile Pro
            340                 345                 350

Val Met Ile Pro Ala Gln Ser Lys Asp Gly Ser Ile Val
            355                 360             365

(2) INFORMATION FOR SEQ ID NO:3:

(i) SEQUENCE CHARACTERISTICS:
        (A) LENGTH: 1095 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1095

(xi) SEQUENCE DESCRIPTION: SEQ ID NO:3:
```

| | | | | | | | | | | | | | | | | |
|---|---|---|---|---|---|---|---|---|---|---|---|---|---|---|---|---|
| ATG | GCG | CTC | CTG | CTG | TGC | TTC | GTG | CTC | CTG | TGC | GGA | GTA | GTG | GAT | TTC | 48 |
| Met | Ala | Leu | Leu | Leu | Cys | Phe | Val | Leu | Leu | Cys | Gly | Val | Val | Asp | Phe | |
| 1 | | | | 5 | | | | | 10 | | | | | 15 | | |
| GCC | AGA | AGT | TTG | AGT | ATC | ACT | ACT | CCT | GAA | GAG | ATG | ATT | GAA | AAA | GCC | 96 |
| Ala | Arg | Ser | Leu | Ser | Ile | Thr | Thr | Pro | Glu | Glu | Met | Ile | Glu | Lys | Ala | |
| | | | 20 | | | | | 25 | | | | | 30 | | | |
| AAA | GGG | GAA | ACT | GCC | TAT | CTG | CCG | TGC | AAA | TTT | ACG | CTT | AGT | CCC | GAA | 144 |
| Lys | Gly | Glu | Thr | Ala | Tyr | Leu | Pro | Cys | Lys | Phe | Thr | Leu | Ser | Pro | Glu | |
| | | 35 | | | | | 40 | | | | | 45 | | | | |
| GAC | CAG | GGA | CCG | CTG | GAC | ATC | GAG | TGG | CTG | ATA | TCA | CCA | GCT | GAT | AAT | 192 |
| Asp | Gln | Gly | Pro | Leu | Asp | Ile | Glu | Trp | Leu | Ile | Ser | Pro | Ala | Asp | Asn | |
| | 50 | | | | | 55 | | | | | 60 | | | | | |
| CAG | AAG | GTG | GAT | CAA | GTG | ATT | ATT | TTA | TAT | TCT | GGA | GAC | AAA | ATT | TAT | 240 |
| Gln | Lys | Val | Asp | Gln | Val | Ile | Ile | Leu | Tyr | Ser | Gly | Asp | Lys | Ile | Tyr | |
| 65 | | | | | 70 | | | | | 75 | | | | | 80 | |
| GAT | GAC | TAC | TAT | CCA | GAT | CTG | AAA | GGC | CGA | GTA | CAT | TTT | ACG | AGT | AAT | 288 |
| Asp | Asp | Tyr | Tyr | Pro | Asp | Leu | Lys | Gly | Arg | Val | His | Phe | Thr | Ser | Asn | |
| | | | | 85 | | | | | 90 | | | | | 95 | | |
| GAT | CTC | AAA | TCT | GGT | GAT | GCA | TCA | ATA | AAT | GTA | ACG | AAT | TTA | CAA | CTG | 336 |
| Asp | Leu | Lys | Ser | Gly | Asp | Ala | Ser | Ile | Asn | Val | Thr | Asn | Leu | Gln | Leu | |
| | | | 100 | | | | | 105 | | | | | 110 | | | |
| TCA | GAT | ATT | GGC | ACA | TAT | CAG | TGC | AAA | GTG | AAA | AAA | GCT | CCT | GGT | GTT | 384 |
| Ser | Asp | Ile | Gly | Thr | Tyr | Gln | Cys | Lys | Val | Lys | Lys | Ala | Pro | Gly | Val | |
| | | 115 | | | | | 120 | | | | | 125 | | | | |
| GCA | AAT | AAG | AAG | ATT | CAT | CTG | GTA | GTT | CTT | GTT | AAG | CCT | TCA | GGT | GCG | 432 |
| Ala | Asn | Lys | Lys | Ile | His | Leu | Val | Val | Leu | Val | Lys | Pro | Ser | Gly | Ala | |
| | 130 | | | | | 135 | | | | | 140 | | | | | |
| AGA | TGT | TAC | GTT | GAT | GGA | TCT | GAA | GAA | ATT | GGA | AGT | GAC | TTT | AAG | ATA | 480 |
| Arg | Cys | Tyr | Val | Asp | Gly | Ser | Glu | Glu | Ile | Gly | Ser | Asp | Phe | Lys | Ile | |
| 145 | | | | | 150 | | | | | 155 | | | | | 160 | |
| AAA | TGT | GAA | CCA | AAA | GAA | GGT | TCA | CTT | CCA | TTA | CAG | TAT | GAG | TGG | CAA | 528 |
| Lys | Cys | Glu | Pro | Lys | Glu | Gly | Ser | Leu | Pro | Leu | Gln | Tyr | Glu | Trp | Gln | |
| | | | | 165 | | | | | 170 | | | | | 175 | | |
| AAA | TTG | TCT | GAC | TCA | CAG | AAA | ATG | CCC | ACT | TCA | TCG | TTA | GCA | GAA | ATG | 576 |
| Lys | Leu | Ser | Asp | Ser | Gln | Lys | Met | Pro | Thr | Ser | Ser | Leu | Ala | Glu | Met | |
| | | | 180 | | | | | 185 | | | | | 190 | | | |
| ACT | TCA | TCT | GTT | ATA | TCT | GTA | AAA | AAT | GCC | TCT | TCT | GAG | TAC | TCT | GGG | 624 |
| Thr | Ser | Ser | Val | Ile | Ser | Val | Lys | Asn | Ala | Ser | Ser | Glu | Tyr | Ser | Gly | |
| | | 195 | | | | | 200 | | | | | 205 | | | | |

```
ACA TAC AGC TGT ACA GTC AGA AAC AGA GTG GGC TCT GAT CAG TGC CTG        672
Thr Tyr Ser Cys Thr Val Arg Asn Arg Val Gly Ser Asp Gln Cys Leu
    210                 215                 220

TTG CGT CTA AAC GTT GTC CCT CCT TCA AAT AAA GCT GGA CTA ATT GCA        720
Leu Arg Leu Asn Val Val Pro Pro Ser Asn Lys Ala Gly Leu Ile Ala
225                 230                 235                 240

GGA GCC ATT ATA GGA ACT TTG CTT GCT CTA GCG CTC ATT GGT CTT ATC        768
Gly Ala Ile Ile Gly Thr Leu Leu Ala Leu Ala Leu Ile Gly Leu Ile
                245                 250                 255

ATC TTT TGC TGT CGT AAA AAG CGC AGA GAA GAA AAA TAT GAA AAG GAA        816
Ile Phe Cys Cys Arg Lys Lys Arg Arg Glu Glu Lys Tyr Glu Lys Glu
            260                 265                 270

GTT CAT CAC GAT ATC AGG GAA GAT GTG CCA CCT CCA AAG AGC CGT ACG        864
Val His His Asp Ile Arg Glu Asp Val Pro Pro Pro Lys Ser Arg Thr
        275                 280                 285

TCC ACT GCC AGA AGC TAC ATC GGC AGT AAT CAT TCA TCC CTG GGG TCC        912
Ser Thr Ala Arg Ser Tyr Ile Gly Ser Asn His Ser Ser Leu Gly Ser
    290                 295                 300

ATG TCT CCT TCC AAC ATG GAA GGA TAT TCC AAG ACT CAG TAT AAC CAA        960
Met Ser Pro Ser Asn Met Glu Gly Tyr Ser Lys Thr Gln Tyr Asn Gln
305                 310                 315                 320

GTA CCA AGT GAA GAC TTT GAA CGC ACT CCT CAG AGT CCG ACT CTC CCA       1008
Val Pro Ser Glu Asp Phe Glu Arg Thr Pro Gln Ser Pro Thr Leu Pro
                325                 330                 335

CCT GCT AAG GTA GCT GCC CCT AAT CTA AGT CGA ATG GGT GCG ATT CCT       1056
Pro Ala Lys Val Ala Ala Pro Asn Leu Ser Arg Met Gly Ala Ile Pro
            340                 345                 350

GTG ATG ATT CCA GCA CAG AGC AAG GAT GGG TCT ATA GTA                   1095
Val Met Ile Pro Ala Gln Ser Lys Asp Gly Ser Ile Val
        355                 360                 365

(2) INFORMATION FOR SEQ ID NO:4:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:4:

Thr Gln Tyr Asn Gln Val Pro Ser Glu Asp Phe Glu Arg
1               5                   10

(2) INFORMATION FOR SEQ ID NO:5:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:5:

Thr Pro Gln Ser Pro Thr Leu Pro Pro Ala Lys
1               5                   10

(2) INFORMATION FOR SEQ ID NO:6:

(i) SEQUENCE CHARACTERISTICS:
        (A) LENGTH: 8 amino acids
```

(B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:6:

Val Ala Ala Pro Asn Leu Ser Arg
 1               5

(2) INFORMATION FOR SEQ ID NO:7:

(i) SEQUENCE CHARACTERISTICS:
            (A) LENGTH: 13 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:7:

Met Gly Ala Ile Pro Val Met Ile Pro Ala Gln Ser Lys
 1               5                  10

(2) INFORMATION FOR SEQ ID NO:8:

(i) SEQUENCE CHARACTERISTICS:
            (A) LENGTH: 106 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:8:

Gly Glu Thr Ala Tyr Leu Pro Cys Lys Phe Thr Leu Ser Pro Glu Asp
 1               5                  10                  15

Gln Gly Pro Leu Asp Ile Glu Trp Leu Ile Ser Pro Ala Asp Asn Gln
                20                  25                  30

Lys Val Asp Gln Val Ile Ile Leu Tyr Ser Gly Asp Lys Ile Tyr Asp
            35                  40                  45

Asp Tyr Tyr Pro Asp Leu Lys Gly Arg Val His Phe Thr Ser Asn Asp
        50                  55                  60

Leu Lys Ser Gly Asp Ala Ser Ile Asn Val Thr Asn Leu Gln Leu Ser
65                  70                  75                  80

Asp Ile Gly Thr Tyr Gln Cys Lys Val Lys Lys Ala Pro Gly Val Ala
                85                  90                  95

Asn Lys Lys Ile His Leu Val Val Leu Val
                100                 105

(2) INFORMATION FOR SEQ ID NO:9:

(i) SEQUENCE CHARACTERISTICS:
            (A) LENGTH: 101 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:9:

Gly Gln Asn Ala Thr Leu Tyr Cys Thr Tyr Ile Leu Asn Asn Gln Asn

```
                1               5                    10                   15
Lys Asn Asn Leu Val Ile Gln Trp Asn Ile Phe Gln Ala Lys Ser Gln
                    20                  25                  30

Asn Gln Glu Thr Val Phe Phe Tyr Gln Asn Gly Gln Ser Leu Ser Gly
                35                  40                  45

Pro Ser Tyr Lys Asn Arg Val Thr Ala Ala Met Ser Pro Gly Asn Ala
 50                      55                  60

Thr Ile Thr Ile Ser Asn Met Gln Ser Gln Asp Thr Gly Ile Tyr Thr
 65                  70                  75                  80

Cys Glu Val Leu Asn Leu Pro Glu Ser Ser Gly Gln Gly Lys Ile Leu
                    85                  90                  95

Leu Thr Val Leu Val
                100
```

(2) INFORMATION FOR SEQ ID NO:10:

(i) SEQUENCE CHARACTERISTICS:
        (A) LENGTH: 95 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:10:

```
Asn Gly Thr Ala Tyr Leu Pro Cys Pro Phe Thr Lys Ala Gln Asn Ile
 1               5                    10                  15

Ser Leu Ser Glu Leu Val Val Phe Trp Gln Asp Gln Gln Lys Leu Val
                    20                  25                  30

Leu Tyr Glu His Tyr Leu Gly Thr Glu Lys Leu Asp Ser Val Asn Ala
                35                  40                  45

Lys Tyr Leu Gly Arg Thr Ser Phe Asp Arg Asn Asn Trp Thr Leu Arg
 50                      55                  60

Leu His Asn Val Gln Ile Lys Asp Met Gly Ser Tyr Asp Cys Phe Ile
 65                  70                  75                  80

Gln Lys Lys Pro Pro Thr Gly Ser Ile Ile Leu Gln Gln Thr Leu
                    85                  90                  95
```

(2) INFORMATION FOR SEQ ID NO:11:

(i) SEQUENCE CHARACTERISTICS:
        (A) LENGTH: 72 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:11:

```
Gly Asp Thr Val Ile Ile Ser Cys Thr Cys Gly Asn Val Pro Glu Thr
 1               5                    10                  15

Trp Ile Ile Leu Lys Lys Lys Ala Lys Thr Gly Asp Met Val Leu Lys
                    20                  25                  30

Ser Val Asp Gly Ser Tyr Thr Ile Arg Gln Ala Gln Leu Gln Asp Ala
                35                  40                  45

Gly Ile Tyr Glu Cys Glu Ser Lys Thr Glu Val Gly Ser Gln Leu Arg
 50                      55                  60

Ser Leu Thr Leu Asp Val Lys Gly
```

```
65                  70
```

(2) INFORMATION FOR SEQ ID NO:12:

(i) SEQUENCE CHARACTERISTICS:
        (A) LENGTH: 69 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:12:

```
Gly Glu Thr Val Thr Leu Arg Cys Val Ser Asn Gly Ser Val Glu Trp
1               5                  10                  15

Asp Gly Pro Ile Ser Pro Tyr Trp Thr Leu Asp Pro Glu Ser Pro Gly
                20                  25                  30

Ser Thr Leu Thr Thr Arg Asn Ala Thr Phe Lys Asn Thr Gly Thr Tyr
            35                  40                  45

Arg Cys Thr Glu Leu Glu Asp Pro Met Ala Gly Ser Thr Thr Ile His
    50                  55                  60

Leu Tyr Val Lys Asp
65
```

(2) INFORMATION FOR SEQ ID NO:13:

(i) SEQUENCE CHARACTERISTICS:
        (A) LENGTH: 75 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:13:

```
Gly Gln Asn Val Thr Leu Glu Cys Phe Ala Leu Gly Asn Pro Val Pro
1               5                  10                  15

Asp Ile Arg Trp Arg Lys Val Leu Glu Pro Met Pro Ser Thr Ala Glu
                20                  25                  30

Ile Ser Thr Ser Gly Ala Val Leu Lys Ile Phe Asn Ile Gln Leu Glu
            35                  40                  45

Asp Glu Gly Ile Tyr Glu Cys Glu Ala Glu Asn Ile Arg Gly Lys Asp
    50                  55                  60

Lys His Gln Ala Arg Ile Tyr Val Gln Ala Phe
65                  70                  75
```

(2) INFORMATION FOR SEQ ID NO:14:

(i) SEQUENCE CHARACTERISTICS:
        (A) LENGTH: 99 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:14:

```
Gly Glu Thr Ala Ser Phe Pro Cys Asp Leu Thr Gln Gly Ala Thr Tyr
1               5                  10                  15

Ile His Leu Tyr Lys His Glu Glu Gly Met Ala Pro Arg Arg Leu Leu
                20                  25                  30
```

Tyr Tyr Asp Ser Tyr Asn Ser Lys Thr Val Leu Glu Ser Gly Ile Ser
                35                  40                  45

Gly Thr Lys Tyr His Val Tyr Lys Gly Thr Gly Arg Ser Tyr Thr Phe
    50                  55                  60

Thr Ile Val Asn Leu Gln Ala Ser Asp Ser Gly Ile Tyr Tyr Cys Ala
65                  70                  75                  80

Ile Asn Arg Ser Ser Gly Trp Arg Lys Ile Phe Gly Glu Gly Ala Asn
                85                  90                  95

Ile Ile Val (2) INFORMATION FOR SEQ ID NO:15:

(i) SEQUENCE CHARACTERISTICS:
        (A) LENGTH: 92 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:15:

Gly Thr Gly Ser Ala Leu Arg Cys Asn Phe Thr Thr Thr Met Arg Ala
1               5                   10                  15

Val Gln Trp Phe Gln Gln Asn Ser Arg Gly Ser Leu Ile Asn Leu Phe
                20                  25                  30

Tyr Leu Ala Ser Gly Thr Lys Glu Asn Gly Arg Leu Lys Ser Thr Phe
                35                  40                  45

Asn Ser Lys Glu Ser Tyr Ser Thr Leu His Ile Arg Asp Ala Gln Leu
    50                  55                  60

Glu Asp Ser Gly Thr Tyr Phe Cys Ala Ala Leu Arg Ala Thr Gly Gly
65                  70                  75                  80

Asn Asn Lys Leu Thr Phe Gly Gln Gly Thr Val Leu
                85                  90

(2) INFORMATION FOR SEQ ID NO:16:

(i) SEQUENCE CHARACTERISTICS:
        (A) LENGTH: 84 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:16:

Gly Glu Ser Val Lys Leu Ser Cys Lys Thr Ser Gly Tyr Thr Phe Thr
1               5                   10                  15

Ser Tyr Trp Ile His Trp Ile Gln Gln Val Pro Glu Lys Gly Leu Gln
                20                  25                  30

Trp Ile Gly Ala Ile His Pro Gly Asn Ala Asp Thr Arg Tyr Ser Arg
                35                  40                  45

Ser Tyr Gln Gly Arg Cys His Ile Ser Thr Asp Asn Ser Gln Gly Thr
    50                  55                  60

Ala Phe Leu Gln Leu Asn Asn Leu Lys Val Glu Asp Thr Ala Met Tyr
65                  70                  75                  80

Tyr Cys Ala Arg (2) INFORMATION FOR SEQ ID NO:17:

(i) SEQUENCE CHARACTERISTICS:
        (A) LENGTH: 95 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:17:

```
Pro Ser Gly Ala Arg Cys Tyr Val Asp Gly Ser Glu Glu Ile Gly Ser
1               5                   10                  15

Asp Phe Lys Ile Lys Cys Glu Pro Lys Glu Gly Ser Leu Pro Leu Gln
            20                  25                  30

Tyr Glu Trp Gln Lys Leu Ser Asp Ser Gln Lys Met Pro Thr Ser Trp
        35                  40                  45

Leu Ala Glu Met Thr Ser Ser Val Ile Ser Val Lys Asn Ala Ser Ser
    50                  55                  60

Glu Tyr Ser Gly Thr Tyr Ser Cys Thr Val Arg Asn Arg Val Gly Ser
65                  70                  75                  80

Asp Gln Cys Leu Leu Arg Leu Asn Val Val Pro Pro Ser Asn Lys
                85                  90                  95
```

(2) INFORMATION FOR SEQ ID NO:18:

(i) SEQUENCE CHARACTERISTICS:
        (A) LENGTH: 95 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:18:

```
Pro Ser Val Pro His Cys Ser Ile Arg Gly Ala Val Glu Thr Gly His
1               5                   10                  15

Phe Ile Ser Leu Leu Cys Tyr Ser Glu Glu Gly Met Pro Arg Pro Ile
            20                  25                  30

Tyr Ser Trp Asn Arg Val Glu Asn Gly Leu Leu Lys Ser Thr Pro Ser
        35                  40                  45

Gln Met Asn Gln Gln Lys Gly Ser Leu Ile Ile Gly Asn Leu Thr Asp
    50                  55                  60

Phe Glu Glu Gly Tyr Tyr Arg Cys Thr Ala Ser Asn Asn Leu Gly Asn
65                  70                  75                  80

Ala Thr Cys Glu Leu Asn Leu His Thr Gly Gly Val Ile Ala
                85                  90                  95
```

(2) INFORMATION FOR SEQ ID NO:19:

(i) SEQUENCE CHARACTERISTICS:
        (A) LENGTH: 93 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:19:

```
Leu Glu Val Gln Ile His Pro Ser Arg Ser Val Val Pro Gln Gly Gly
1               5                   10                  15
```

```
Pro His Ser Leu Arg Cys Gln Val Ser Gly Ser Pro His Tyr Phe
            20                  25                  30

Tyr Trp Ser Arg Glu Asp Gly Arg Pro Leu Pro Ser Ser Ala Gln Gln
            35                  40                  45

Arg His Gln Gly Ser Glu Leu His Phe Pro Ser Val Gln Pro Ser Asp
            50                  55                  60

Ala Gly Val Tyr Ile Cys Thr Cys Arg Asn Leu Ile His Thr Ser Asn
 65              70                  75                      80

Ser Arg Ala Glu Leu Leu Val Ala Glu Ala Pro Ser Lys
                85                  90
```

(2) INFORMATION FOR SEQ ID NO:20:

(i) SEQUENCE CHARACTERISTICS:
        (A) LENGTH: 93 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:20:

```
Pro Val Ile Ser Ile Glu Pro Pro Ser Ser Thr Val Gln Gln Gly Gln
 1               5                  10                  15

Asp Ala Ser Phe Lys Cys Leu Ile His Glu Gly Ala Met Pro Ile Lys
            20                  25                  30

Val Glu Trp Lys Ile Arg Asp Gln Glu Leu Glu Asp Asn Val His Ile
            35                  40                  45

Ser Pro Asn Gly Ser Ile Ile Thr Ile Val Ala Pro Gly Pro Ala Thr
 50                  55                  60

Met Glu Pro Thr Ala Cys Val Ala Ser Asn Val Tyr Gly Met Ala Gln
 65              70                  75                      80

Ser Val Val Asn Leu Ser Val His Gly Pro Pro Thr Val
                85                  90
```

(2) INFORMATION FOR SEQ ID NO:21:

(i) SEQUENCE CHARACTERISTICS:
        (A) LENGTH: 94 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:21:

```
Glu Val Gln Ile Ser Ile Leu Ser Ser Lys Val Val Glu Ser Gly Glu
 1               5                  10                  15

Asp Ile Val Leu Gln Cys Ala Val Asn Glu Gly Ser Gly Pro Ile Thr
            20                  25                  30

Tyr Lys Phe Tyr Arg Glu Lys Glu Gly Lys Pro Phe Tyr Gln Met Thr
            35                  40                  45

Ser Asn Ala Thr Gln Ala Phe Trp Thr Lys Gln Lys Ala Ser Lys Glu
            50                  55                  60

Gln Glu Gly Glu Tyr Tyr Cys Thr Ala Phe Asn Arg Ala Asn His Ala
 65              70                  75                      80

Ser Ser Val Pro Arg Ser Lys Ile Leu Thr Val Arg Val Ile
                85                  90
```

(2) INFORMATION FOR SEQ ID NO:22:

(i) SEQUENCE CHARACTERISTICS:
        (A) LENGTH: 90 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:22:

```
Asp Thr Thr Val Leu Val Ser Pro Ser Ser Ile Leu Glu Glu Gly Ser
1               5                   10                  15

Ser Val Asn Met Thr Cys Leu Ser Gln Gly Phe Pro Ala Pro Lys Ile
            20                  25                  30

Leu Trp Ser Arg Gln Leu Pro Asn Gly Glu Leu Gln Pro Leu Ser Glu
        35                  40                  45

Asn Ala Thr Leu Thr Leu Ile Ser Thr Lys Met Glu Asp Ser Gly Val
    50                  55                  60

Tyr Leu Cys Glu Gly Ile Asn Gln Ala Gly Arg Ser Arg Lys Glu Val
65                  70                  75                  80

Glu Leu Ile Ile Gln Val Thr Pro Lys Asp
                85                  90
```

(2) INFORMATION FOR SEQ ID NO:23:

(i) SEQUENCE CHARACTERISTICS:
        (A) LENGTH: 365 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:23:

```
Met Ala Arg Leu Leu Cys Phe Val Leu Leu Cys Gly Ile Ala Asp Phe
1               5                   10                  15

Thr Ser Gly Leu Ser Ile Thr Thr Pro Glu Gln Arg Ile Glu Lys Ala
            20                  25                  30

Lys Gly Glu Thr Ala Tyr Leu Pro Cys Lys Phe Thr Leu Ser Pro Glu
        35                  40                  45

Asp Gln Gly Pro Leu Asp Ile Glu Trp Leu Ile Ser Pro Ser Asp Asn
    50                  55                  60

Gln Ile Val Asp Gln Val Ile Ile Leu Tyr Ser Gly Asp Lys Ile Tyr
65                  70                  75                  80

Asp Asn Tyr Tyr Pro Asp Leu Lys Gly Arg Val His Phe Thr Ser Asn
                85                  90                  95

Asp Val Lys Ser Gly Asp Ala Ser Ile Asn Val Thr Asn Leu Gln Leu
            100                 105                 110

Ser Asp Ile Gly Thr Tyr Gln Cys Lys Val Lys Ala Pro Gly Val
        115                 120                 125

Ala Asn Lys Lys Phe Leu Leu Thr Val Leu Val Lys Pro Ser Gly Thr
    130                 135                 140

Arg Cys Phe Val Asp Gly Ser Glu Glu Ile Gly Asn Asp Phe Lys Leu
145                 150                 155                 160

Lys Cys Glu Pro Lys Glu Gly Ser Leu Pro Leu Gln Phe Glu Trp Gln
                165                 170                 175
```

```
Lys Leu Ser Asp Ser Gln Thr Met Pro Thr Ser Trp Leu Ala Glu Met
            180                 185                 190
Thr Ser Pro Val Ile Ser Val Lys Asn Ala Ser Ser Glu Tyr Ser Gly
            195                 200                 205
Thr Tyr Ser Cys Thr Val Gln Asn Arg Val Gly Ser Asp Gln Cys Met
            210                 215                 220
Leu Arg Leu Asp Val Val Pro Pro Ser Asn Arg Ala Gly Thr Ile Ala
225                 230                 235                 240
Gly Ala Val Ile Gly Thr Leu Leu Ala Leu Val Leu Ile Gly Ala Ile
                245                 250                 255
Leu Phe Cys Cys His Arg Lys Arg Arg Glu Glu Lys Tyr Glu Lys Glu
            260                 265                 270
Val His His Asp Ile Arg Glu Asp Val Pro Pro Lys Ser Arg Thr
            275                 280                 285
Ser Thr Ala Arg Ser Tyr Ile Gly Ser Asn His Ser Ser Leu Gly Ser
            290                 295                 300
Met Ser Pro Ser Asn Met Glu Gly Tyr Ser Lys Thr Gln Tyr Asn Gln
305                 310                 315                 320
Val Pro Ser Glu Asp Phe Glu Arg Ala Pro Gln Ser Pro Thr Leu Ala
                325                 330                 335
Pro Ala Lys Val Ala Ala Pro Asn Leu Ser Arg Met Gly Ala Val Pro
                340                 345                 350
Val Met Ile Pro Ala Gln Ser Lys Asp Gly Ser Ile Val
                355                 360                 365

(2) INFORMATION FOR SEQ ID NO:24:

(i) SEQUENCE CHARACTERISTICS:
        (A) LENGTH: 365 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:24:

Met Ala Arg Leu Leu Cys Phe Val Leu Leu Cys Gly Ile Ala Asp Phe
1               5                   10                  15
Thr Ser Gly Leu Ser Ile Thr Thr Pro Glu Gln Arg Ile Glu Lys Ala
            20                  25                  30
Lys Gly Glu Thr Ala Tyr Leu Pro Cys Lys Phe Thr Leu Ser Pro Glu
            35                  40                  45
Asp Gln Gly Pro Leu Asp Ile Glu Trp Leu Ile Ser Pro Ser Asp Asn
50                  55                  60
Gln Ile Val Asp Gln Val Ile Ile Leu Tyr Ser Gly Asp Lys Ile Tyr
65                  70                  75                  80
Asp Asn Tyr Tyr Pro Asp Leu Lys Gly Arg Val His Phe Thr Ser Asn
                85                  90                  95
Asp Val Lys Ser Gly Asp Ala Ser Ile Asn Val Thr Asn Leu Gln Leu
            100                 105                 110
Ser Asp Ile Gly Thr Tyr Gln Cys Lys Val Lys Lys Ala Pro Gly Val
            115                 120                 125
Ala Asn Lys Lys Phe Leu Leu Thr Val Leu Val Lys Pro Ser Gly Thr
130                 135                 140
Arg Cys Phe Val Asp Gly Ser Glu Glu Ile Gly Asn Asp Phe Lys Leu
```

-continued

```
                    145                 150                 155                 160
Lys Cys Glu Pro Lys Glu Gly Ser Leu Pro Leu Gln Phe Glu Trp Gln
                165                 170                 175

Lys Leu Ser Asp Ser Gln Thr Met Pro Thr Ser Trp Leu Ala Glu Met
            180                 185                 190

Thr Ser Pro Val Ile Ser Val Lys Asn Ala Ser Ser Glu Tyr Ser Gly
        195                 200                 205

Thr Tyr Ser Cys Thr Val Gln Asn Arg Val Gly Ser Asp Gln Cys Met
    210                 215                 220

Leu Arg Leu Asp Val Val Pro Pro Ser Asn Arg Ala Gly Thr Ile Ala
225                 230                 235                 240

Gly Ala Val Ile Gly Thr Leu Leu Ala Leu Val Leu Ile Gly Ala Ile
                245                 250                 255

Leu Phe Cys Cys His Arg Lys Arg Glu Glu Lys Tyr Glu Lys Glu
            260                 265                 270

Val His His Asp Ile Arg Glu Asp Val Pro Pro Lys Ser Arg Thr
        275                 280                 285

Ser Thr Ala Arg Ser Tyr Ile Gly Ser Asn His Ser Ser Leu Gly Ser
    290                 295                 300

Met Ser Pro Ser Asn Met Glu Gly Tyr Ser Lys Thr Gln Tyr Asn Gln
305                 310                 315                 320

Val Pro Ser Glu Asp Phe Glu Arg Ala Pro Gln Ser Pro Thr Leu Ala
                325                 330                 335

Pro Ala Lys Phe Lys Tyr Ala Tyr Lys Thr Asp Gly Ile Thr Val Val
            340                 345                 350

Val Met Ile Pro Ala Gln Ser Lys Asp Gly Ser Ile Val
        355                 360                 365
```

(2) INFORMATION FOR SEQ ID NO:25:

(i) SEQUENCE CHARACTERISTICS:
        (A) LENGTH: 1515 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1095

(xi) SEQUENCE DESCRIPTION: SEQ ID NO:25:

```
ATG GCG CGC CTA CTG TGC TTC GTG CTC TTG TGC GGG ATC GCG GAT TTC        48
Met Ala Arg Leu Leu Cys Phe Val Leu Leu Cys Gly Ile Ala Asp Phe
1               5                  10                  15

ACC AGT GGT TTG AGC ATC ACT ACA CCC GAA CAG AGG ATC GAA AAA GCC        96
Thr Ser Gly Leu Ser Ile Thr Thr Pro Glu Gln Arg Ile Glu Lys Ala
            20                  25                  30

AAA GGG GAA ACT GCG TAT CTA CCA TGC AAG TTT ACT CTC AGT CCC GAA       144
Lys Gly Glu Thr Ala Tyr Leu Pro Cys Lys Phe Thr Leu Ser Pro Glu
        35                  40                  45

GAC CAG GGA CCA CTG GAC ATT GAA TGG CTG ATA TCC CCG TCT GAT AAC       192
Asp Gln Gly Pro Leu Asp Ile Glu Trp Leu Ile Ser Pro Ser Asp Asn
    50                  55                  60

CAG ATA GTG GAT CAA GTG ATC ATT TTG TAT TCT GGA GAC AAA ATT TAT       240
Gln Ile Val Asp Gln Val Ile Ile Leu Tyr Ser Gly Asp Lys Ile Tyr
65                  70                  75                  80

GAT AAC TAC TAT CCG GAT CTG AAA GGA CGG GTA CAT TTT ACG AGT AAC       288
```

-continued

```
Asp Asn Tyr Tyr Pro Asp Leu Lys Gly Arg Val His Phe Thr Ser Asn
            85                  90                  95

GAT GTC AAG TCT GGC GAC GCA TCT ATA AAT GTG ACC AAC CTG CAG CTG        336
Asp Val Lys Ser Gly Asp Ala Ser Ile Asn Val Thr Asn Leu Gln Leu
            100                 105                 110

TCG GAC ATT GGC ACT TAC CAG TGC AAA GTG AAG AAA GCC CCT GGG GTT        384
Ser Asp Ile Gly Thr Tyr Gln Cys Lys Val Lys Lys Ala Pro Gly Val
            115                 120                 125

GCA AAT AAG AAA TTC CTG CTG ACC GTT CTT GTT AAG CCT TCA GGT ACA        432
Ala Asn Lys Lys Phe Leu Leu Thr Val Leu Val Lys Pro Ser Gly Thr
130                 135                 140

AGA TGC TTC GTG GAT GGA TCG GAA GAG ATT GGA AAT GAC TTC AAG CTA        480
Arg Cys Phe Val Asp Gly Ser Glu Glu Ile Gly Asn Asp Phe Lys Leu
145                 150                 155                 160

AAA TGT GAA CCC AAG GAA GGC TCC CTT CCA CTA CAG TTT GAA TGG CAG        528
Lys Cys Glu Pro Lys Glu Gly Ser Leu Pro Leu Gln Phe Glu Trp Gln
                165                 170                 175

AAA CTG TCG GAC TCC CAG ACA ATG CCT ACG CCA TGG CTG GCA GAA ATG        576
Lys Leu Ser Asp Ser Gln Thr Met Pro Thr Pro Trp Leu Ala Glu Met
            180                 185                 190

ACG TCA CCA GTT ATA TCT GTG AAG AAC GCC AGT TCT GAG TAT TCT GGG        624
Thr Ser Pro Val Ile Ser Val Lys Asn Ala Ser Ser Glu Tyr Ser Gly
            195                 200                 205

ACA TAC AGC TGC ACG GTT CAA AAC AGA GTG GGC TCT GAC CAG TGT ATG        672
Thr Tyr Ser Cys Thr Val Gln Asn Arg Val Gly Ser Asp Gln Cys Met
            210                 215                 220

CTG CGA CTA GAC GTT GTC CCA CCC TCC AAC CGA GCC GGA ACG ATC GCG        720
Leu Arg Leu Asp Val Val Pro Pro Ser Asn Arg Ala Gly Thr Ile Ala
225                 230                 235                 240

GGC GCC GTC ATA GGG ACG CTG CTG GCC CTT GTG CTC ATC GGG GCC ATC        768
Gly Ala Val Ile Gly Thr Leu Leu Ala Leu Val Leu Ile Gly Ala Ile
            245                 250                 255

CTC TTC TGC TGT CAC AGG AAA CGC AGA GAA GAG AAG TAC GAG AAG GAA        816
Leu Phe Cys Cys His Arg Lys Arg Arg Glu Glu Lys Tyr Glu Lys Glu
            260                 265                 270

GTT CAT CAT GAT ATC AGG GAA GAT GTG CCT CCT CCA AAG AGT CGG ACA        864
Val His His Asp Ile Arg Glu Asp Val Pro Pro Pro Lys Ser Arg Thr
            275                 280                 285

TCC ACT GCC AGG AGC TAT ATT GGC AGC AAC CAT TCA TCC CTG GGA TCC        912
Ser Thr Ala Arg Ser Tyr Ile Gly Ser Asn His Ser Ser Leu Gly Ser
    290                 295                 300

ATG TCC CCC TCT AAC ATG GAG GGG TAT TCC AAG ACG CAG TAT AAC CAA        960
Met Ser Pro Ser Asn Met Glu Gly Tyr Ser Lys Thr Gln Tyr Asn Gln
305                 310                 315                 320

GTC CCC AGT GAA GAC TTT GAA CGT GCG CCT CAG AGC CCG ACT CTG GCA        1008
Val Pro Ser Glu Asp Phe Glu Arg Ala Pro Gln Ser Pro Thr Leu Ala
            325                 330                 335

CCC GCT AAG GTA GCT GCC CCT AAT CTC AGT CGA ATG GGA GCG GTT CCT        1056
Pro Ala Lys Val Ala Ala Pro Asn Leu Ser Arg Met Gly Ala Val Pro
            340                 345                 350

GTG ATG ATT CCT GCA CAG AGC AAG GAC GGG TCT ATA GTA TAGAACTCCG         1105
Val Met Ile Pro Ala Gln Ser Lys Asp Gly Ser Ile Val
            355                 360                 365

CACCTCTCTG TTCTGCTGTC CGTAAAAANNN CANNNNNTNT TTTTNTTNTT NTTNNTNNNN     1165

NNCNANNNNA TCNTNNNNCN CNNGCTNNNA NNNNATCTGA CGCACAGCTG AGGTGAGCCG     1225

TGATGTCCTG TTGTCTGCCT CNGCCTCTCA GTTATGGGAT TCAGGCACT CCCANTACNT      1285

CCNGTTTACN AGGCGGGTTA ACAGTGGCTA CAGGAACNCA TCTGCTTTCT CTGATGGGAG     1345
```

```
AACGCNAATA NTCANATNTC CTATAACGTC ATNGNGGGTC NGAATCCCCN TGACNANGGT    1405

CCCATATAGA CNGGANTTNG ATTGANNGGC TGAAATTNGT TTTATTGTNG GTANAANTTT    1465

CCTTNNNNCG GCNACCAGTG ATTTAGAAAT NNTTTANGTG TNNNTTTTTN               1515
```

(2) INFORMATION FOR SEQ ID NO:26:

(i) SEQUENCE CHARACTERISTICS:
        (A) LENGTH: 365 amino acids
        (B) TYPE: amino acid
        (D) TOPOLOGY: linear (ii) MOLECULE TYPE: protein (xi) SEQUENCE DESCRIPTION: SEQ ID NO:26:

```
Met Ala Arg Leu Leu Cys Phe Val Leu Leu Cys Gly Ile Ala Asp Phe
  1               5                  10                  15

Thr Ser Gly Leu Ser Ile Thr Thr Pro Glu Gln Arg Ile Glu Lys Ala
             20                  25                  30

Lys Gly Glu Thr Ala Tyr Leu Pro Cys Lys Phe Thr Leu Ser Pro Glu
         35                  40                  45

Asp Gln Gly Pro Leu Asp Ile Glu Trp Leu Ile Ser Pro Ser Asp Asn
     50                  55                  60

Gln Ile Val Asp Gln Val Ile Leu Tyr Ser Gly Asp Lys Ile Tyr
 65                  70                  75                  80

Asp Asn Tyr Tyr Pro Asp Leu Lys Gly Arg Val His Phe Thr Ser Asn
                 85                  90                  95

Asp Val Lys Ser Gly Asp Ala Ser Ile Asn Val Thr Asn Leu Gln Leu
            100                 105                 110

Ser Asp Ile Gly Thr Tyr Gln Cys Lys Val Lys Lys Ala Pro Gly Val
        115                 120                 125

Ala Asn Lys Lys Phe Leu Leu Thr Val Leu Val Lys Pro Ser Gly Thr
    130                 135                 140

Arg Cys Phe Val Asp Gly Ser Glu Glu Ile Gly Asn Asp Phe Lys Leu
145                 150                 155                 160

Lys Cys Glu Pro Lys Glu Gly Ser Leu Pro Leu Gln Phe Glu Trp Gln
                165                 170                 175

Lys Leu Ser Asp Ser Gln Thr Met Pro Thr Pro Trp Leu Ala Glu Met
            180                 185                 190

Thr Ser Pro Val Ile Ser Val Lys Asn Ala Ser Ser Glu Tyr Ser Gly
        195                 200                 205

Thr Tyr Ser Cys Thr Val Gln Asn Arg Val Gly Ser Asp Gln Cys Met
    210                 215                 220

Leu Arg Leu Asp Val Val Pro Pro Ser Asn Arg Ala Gly Thr Ile Ala
225                 230                 235                 240

Gly Ala Val Ile Gly Thr Leu Leu Ala Leu Val Leu Ile Gly Ala Ile
                245                 250                 255

Leu Phe Cys Cys His Arg Lys Arg Arg Glu Glu Lys Tyr Glu Lys Glu
            260                 265                 270

Val His His Asp Ile Arg Glu Asp Val Pro Pro Lys Ser Arg Thr
        275                 280                 285

Ser Thr Ala Arg Ser Tyr Ile Gly Ser Asn His Ser Ser Leu Gly Ser
    290                 295                 300

Met Ser Pro Ser Asn Met Glu Gly Tyr Ser Lys Thr Gln Tyr Asn Gln
305                 310                 315                 320

Val Pro Ser Glu Asp Phe Glu Arg Ala Pro Gln Ser Pro Thr Leu Ala
```

```
                    325                 330                 335
Pro Ala Lys Val Ala Ala Pro Asn Leu Ser Arg Met Gly Ala Val Pro
                340                 345                 350
Val Met Ile Pro Ala Gln Ser Lys Asp Gly Ser Ile Val
            355                 360                 365
```